United States Patent
Larijani et al.

(10) Patent No.: US 10,184,944 B2
(45) Date of Patent: Jan. 22, 2019

(54) METHODS FOR DETECTING MOLECULES IN A SAMPLE

(71) Applicant: The Francis Crick Institute Limited, London (GB)

(72) Inventors: Banafshe Larijani, London (GB); Peter Parker, London (GB); Selvaraju Veeriah, London (GB)

(73) Assignee: The Francis Crick Institute Limited, London (GB)

( * ) Notice: Subject to any disclaimer, the term of this patent is extended or adjusted under 35 U.S.C. 154(b) by 7 days.

(21) Appl. No.: 14/778,532

(22) PCT Filed: Mar. 11, 2014

(86) PCT No.: PCT/GB2014/050715
§ 371 (c)(1),
(2) Date: Sep. 18, 2015

(87) PCT Pub. No.: WO2014/140554
PCT Pub. Date: Sep. 18, 2014

(65) Prior Publication Data
US 2016/0069881 A1    Mar. 10, 2016

(30) Foreign Application Priority Data
Mar. 11, 2013  (GB) .................................. 1304352.6

(51) Int. Cl.
*G01N 33/53* (2006.01)
*G01N 33/574* (2006.01)
*G01N 33/543* (2006.01)

(52) U.S. Cl.
CPC . *G01N 33/57415* (2013.01); *G01N 33/54373* (2013.01); *G01N 2458/00* (2013.01)

(58) Field of Classification Search
None
See application file for complete search history.

(56) References Cited

U.S. PATENT DOCUMENTS

2011/0124520 A1 * 5/2011 Love .................. C12Q 1/02
506/9
2014/0112931 A1 * 4/2014 Chardes ............ C07K 16/32
424/143.1

OTHER PUBLICATIONS

Koning et al. (Laboratory Investigation (2006) 86, 853-864 Laboratory Investigation (2006) 86, 853-864).*

(Continued)

*Primary Examiner* — Changhwa J Cheu
(74) *Attorney, Agent, or Firm* — Knobbe, Martens, Olson & Bear, LLP

(57) ABSTRACT

The present invention relates to a method for detecting molecules. The method employs: at least two primary antibodies, wherein the first primary antibody binds to a first site on a molecule and the second primary antibody binds to a second site on a molecule, wherein the second site is different from the first site and wherein the first and second primary antibodies are immunologically distinct; at least two secondary antibodies, wherein the first secondary antibody is labelled with a fluorescence resonance energy transfer (FRET) donor and binds to the first primary antibody; and the second secondary antibody is conjugated or fused to an enzyme and binds the second primary antibody, wherein the first secondary antibody does not bind the second primary antibody and the second secondary antibody does not bind the first primary antibody; a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme; wherein the method comprises: contacting a sample with the at least two primary antibodies; contacting the sample with the at least two secondary antibodies; performing a wash step; contacting the sample with the conjugate; and detecting any FRET signal generated by the FRET acceptor.

33 Claims, 36 Drawing Sheets

(56) References Cited

OTHER PUBLICATIONS

Jares-Erijman (Nature Biotechnology vol. 2 | No. 11 Nov. 2003).*
Huang et al. (Analyst 2012 vol. 137, p. 3659-3666).*
Bellacosa, A. et al Activation of AKT kinases in cancer: implications for therapeutic targeting. *Advances in Cancer Research* 94, 29-86 (2005).
Bertucci, F. et al Reasons for breast cancer heterogeneity. *Journal of Biology* 7, 6 (2008).
Calleja, V. et al Intramolecular and intermolecular interactions of protein kinase B define its activation in vivo. *PLoS Biology* 5, e95 (2007).
Calleja, V. et al Role of a Novel PH-Kinase Domain Interface in PKB/Akt Regulation: Structural Mechanism for Allosteric Inhibition. *PLoS Biology* 7, 1 (2009).
Calleja, V. et al Protein activation dynamics in cells and tumour micro arrays assessed by time resolved Förster resonance energy transfer. *Methods in Enzymology* 506, 225-46 (2012).
Chames, P. et al Therapeutic antibodies: successes, limitations and hopes for the future. *British Journal of Pharmacology* 157, 220-33 (2009).
Chin et al Microtubule-affinity regulating kinase (MARK) is tightly associated with Neurofibrillary Tangles in Alzheimer Brain: A Fluorescent Resonance Energy Transfer Study. *J. Neuropathology and Experimental Neurology*, vol. 59, No. 11, pp. 966-971 (2000).
Chin, Y. R et al Function of Akt/PKB signaling to cell motility, invasion and the tumour stroma in cancer. *Cellular Signalling* 21, 470-476 (2009).
Förster, T. Zwischenmolekulare Energiewanderung and Fluoreszenz. *Annalen der Physik* 437, 55-75 (1948).
Gerlinger, M. et al Intratumour heterogeneity and branched evolution revealed by multiregion sequencing. *The New England Journal of Medicine* 366, 883-92 (2012).
Grille, S. J. et al. The protein kinase Akt induces epithelial mesenchymal transition and promotes enhanced motility and invasiveness of squamous cell carcinoma lines. *Cancer Res* 63, 2172-2178 (2003).
Heeg, S. et al. EGFR overexpression induces activation of telomerase via PI3K/AKT-mediated phosphorylation and transcriptional regulation through Hif1-alpha in a cellular model of oral-esophageal carcinogenesis. *Cancer Science* 102, 351-60 (2011).
Jares-Erihman et al FRET Imaging Nature Biotechnology vol. 21, No. 11 pp. 1387-1395 (2003).
Kass, M. et al Snakes: Active contour models. *International Journal of Computer Vision* 1, 321-331 (1988).
Kirkegaard, T. et al. AKT activation predicts outcome in breast cancer patients treated with tamoxifen. *The Journal of pathology* 207, 139-46 (2005).
Kong, A. et al. Prognostic value of an activation state marker for epidermal growth factor receptor in tissue microarrays of head and neck cancer. *Cancer Research* 66, 2834-43 (2006).

König, P. et al . FRET-CLSM and double-labelling indirect immunofluorescence to detect close association of proteins in tissue sections. *Laboratory Investigation* 86, 853-864. (2006).
Li, H.-F. et al Radiation-induced Akt activation modulates radioresistance in human glioblastoma cells. *Radiation oncology (London, England)* 4, 43 (2009).
Magdeldin, S. et al Toward deciphering proteomes of formalin fixed paraffin-embedded (FFPE) tissues. *Proteomics* 12, 1045-58 (2012).
Majewski, J., I. et al Taming the dragon: genomic biomarkers to individualize the treatment of cancer. *Nature Medicine* 17, 304-312 (2011).
Nelson, A. L. Antibody fragments: hope and hype. *mAbs*; 2:1 77-83 (2010).
Ng, T. Imaging Protein Kinase C Activation in Cells. *Science* 283, 2085-2089 (1999).
Pietraszewska-Bogiel, A. et al J. FRET microscopy: from principle to routine technology in cell biology. *Journal of Microscopy* 241,111-8 (2011).
Polyak, K. Heterogeneity in breast cancer. *The Journal of Clinical Investigation* 121, 3786-8 (2011).
Sarbassov D., et al Phosphorylation and regulation of Akt/PKB by the rictor-mTOR complex. *Science* 307, 1098-1101 (2005).
Scheid, M. P. et al PKB/AKT: functional insights from genetic models. *Nature Reviews. Molecular Cell Biology* 2, 760-8 (2001).
Sellers, R. W. Targeting the PI3K pathway in cancer. *Molecular Cancer Therapeutics* (2009) at <http://www.mendeley.com/research/targeting-thepi3k-pathway-in-cancer/>.
Simon, R. et al Immunohistochemical analysis of tissue microarrays. *Methods in Molecular Biology (Clifton, N.J.)* 664, 113-26 (2010).
Stryer, L. Fluorescence Energy Transfer as a Spectroscopic Ruler. *Annual Review of Biochemistry* 47, 819-846 (1978).
Thomas, C. C., et al High-resolution structure of the pleckstrin homology domain of protein kinase b/akt bound to phosphatidylinositol (3,4,5)-trisphosphate. *Current biology: CB* 12, 1256-62 (2002).
Toda, Y. et al Application of tyramide signal amplification system to immunohistochemistry: a potent method to localize antigens that are not detectable by ordinary method. *Pathology International* 49, 479-83 (1999).
Tokunaga et al Akt is frequently activated in HER2/neu-positive breast cancers and associated with poor prognosis among hormone-treated patients. International Journal of Cancer; 118:284-9 (2006).
Vartiainen, M. K et al Nuclear actin regulates dynamic subcellular localization and activity of the SRF cofactor *Science (New York, N.Y.)* 316, 1749-52 (2007).
Vira, S. et al Fluorescent-labeled antibodies—balancing functionality and degree of labeling. *Anal Biochem.* 402(2): 146-150. (2010).
Voss, T. C. et al Quantitative imaging of protein interactions in the cell nucleus. *BioTechniques* 38, 413-24 (2005).
Veeriah, Selvaraju et al., "High-Throughput Time-Resolved FRET Reveals Akt/PKB Activation as a Poor Prognostic Marker in Breast Cancer", Cancer Res; 74(18) 4983-4995 (2014).

* cited by examiner

Correlation between HER2 status and $E_f$ for all cores

Correlation between intensity of HER2 and $E_f$ for all cores

Correlation between intensity of HER3 and E_f for all cores

METHODS FOR DETECTING MOLECULES IN A SAMPLE

DESCRIPTION OF THE INVENTION

The invention relates to methods for detecting molecules in a sample, in particular, protein sites and states in cells, such as those in tissue sections. The invention further provides for the quantification of molecular interactions, such as protein-protein interactions in a sample.

The invention relates to methods using Förster or Fluorescence resonance energy transfer (FRET) in combination with an enzyme activation system, such as tyramide signal amplification (TSA) to improve detection of molecules in a sample, such as protein states and a close spatial association of proteins. More specifically, the invention relates to two-site TSA-FRET methods, where the two sites are on the same protein or on different proteins, such as on a pair of proteins in a complex.

BACKGROUND

The detection of molecules in samples, such as the determination of molecular interactions, in particular protein-protein interactions, is key in many biological fields, particularly cancer biology.

For example, understanding and measuring the molecular diversity underpinning tumour heterogeneity has recently become a major concern, as failure to appreciate this is thought to be one of the reasons for therapeutic failure, particularly in advanced solid tumours.

Intra-tumoural genetic heterogeneity is increasingly well documented in solid cancers, however there is little as yet understood about functional molecular heterogeneity of tumours. The appreciation of this functional heterogeneity has far reaching implications for the development of personalized medicine and improving tumour biopsy methodologies for predictive biomarkers.

For example, breast cancer is heterogeneous at both the histological and molecular levels. A better understanding of breast tumour heterogeneity at the molecular level among a large cohort of patients will help to identify the subtypes to predict outcome, patient response to chemotherapy or targeted therapy.

The assessment of molecular heterogeneity at the protein level has not been extensively reported, in part due to a lack of technologies that can accurately perform this task directly on histological samples. Formalin fixed paraffin embedded (FFPE) tissue sample preparation is the current standard technique by which outpatient and surgical biopsies are processed. Protein biomarkers and their post-translational modifications can be preserved in FFPE archived tumour samples and hence these lend themselves to the accurate quantification of onco-protein functional status and heterogeneity provided the analytical tools and processes are appropriate.

Accurate measurement of the functional status of onco-proteins and tumour heterogeneity at the molecular level may aid the ability to identify subtypes in order to predict outcome, patient response to chemotherapy or targeted therapy.

One well characterized onco-protein, Akt/PKB (protein kinase B) is a member of the AGC family of protein serine/threonine kinases and contains an N-terminal pleckstrin homology (PH) domain which interacts with PtdIns(3,4)P2 and PtdIns(3,4,5)P3. In cancer, Akt plays a central role in cell proliferation and survival, glucose metabolism, genome stability, and neo-vascularization. Akt also contributes to tumour invasion and metastatic spread by induction of epithelial-mesenchymal transition (EMT). Dysregulation of Akt signaling is considered to be a hallmark of many human cancers. In breast cancer, Akt activation occurs in high-grade cases and is correlated with advanced disease, poor prognosis, reduced patient survival, and tumour radioresistance. Various mechanisms contribute to activation of the Akt pathway in human tumours, including disruption of PTEN, up-regulation of phosphoinositide 3-kinase (PI3K) and down-regulation of mTOR (mammalian target of rapamycin). The Akt pathway is also activated by numerous growth factors and cytokines through their cognate receptors. Stimulation of the epidermal growth factor receptor (EGFR) by epidermal growth factor (EGF) leads to activation of Akt in a PI3K-dependent manner. Since Akt activation is both an early event in tumour progression and also a characteristic of many advanced carcinomas, it may represent a useful therapeutic target in both adjuvant and metastatic settings. Therefore, the accurate quantification of its activation state as well as its molecular heterogeneity in patient samples would be highly informative.

At present, research involving detection (and quantification) of molecules, such as endogenous proteins, including onco-proteins in fixed tumour tissue samples, faces several important challenges:
i) the accurate quantification of post-translational modifications, such as phosphorylations, and of protein-protein interactions, such as the interaction of proteins in a complex;
ii) the simultaneous localization of protein in a preserved tissue architecture;

Immunohistochemistry (IHC) is the most readily available method to assess activation of intracellular proteins, such as Akt. However, owing to it being intensity-based, it has several limitations such as lack of standardized scoring, subjectivity in the interpretation of labeled samples, and absence of precise quantification. In addition, it is a "one-site" assay that limits specificity.

FRET makes it possible to measure the interactions (association or dissociation) between two molecules, such as proteins, in close proximity (<10 nm) that are labeled with a pair of fluorescence dyes. A donor fluorescent dye has shorter excitation/emission wavelengths, that excites an acceptor fluorescence dye if the excitation spectrum of the acceptor overlaps with the emission spectrum of the donor. Since the efficiency of energy transfer reduces by the sixth order of magnitude of the distance between the fluorescent dyes, efficient energy transfer generally only occurs between fluorescent pairs that are less than 10 nm apart. Therefore, this approach can be used to detect close spatial association of molecules by labelling them with fluorescent dyes. This approach can also be used to measure protein complex formation as well as conformational changes in molecules, such as conformational and post-translational modification states of individual proteins.

A key limitation of use of FRET for detection of molecules using antibodies is the need to label a pair of antibodies with fluorophores to sufficiently high degrees to achieve adequate signal/noise ratio. Obtaining efficient FRET relies on availability of antibody pairs that are labeled with different fluorophores (either as GFP/mRFP fusion proteins or via chemical conjugation with appropriate fluorescent dyes). This process requires careful optimisation and the labelling of antibodies. Furthermore, current labelling approaches of antibodies give only sufficient signal/noise ratio for their routine use on cell lines in tissue culture—with the target molecule(s) frequently needing to be over-expressed. For tissue sections, in order for there to be sufficient binding specificity, it would be necessary to provide a low protein to dye ratio, which would result in a weak signal that is often undetectable. Hence, use of FRET on tissue sections in particular, is not routine.

In order to perform FRET on tissue sections, "coincidence FRET" or "two-site" FRET can be used. Such method involves simultaneously labelling a single protein on two distinct sites (i.e. the two target sites are on the same protein) with a FRET donor and a FRET acceptor, and detecting the FRET between them. The method has gained recent popularity due to its high specificity and its relative insensitivity to intensity artefacts. However, time resolved FRET methodologies have been limited by low sensitivity due to the requirement for fluorescently labeled primary antibodies. In particular, in order to obtain the high binding specificity, it is necessary to use a low protein to dye ratio, which results in a weak signal. Increased labelling of the antibody results in reduction of the signal to noise ratio and disrupts the antibody binding to the target region.

For example, FRET assays that quantify ectopically expressed proteins tagged with appropriate donor and acceptor pairs of fluorophores such as GFP and monomericRFP (mRFP) are well established. In these cell-based experiments, relatively elevated expression of these GFP and mRFP fusion proteins provides a high signal-to-noise ratio. However, quantifying the activation of endogenous proteins directly in cells using a coincidence FRET assays has been a challenge, partly due to the fact that in order to obtain the high binding specificity, it is necessary to use a low protein to dye ratio, which results in a weak signal.

When chromophores are conjugated to primary antibodies, high average FRET efficiencies are achieved but several limitations are encountered. Firstly, the conjugation process can result in the presence of multiple dye molecules at the antigen recognition site, with adverse consequences on antibody-antigen specificity. Secondly, the signal obtained from primary antibody-chromophore conjugates could not be amplified due to limitations in the dye-to-antibody ratio. This is particularly problematic when protein biomarkers are present in low quantities in tissue samples. Thirdly, cost becomes a limiting factor due to the large amount of primary antibodies required for antibody-chromophore conjugation. This is compounded by the fact that commercially available primary antibody-chromophore conjugates with compatible FRET pairs are often difficult to find. Making primary antibody-chromophore conjugates for use in FRET experiments is equally expensive, time-consuming in the characterization of each pairing and there is the perennial risk of loss of function associated with labelling or denaturation.

Unlabeled primary antibodies have been used in combination with chromophore-conjugated secondary antibodies. These are less preferable to primary antibody-chromophore conjugates because for efficient FRET, it is important to keep the donor and acceptor fluorophores within distances where FRET can occur i.e. less than 10 nm. With the use of primary and secondary antibodies, this can lead to increased distances of the fluorophores, thus diminishing a positive FRET signal and consequently, the signal-to-noise ratio. Such labelling methodologies give only sufficient signal/noise ratio for their routine use on cell lines—with the target molecule(s) frequently needing to be over-expressed. For tissue sections, in order for there to be sufficient binding specificity, it would be necessary to provide a low protein to dye ratio, which would result in a weak signal. This, in combination with the increased distances of the fluorophores that can occur when using primary and secondary antibodies, would result in further weakening of the signal, which often makes the signal undetectable. Hence, use of FRET on tissue sections with primary and secondary antibodies, is also not routine.

König et al. discusses the use of labeled-secondary antibodies in FRET. This article states that whole immunoglobulins as well as Fab fragments can be used as secondary antibodies with unlabeled primary antibodies. However, such methods require careful optimisation.

In other areas of biology, such as standard immunohistochemistry and other one-site methods, signal amplification methods have been used in an attempt improve the signal-to-noise ratio. One such method is tyramide signal amplification (TSA), which amplifies both chromogenic and fluorescent signals in standard immunohistochemistry methods. This methodology is based on the ability of horseradish peroxidase (HRP), in the presence of low concentrations of $H_2O_2$, to convert labeled tyramine-containing substrate into an oxidized, highly reactive free radical (reactive biotinylated tyramide) that can covalently bind to electron rich moieties (such as tyrosine residues) at or near the HRP. However, the dynamics of TSA amplification and the diffusion radius of the resulting reactive species has not been well characterised. As such, TSA amplification methods are predicted to result in non-specific labelling of non-target proteins, thereby creating artefacts that will amplify indefinitely resulting in a non-specific signal.

It was also previously thought that the use of TSA amplification or similar amplification methods in a FRET method would further lead to increased distances of the fluorophores, thus diminishing a positive FRET signal and consequently, the signal-to-noise ratio.

The object of the present invention is to provide an improved method for detecting molecules, particularly protein states in cells, such as in tissue sections.

SUMMARY OF THE INVENTION

The present invention provides a generic, high throughput method that combines FRET with an enzyme activation system, such as a tyramide signal amplification (TSA) system.

According to the present invention, there is provided a method for detecting molecules, employing:
a. at least two primary antibodies, wherein the first primary antibody binds to a first site on a molecule and the second primary antibody binds to a second site on a molecule, wherein the second site is different from the first site and wherein the first and second primary antibodies are immunologically distinct;
b. at least two secondary antibodies, wherein the first secondary antibody is labeled with a fluorescence resonance energy transfer (FRET) donor and binds to the first primary antibody; and the second secondary antibody is conjugated or fused to an enzyme and binds the second primary antibody, wherein the first secondary antibody does not bind the second primary antibody and the second secondary antibody does not bind the first primary antibody;
c. a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme;

wherein the method comprises:
d. contacting a sample with the at least two primary antibodies;
e. contacting the sample with the at least two secondary antibodies;
f. performing a wash step;
g. contacting the sample with the conjugate; and
h. detecting any FRET signal generated by the FRET acceptor.

In some embodiments, the at least two primary antibodies are selected from the group consisting of whole immunoglobulins, antibody or antigen-binding fragments thereof or combinations thereof. In some embodiments, at least one of the secondary antibodies is an antibody or antigen-binding fragment. In particular embodiments, the at least two secondary antibodies are antibody or antigen-binding fragments. In preferred embodiments, the antibody or antigen-binding fragments are Fab fragments, scFv fragments or combinations thereof.

In some embodiments, the FRET donor is selected from the group consisting of ORG 488, GFp, fluorescein, IAEDANS, EDANS, BODIPY FL, ATTO488 and combinations thereof. In some embodiments, the FRET acceptor is selected from the group consisting of ALX 594, mRFP, tetramethylrhodamine, fluorescein, dabcyl, BODIPY FL, QSY 7, QSY 9 and combinations thereof.

In some aspects, the at least one enzyme is selected from the group consisting of oxidoreductases, hydrolases, lyases, transferases, isomerases, and ligases. In certain aspects, the enzyme is selected from the group consisting of peroxidases, oxidases, phosphatases, esterases and glycosidases. In particular aspects, the enzyme is selected from the group consisting of horseradish peroxidase, glucose oxidase, alkaline phosphatase and beta-galactosidase.

In some aspects, the substrate is tyramine.

In some embodiments, the primary antibodies are unlabeled.

In some embodiments, the first primary antibody is a murine antibody and the at least one other primary antibody is a rabbit antibody. In particular embodiments, the first secondary antibody is an anti-murine antibody and the at least one other secondary antibody is an anti-rabbit antibody.

In preferred embodiments, the first primary antibody binds to Akt(pan) and the at least one other primary antibody binds to pAkt(T308) on the Akt 1, Akt 2 or Akt 3 protein.

In some aspects, the method can be used to detect Akt activation in the sample. In certain aspects, the sample is a tumour sample.

In other preferred embodiments, the first primary antibody binds to HER2 and the at least one other primary antibody binds to HER3; or first primary antibody binds to HER3 and the at least one other primary antibody binds to HER2.

In other aspects, the method can be used to detect HER2/HER3 interaction in the sample. In certain aspects, the sample is a tumour sample. In preferred aspects, the sample is a breast tumour sample.

In some aspects of the methods, the at least two primary antibodies are contacted with the sample simultaneously or sequentially to one another.

In some aspects of the methods, the at least two secondary antibodies are contacted with the sample simultaneously or sequentially to one another.

In some aspects of the methods, the at least two primary antibodies are contacted with the sample simultaneously to the at least two secondary antibodies.

In some aspects of the methods, the at least two primary antibodies are contacted with the sample before the at least two secondary antibodies.

In certain aspects of the method, a wash step is performed after the at least two primary antibodies are contacted with the sample and before the at least two secondary antibodies are contacted with the sample.

In some embodiments, the first secondary antibody is directly labeled with a FRET donor.

In some embodiments, the sample is a tissue sample.

In some embodiments, the molecule is a protein.

In some embodiments, the first site and the second site are on the same molecule. In other embodiments, the first site and second site are on different molecules.

In some aspects, the methods further comprise the step of quantifying the interaction between the first site and the second site.

The invention also relates to kits for detecting molecules. According to the present invention, there is provided a kit for detecting molecules, the kit comprising:
i. at least two primary antibodies, wherein the first primary antibody binds to a first site on a molecule and the second primary antibody binds to a second site on a molecule, wherein the second site is different from the first site and wherein the first and second primary antibodies are immunologically distinct;
j. at least two secondary antibodies, wherein the first secondary antibody is labeled with a fluorescence resonance energy transfer (FRET) donor and binds to the first primary antibody; and the second secondary antibody is conjugated or fused to an enzyme and binds the second primary antibody, wherein the first secondary antibody does not bind the second primary antibody and the second secondary antibody does not bind the first primary antibody;
k. a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme.

In some embodiments of the kits, the at least two primary antibodies are selected from the group consisting of whole immunoglobulins, antibody or antigen-binding fragments thereof or combinations thereof.

In some embodiments of the kits, at least one of the secondary antibodies is an antibody or antigen-binding fragment. In particular embodiments of the kits, the at least two secondary antibodies are antibody or antigen-binding fragments. In preferred embodiments, the antibody or antigen-binding fragments are Fab fragments, scFv fragments or combinations thereof.

In some embodiments of the kits, the FRET donor is selected from the group consisting of ORG 488, GFp, fluorescein, IAEDANS, EDANS, BODIPY FL, ATTO488 and combinations thereof.

In some embodiments of the kits, the FRET acceptor is selected from the group consisting of ALX 594, mRFP, tetramethylrhodamine, fluorescein, dabcyl, BODIPY FL, QSY 7, QSY 9 and combinations thereof.

In some embodiments of the kits, the at least one enzyme is selected from the group consisting of oxidoreductases, hydrolases, lyases, transferases, isomerases, and ligases. In certain embodiments of the kits, the enzyme is selected from the group consisting of peroxidases, oxidases, phosphatases, esterases and glycosidases. In particular embodiments of the kits, the enzyme is selected from the group consisting of horseradish peroxidase, glucose oxidase, alkaline phosphatase and beta-galactosidase.

In some embodiments of the kits, the substrate is tyramine.

In some embodiments of the kits, the primary antibodies are unlabeled.

In some embodiments of the kits, the first primary antibody is a murine antibody and the at least one other primary antibody is a rabbit antibody.

In some embodiments of the kits, the first secondary antibody is an anti-murine antibody and the at least one other secondary antibody is an anti-rabbit antibody. In preferred embodiments of the kits, the first primary antibody binds to Akt(pan) and the at least one other primary antibody binds to pAkt(T308) on the Akt 1, Akt 2 or Akt 3 protein. In other preferred embodiments of the kits, the first primary antibody binds to HER2 and the at least one other primary antibody binds to HER3; or first primary antibody binds to HER3 and the at least one other primary antibody binds to HER2.

In some embodiments of the kits, the first secondary antibody is directly labeled with a FRET donor.

The kits of the invention can also be used in aforementioned methods of the invention. The present invention also encompasses methods for detecting molecules using the kits of the invention.

Unless otherwise defined, all technical and scientific terms used herein have the same meaning as commonly understood by one of ordinary skill in the art to which this invention belongs. Methods and materials are described herein for use in the present invention. Other suitable methods and materials known in the art can also be used. The materials, methods and examples are illustrative only and not intended to be limiting. Other features and advantages of the invention will be apparent from the following detailed description and figures, and from the claims.

DESCRIPTION OF DRAWINGS

Non-limiting embodiments of the present invention will now further be described by way of reference to the figures, in which:

In FIG. 3($a$) SKBR3 cells were pretreated with LY294002 (50 μM) for 30 min prior to EGF stimulation (100 ng/ml) for 6 min as indicated. The panels show the intensity and the lifetime map images of the donor alone panAkt (with Fab-ORG488 conjugates) or in presence of the acceptor pT308 (with Fab-HRP conjugates associated with TSA-ALX495). The quantification of the FRET efficiencies is shown as a box and whiskers plot for the donor alone panAkt (top graph: zero FRET efficiency) and for the donor in presence of the acceptor panAkt+pT308 (more than 16% FRET efficiency for EGF stimulation). The increase in average FRET efficiency with EGF was clearly noticeable at the plasma membrane as seen from the lifetime map (blue: long lifetime; red: short lifetime). The quantifications show the means±SEM from at least 20 different cells (***, $p<0.0001$, ns, non-significant).

FIG. 3($b$) shows the same experiment as in FIG. 3($a$) but without TSA amplified acceptor signal (using Fab-ALX495 conjugates as acceptor). The box and whiskers plot represent the mean±SEM of the FRET efficiency of pT308. The data show that the dynamic range of the FRET efficiency data is strongly reduced in absence of TSA amplification of the acceptor intensity. The maximum FRET efficiency upon EGF stimulation was of only 7% (***, $p<0.0001$, ns, non-significant).

FIG. 4 ($a$) shows Intensity images and Lifetime maps of FFPE human breast tumours from three different patients labeled with donor alone (panAkt);

FIG. 4($b$) shows donor in presence of the acceptor (panAkt+pT308) as indicated. The box and whiskers plots present the average FRET efficiency of the donor alone (panAkt) and in presence of the acceptor (panAkt+pT308) from at least 10 different areas of the same tissue sections. The increased FRET efficiency represents the phosphorylation status of endogenous Akt and shows the variability from patient to patient. The average FRET efficiency varies from 3% to 6% (***, $p<0.0001$) in these 3 patients and can be detected with great accuracy using the TSA-FRET signal amplification.

FIG. 4($c$) shows as a control calf intestinal alkaline phosphatase (CIP) was used to verify that the FRET efficiency measured with the TSA-FRET system was really due to the levels of phosphorylation of Akt. The box and whiskers plot shows a highly significant (***, $p<0.0001$) reduction of the FRET efficiency of the panAkt+pT308 signal in the CIP-treated condition, confirming the specificity of the TSA-FRET system.

FIG. 5($a$) shows H&E staining for breast Tumour microarrays (TMA). The TMAs were prepared from breast tumour biopsies obtained from 10 patients. For each patient, 4 cores (circles 1 to 4) were selected from different regions within each biopsy. In total 40 tumour cores (4×10 patients) were spotted on each breast TMA. The lower image shows an expanded view of one core that can be divided in 4 regions of interest (ROI) for further analysis. The panels on the right show 3 different magnifications of the same region of the core.

FIG. 5($b$) shows intensity images and lifetime maps of the TMAs stained with panAkt primary antibody only, followed by the TSA signal amplification labeling (donor alone).

FIG. 5($c$) shows intensity images and lifetime maps of the corresponding TMAs (duplicate of the TMA used for the labeling of the donor alone (b)) stained with panAkt+pT308 primary antibodies, followed by the TSA signal amplification labeling (donor+acceptor). Using in-house developed automated FLIM algorithm, the TMA were mapped for each tumour core position on the donor (panAkt) TMA slide and on the corresponding donor plus acceptor (panAkt+pT308) TMA slide.

FIG. 5($d$)—the graph shows the variability of the FRET efficiency within the 4 cores of the same patient sample. For each core the FRET efficiency was calculated on 4 different ROIs. Each bar presents the maximum value of FRET efficiency of the 4 ROIs.

FIG. 6 shows human colon TMA analysis for high-throughput quantification of activated Akt (pT308) and molecular heterogeneity using TSA-FRET.

FIG. 6(d)—the graph shows the variability of the FRET efficiency within the 4 cores of the same patient sample. For each core the FRET efficiency was calculated on 4 different ROIs. Each bar presents the maximum value of FRET efficiency of the 4 ROIs (sectors).

FIG. 6(e)—the data presents the mean±SEM of the average FRET efficiency of the 4 cores from the same patient.

FIG. 7 shows human breast TMA analysis for high-throughput quantification of activated Akt using two-site TSA-FRET.

FRET efficiencies are shown as box and whiskers plots representing mean±SEM for at least 10 different regions from the same tissue section (****, p<0.0001).

Figure 12A:
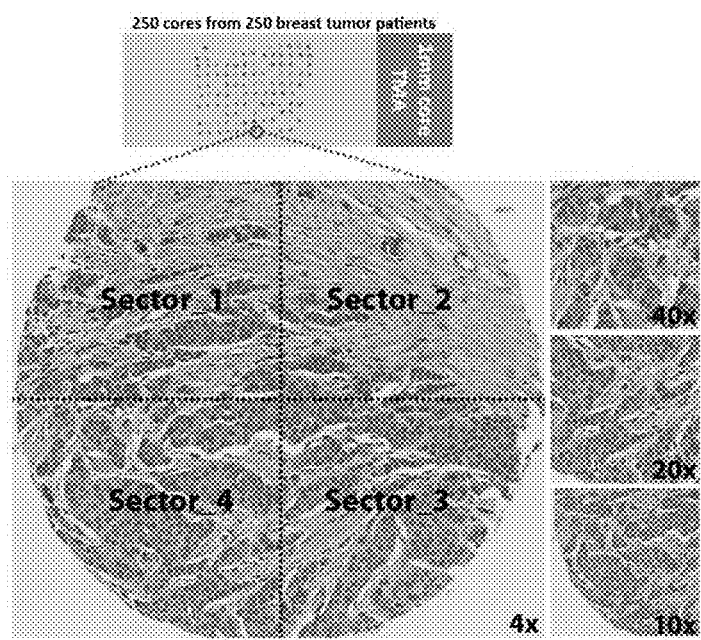
Figure 12B:
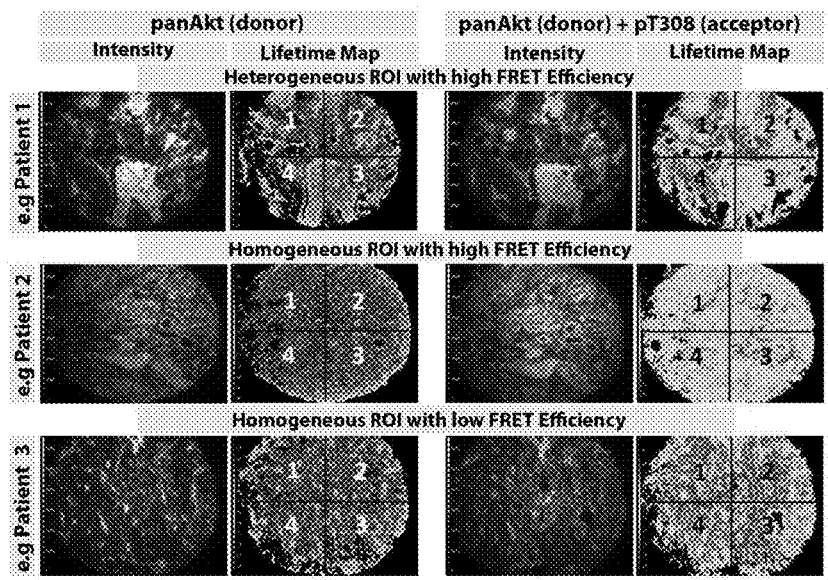
Figure 12B:
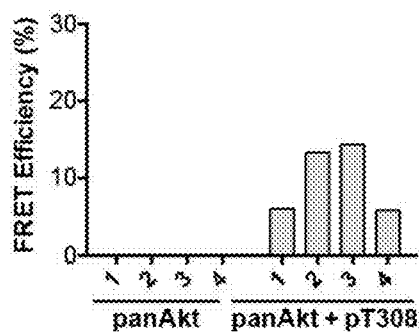
Figure 12B:
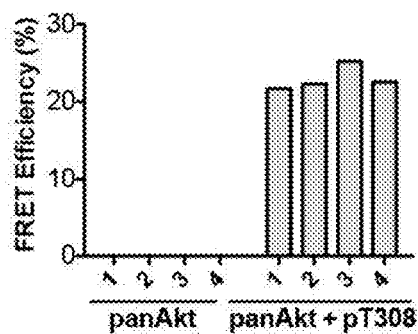
Figure 12B:
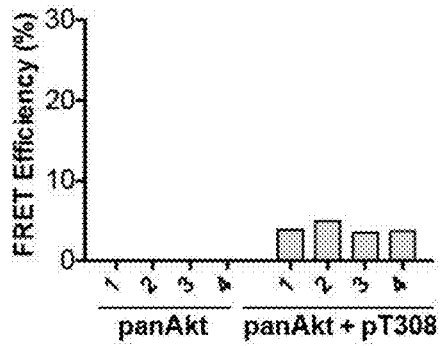
Figure 12C:
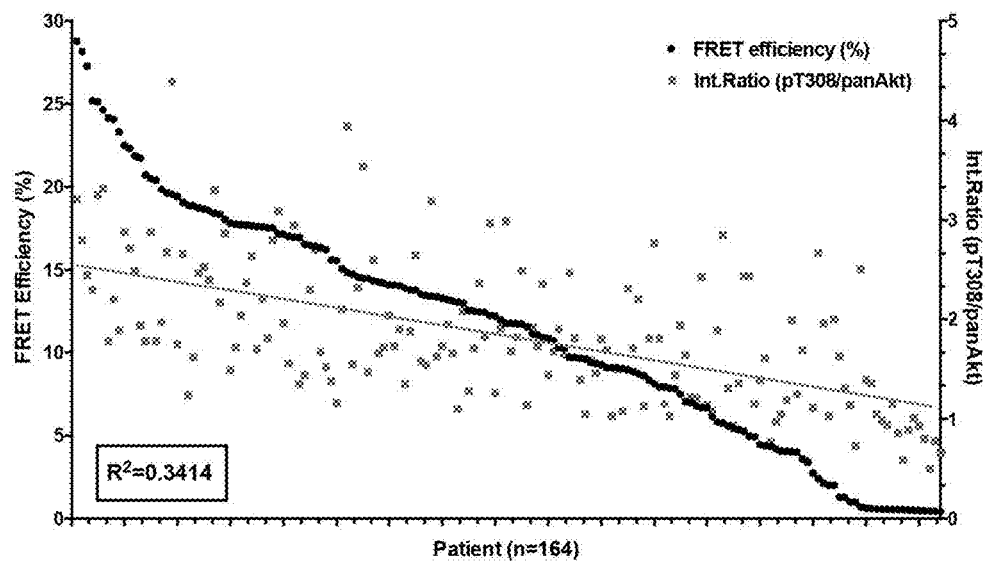

FIGS. 12(a) to (c) show high-throughput quantification of Akt activation in human breast TMA using amplified FRET/FLIM.

FIG. 12(a) shows staining of breast TMAs prepared from breast tumour biopsies obtained from 230 patients. Each core is a representative tissue sample from a single patient. The lower image shows an expanded view of one core divided into 4 sectors for further analysis. The panels on the right show 3 different magnifications of sector 4.

FIG. 12(b) shows intensity images and lifetime maps of the TMAs stained with donor alone (panAkt) donor+acceptor (panAkt+pT308), followed by TSA amplification. TMAs were mapped and images automatically acquired using our FRET/FLIM platform. The three graphs present the FRET efficiency of each sector of the same patient core, for 3 representative patients.

FIG. 12(c)—patients were ordered by descending FRET efficiency. For each patient we plotted the FRET efficiency (black dots, left Y-axis) and the intensity ratio (gray dots, right Y-axis). The regression line for the intensity ratio (gray line, $R^2$=0.3414) is shown for comparison with FRET efficiency.

Figure 13A:
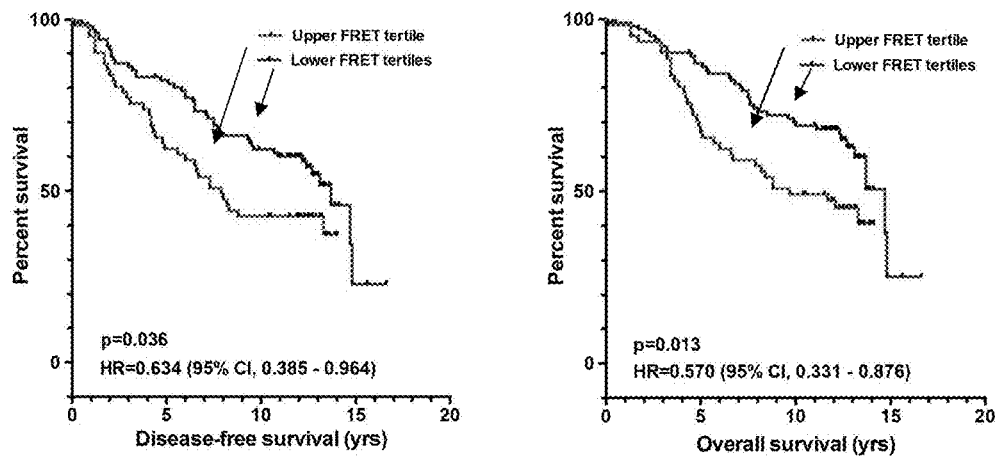

FIGS. 13(a) and (b) show Kaplan-Meier survival curves for all breast carcinoma patients (ER−/ER+) comparing high and low Akt activation.

FIG. 13(a) shows Kaplan-Meier survival plots demonstrating disease-free (left graph) and overall survival of patients (right graph) with high Akt activation (upper tertile, red) or low Akt activation (lower tertiles, blue) as determined by amplified FRET. Results of log rank tests are shown.

Figure 13B:
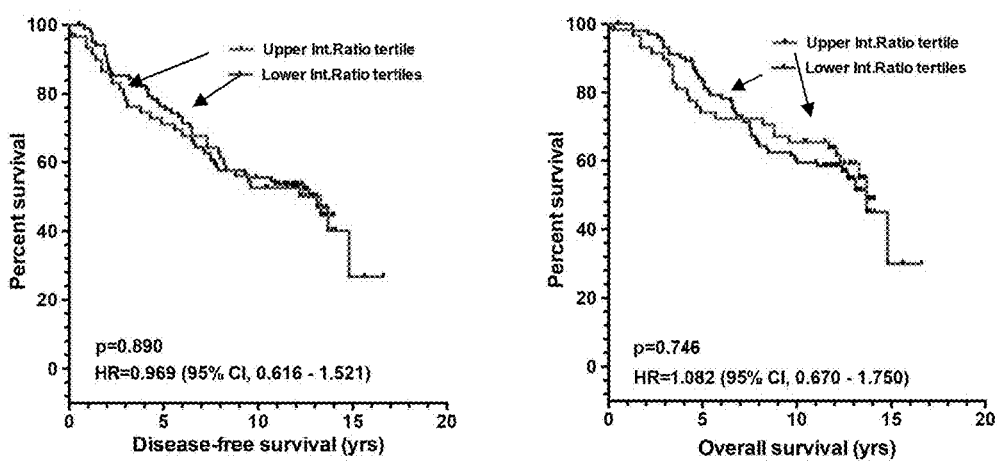

FIG. 13(b) shows the corresponding results when Akt activation is assessed by intensity ratio (calculated as pT308 divided by panAkt intensity).

Figure 13C:
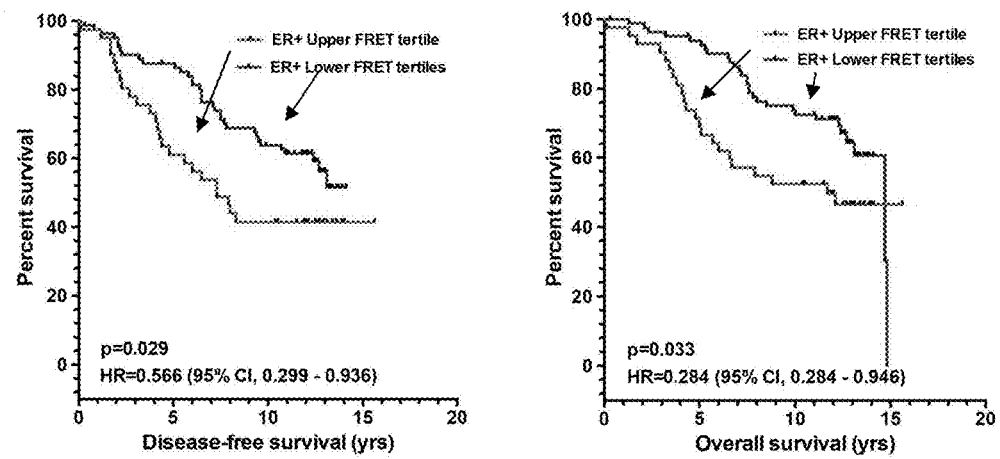

FIGS. 13(c) and (d) show Kaplan-Meier survival curves comparing high and low Akt activation for ER+ breast carcinoma patients.

FIG. 13(c) shows Kaplan-Meier survival plots demonstrating disease-free (left graph) and overall survival of patients (right graph) with high Akt activation (upper tertile, red) or low Akt activation (lower tertiles, blue) as determined by amplified FRET. Results of log rank tests are shown.

Figure 13D:
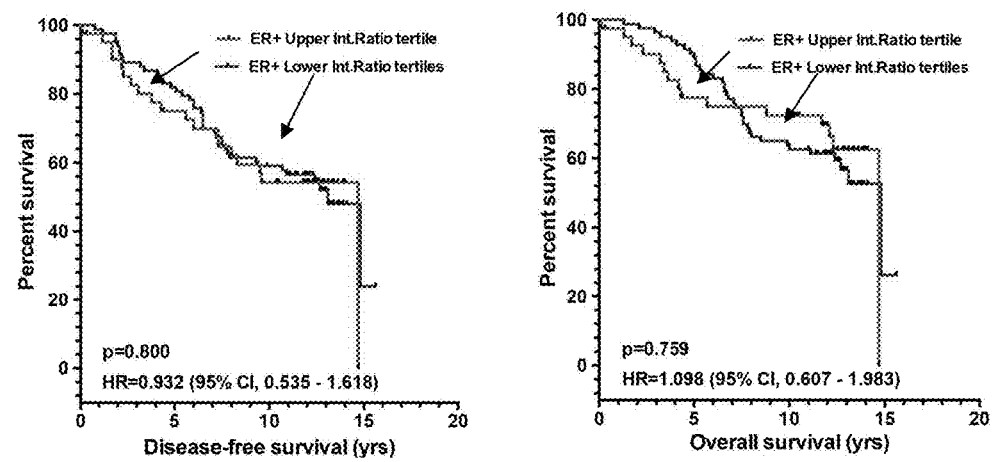

FIG. 13(d) shows the corresponding results when Akt activation is assessed by intensity ratio (calculated as pT308 divided by panAkt intensity).

FIGS. 13(e) to (h) show distribution of Akt activation revealed by amplified FRET for all breast carcinoma patients (ER−/ER+).

Figure 13E:
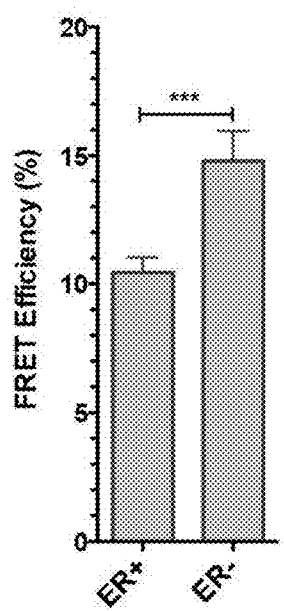

FIG. 13(e) shows the mean FRET efficiency for the patients grouped by ER status (***, p<0.0001).

Figure 13F:
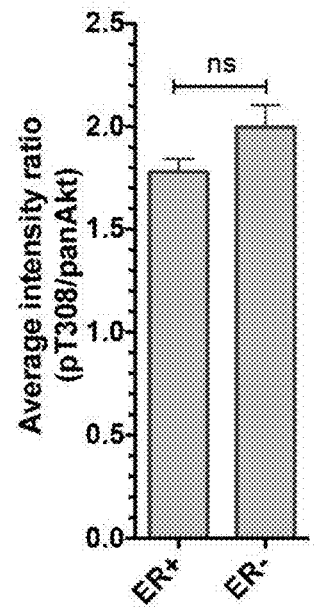

FIG. 13(f) shows the mean intensity ratio for the patients grouped by ER status (ns, not significant).

Figure 13G:
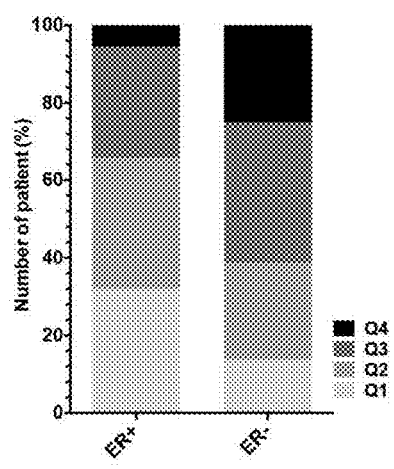

FIG. 13(g) shows the population distribution of patients according to FRET quartiles, grouped by ER status (black, high FRET quartile; light gray, low FRET quartile).

Figure 13H:
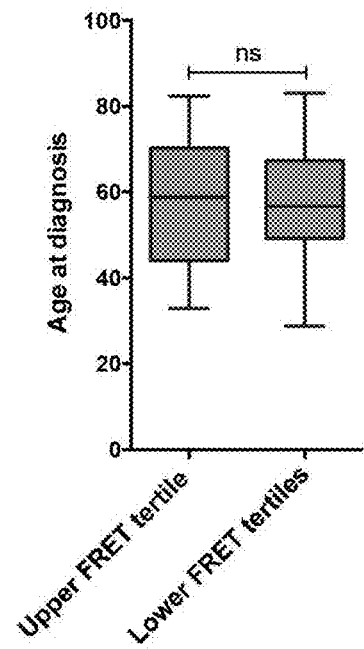

FIG. 13(h)—FRET efficiencies are shown as box and whiskers plots representing the age distribution of patients according to FRET tertiles (ns, not significant).

Figure 14A:
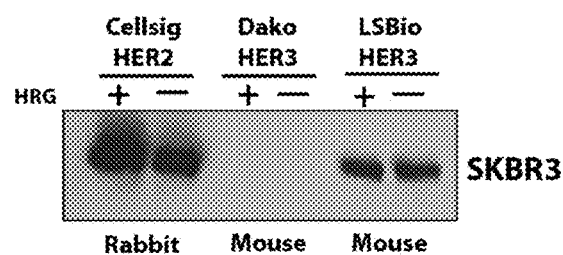

FIG. 14(a) shows the results of the Western blot analysis using Cellsig, Dako and LSBio. HER2/HER3 interaction was measured using a Fab fragment based Tyramide Signal Amplification (TSA) assay.

Figure 14B:
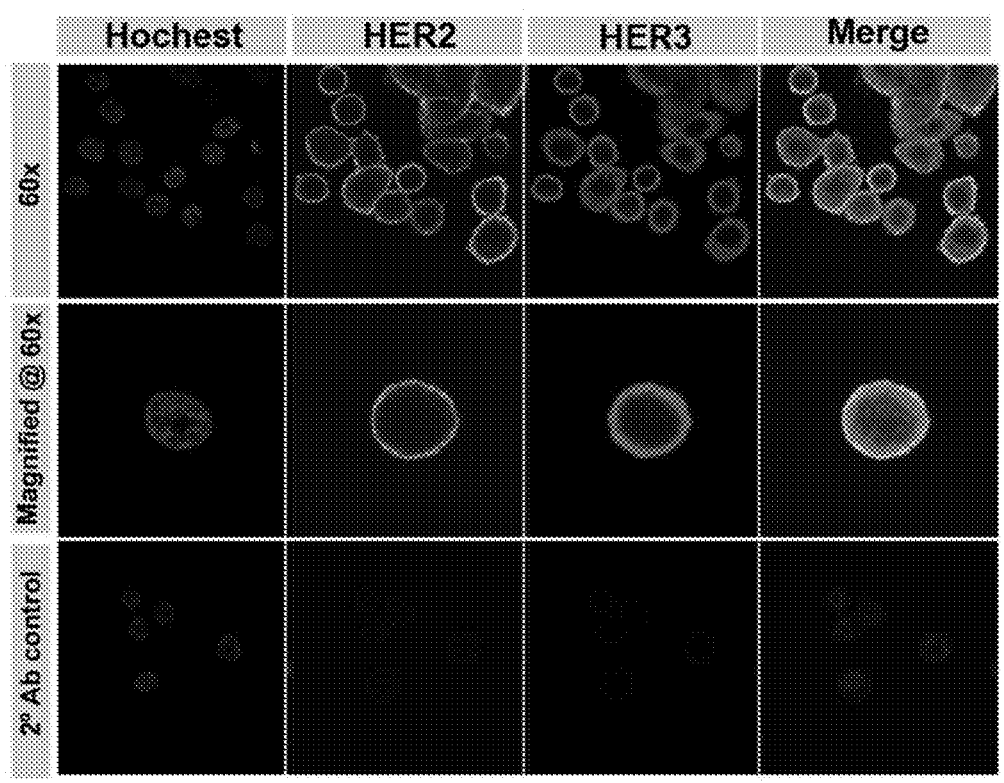

FIG. 14(b) shows confocal microscopy results where co-localisation of endogenous HER2 and HER3 was measured in non-stimulated SKBR3 cells.

Figure 14C:
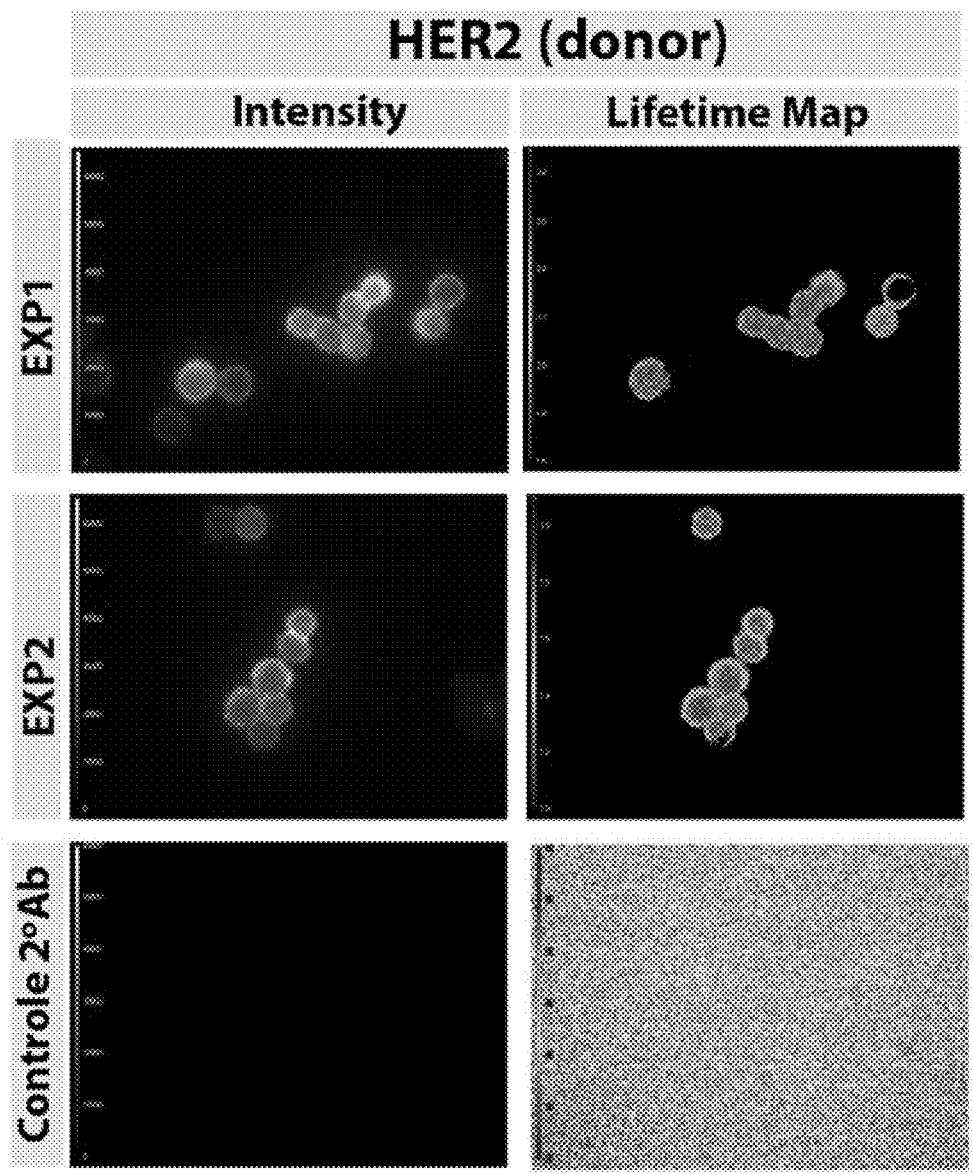
Figure 14D:
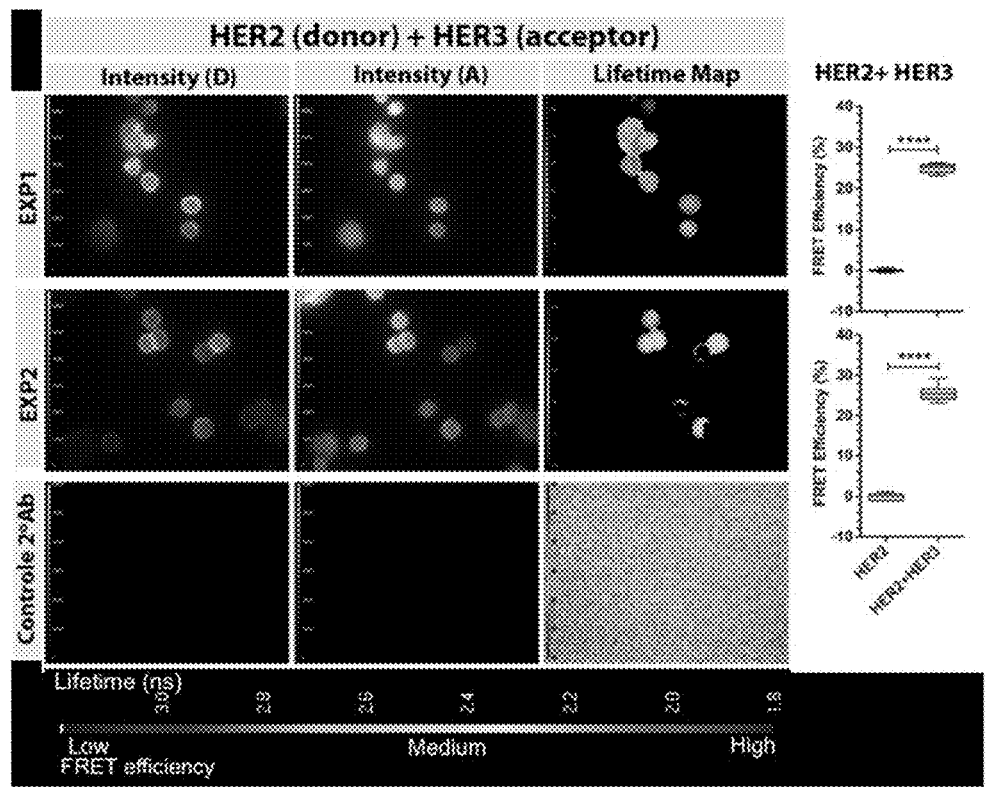

FIGS. 14(c) and (d) show the detection of endogenous HER2-HER3 dimerization in SKBR3 cells. Non-stimulated SKBR3 cells were fixed and stained with HER2 and HER3 antibodies.

Figure 14E:
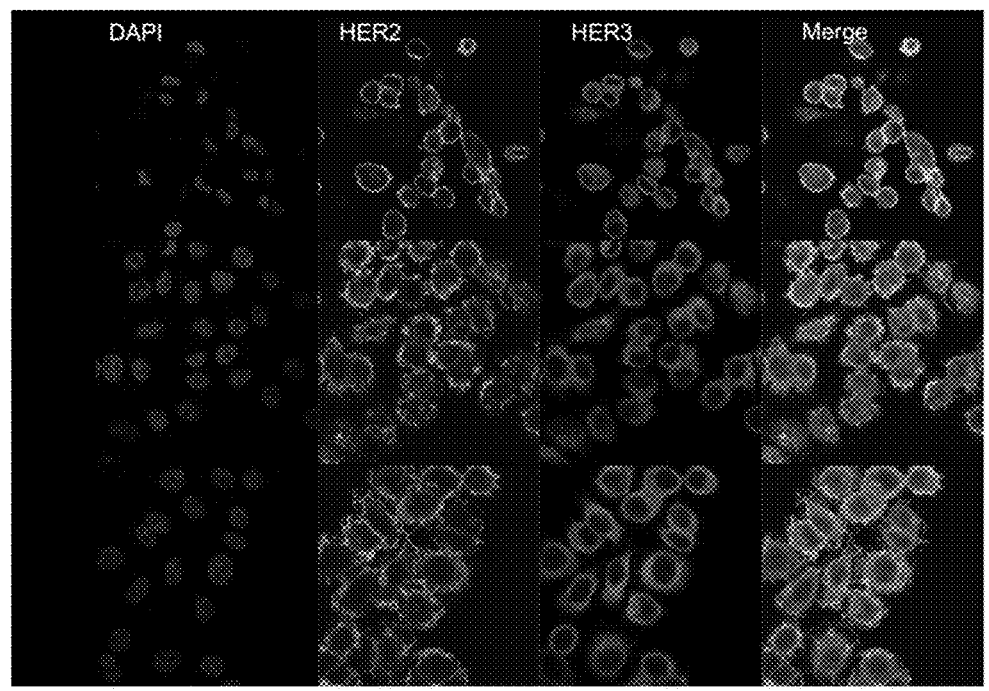

FIG. 14(e) shows confocal image results from the determination of the co-localisation of endogenous HER2 and HER3 in SKBR3 cells stimulated with NRG1 compared to unstimulated SKBR3 cells.

Figure 14F:
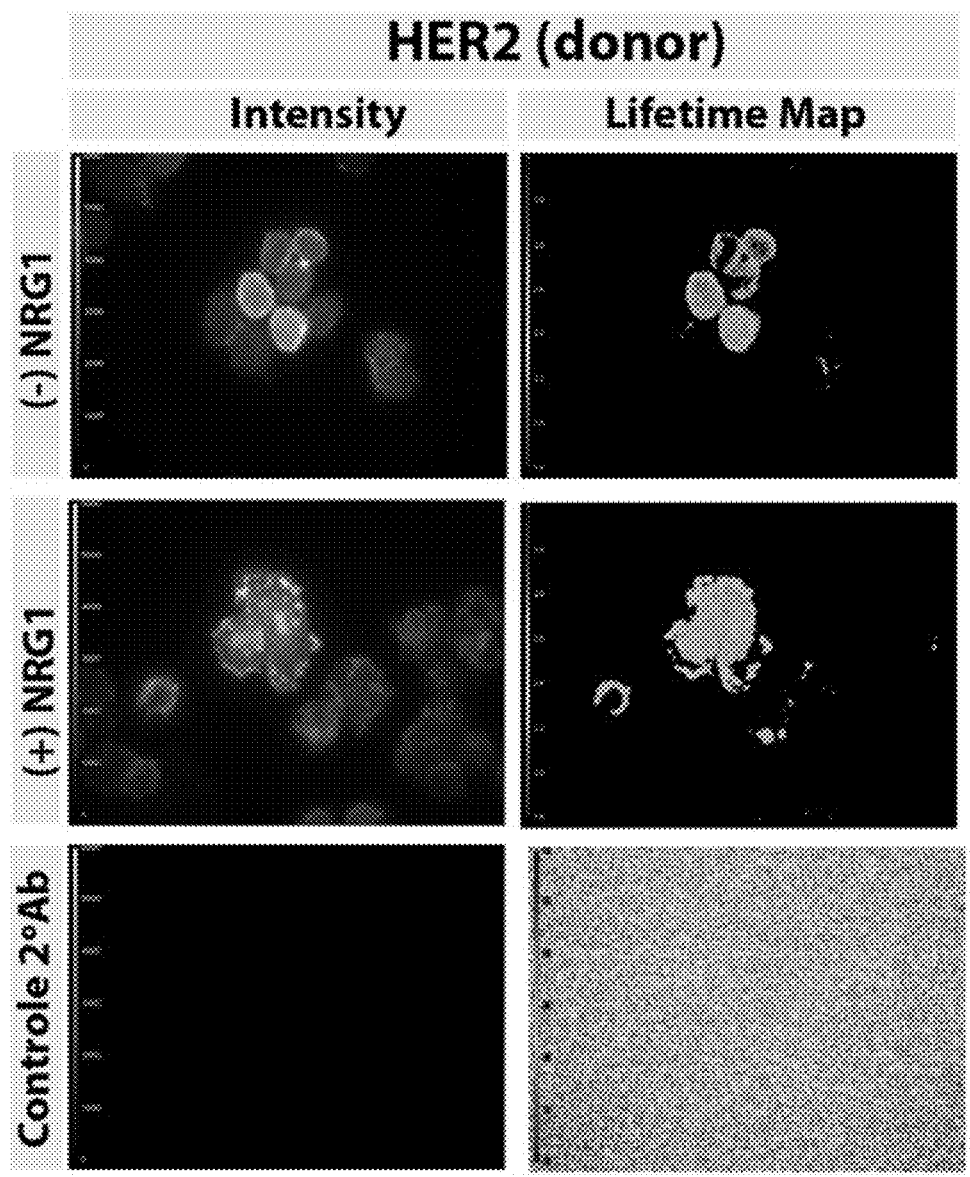
Figure 14G:
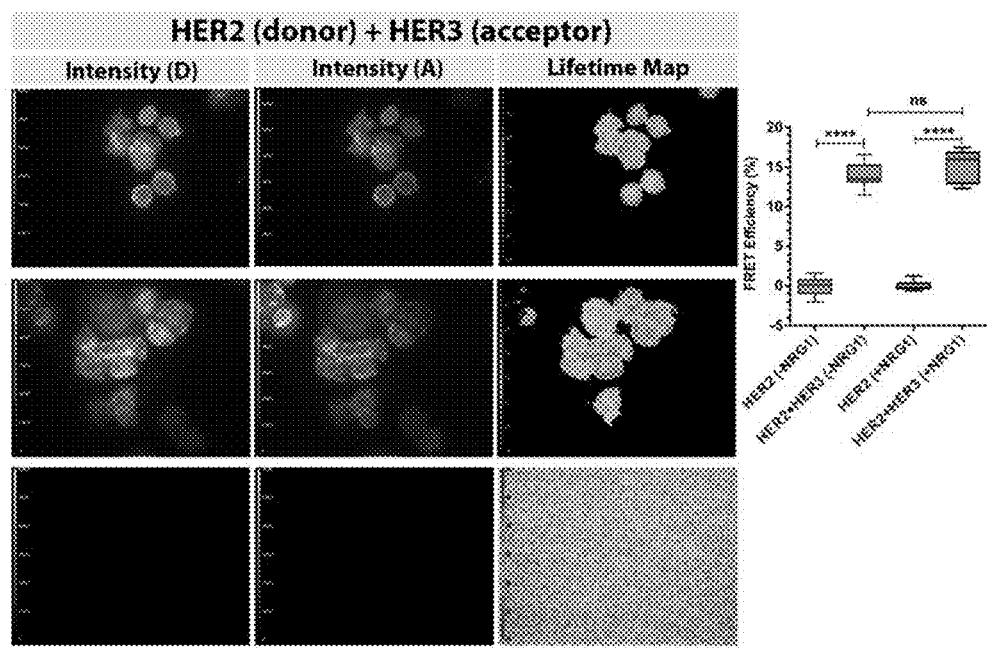

FIGS. 14(f) and (g) show the FRET efficiency ($E_f$) results from the determination of the co-localisation of endogenous HER2 and HER3 in SKBR3 cells stimulated with NRG1 compared to unstimulated SKBR3 cells, for D alone and DA using FRET-FLIM analysis.

Figure 14H:
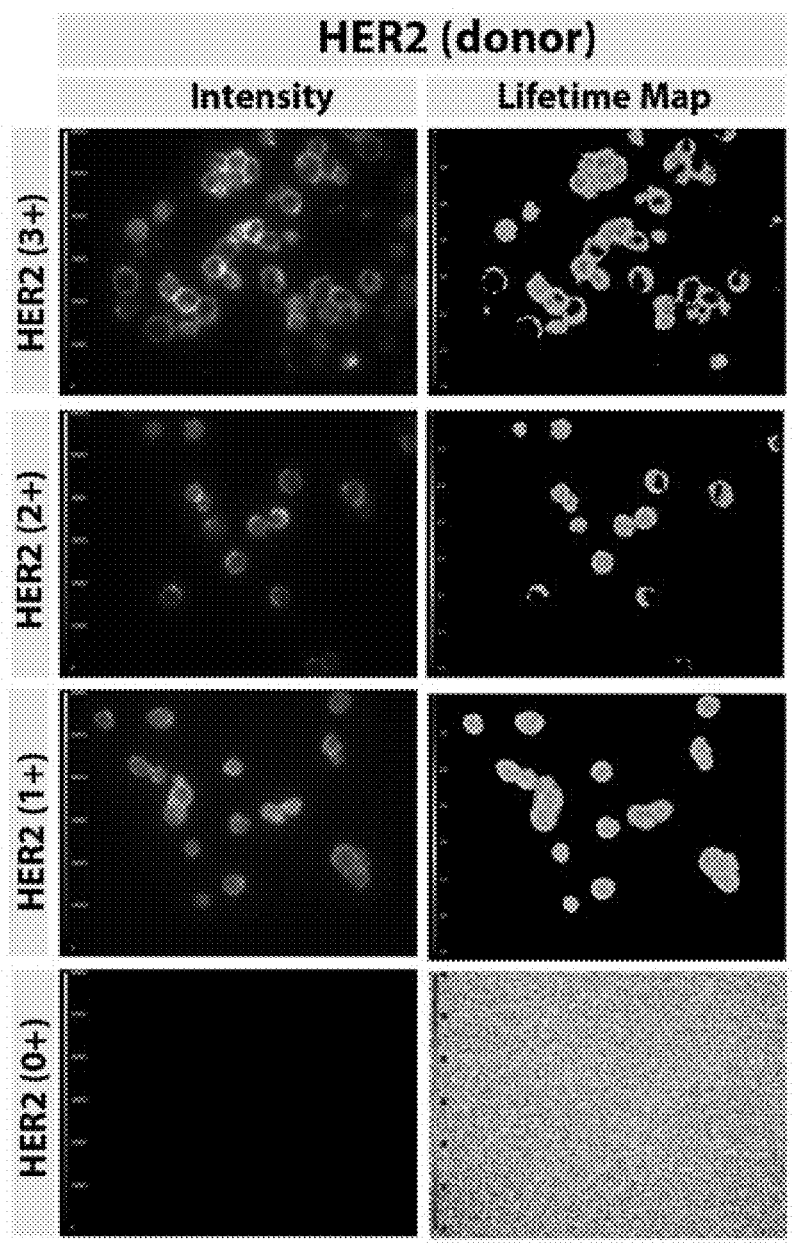

FIGS. 14(h) and (i) show the measurement of HER2-HER3 dimerization in HER2 control slides using the amplified FRET methods of the present invention. The Figures show the FRET efficiency ($E_f$) using FRET-FLIM analysis.

Figure 15A:
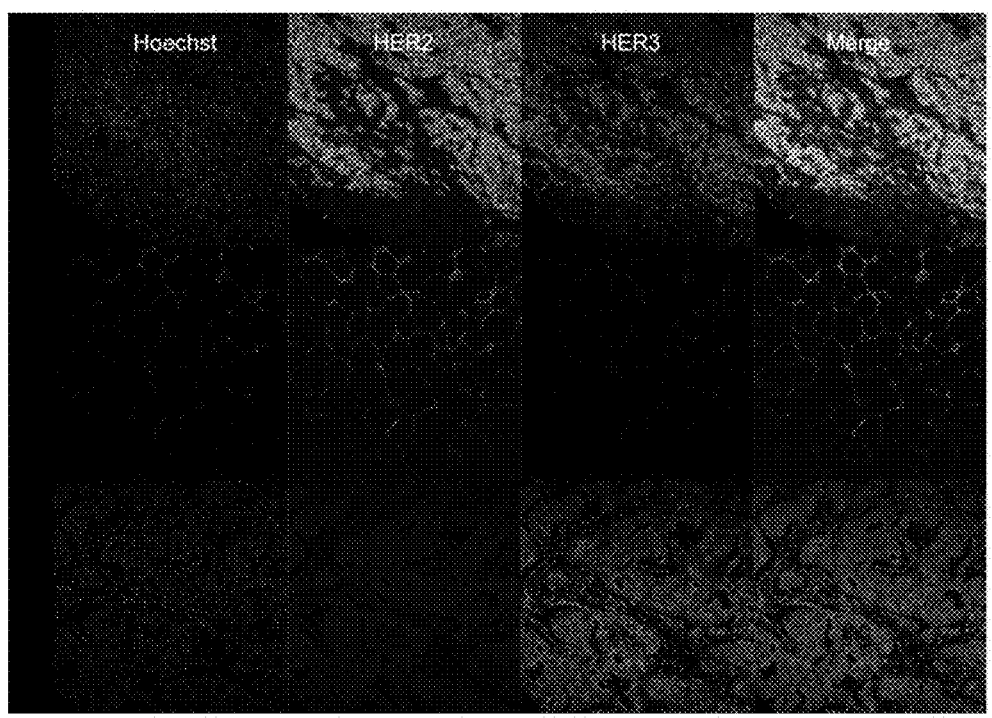

FIG. 15(a) show confocal image results from the detection of co-localization of endogenous HER2-HER3 in human breast tissue (TMA BRC961 was obtained from US Biomax).

Figure 15B:
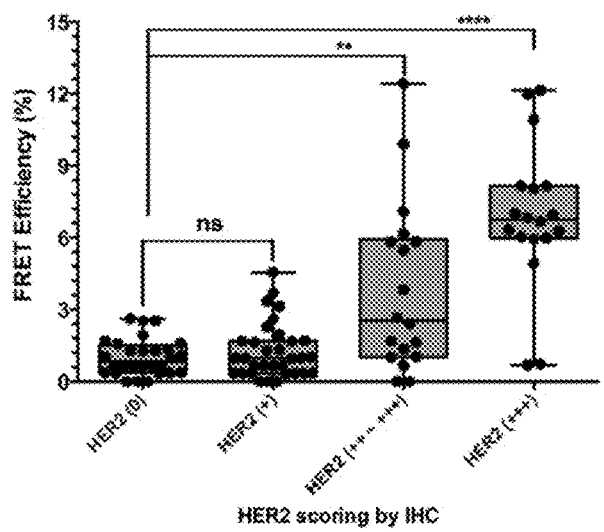
Figure 15C:
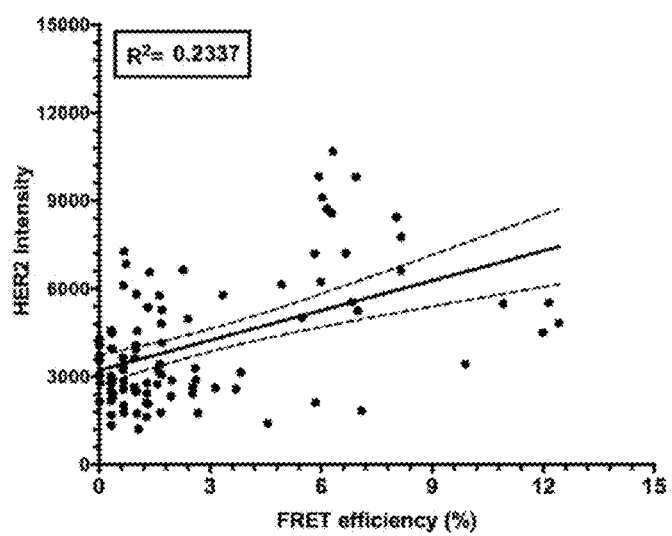
Figure 15D:
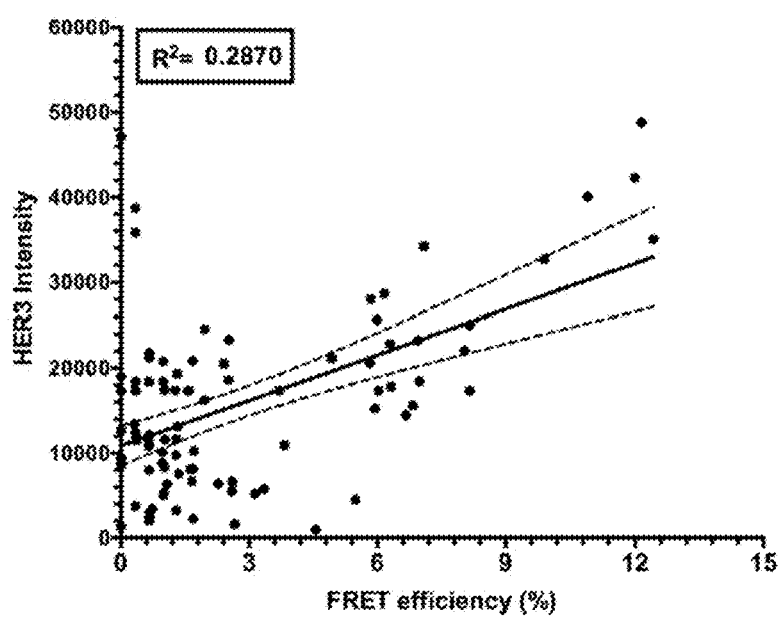

FIGS. 15(b) to (d) show graphs of the FRET efficiency results from the detection of co-localization of endogenous HER2-HER3 in human breast tissue (TMA BRC961 was obtained from US Biomax).

Figure 16:
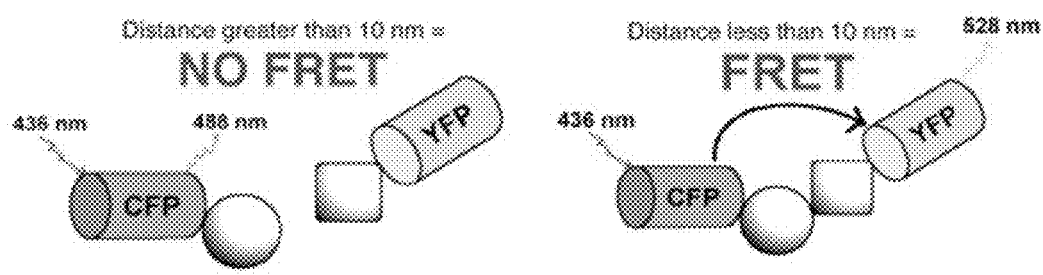

FIG. 16 shows the principles of FRET.

DETAILED DESCRIPTION OF THE INVENTION

The present invention provides a generic, high throughput method that combines the spatio-temporal and quantitative attributes of time resolved FRET detected by multiple frequency domain FLIM (mFD-FLIM) with the sensitivity of an enzyme activation system, such as a tyramide signal amplification (TSA) system, which acts to amplify the signal.

In one aspect, there is provided a method for detecting molecules, employing:
 a. at least two primary antibodies, wherein the first primary antibody binds to a first site on a molecule and the second primary antibody binds to a second site on a molecule, wherein the second site is different from the first site and wherein the first and second primary antibodies are immunologically distinct;
 b. at least two secondary antibodies, wherein the first secondary antibody is labeled with a fluorescence resonance energy transfer (FRET) donor and binds to the first primary antibody; and the second secondary antibody is conjugated to an enzyme and binds the second primary antibody, wherein the first secondary antibody does not bind the second primary antibody and the second secondary antibody does not bind the first primary antibody;
 c. a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme;

wherein the method comprises:
 d. contacting a sample with the at least two primary antibodies;
 e. contacting the sample with the at least two secondary antibodies;
 f. performing a wash step;
 g. contacting the sample with the conjugate; and
 h. detecting any FRET signal generated by the FRET acceptor.

In some aspects, the methods of the invention can be used to detect the activation of an onco-protein (PKB/Akt), in breast and colon tumours. In certain aspects, the resulting resolution evidences molecular heterogeneity within tumours.

In some aspects, the methods of the invention can be used to detect protein-protein interactions, such as HER2/HER3 interactions. The sample used to detect the protein-protein interactions can be a cell sample or a tissue sample. The tissue sample can be a breast tissue sample.

In a preferred embodiment, the methods of the invention are used to detect HER2/HER3 interactions in a breast tissue sample, such as a breast tumour sample. In certain aspects, the methods of the invention can be used to determine whether or not a disease state exists in the tissue sample, such as the presence of a tumour.

In some aspects, the methods of the invention can be used to inform on prognostic, predictive and diagnostic markers.

The methods of the invention can be automated. In one embodiment, the automated methods utilise mFD-FLIM. In preferred embodiments, the automated methods can be used with two-site TSA-FRET. In some embodiments, the automated methods can be used to detect the activation of an onco-protein, for example, in breast and colon tumours. In one embodiment, automated mFD-FLIM can be used in combination with two-site TSA-FRET to detect the activation of an onco-protein (PKB/Akt), in breast and colon tumours with a resolution that evidences molecular heterogeneity within tumours.

The invention also relates to kits for detecting molecules. According to the present invention, there is provided a kit for detecting molecules, the kit comprising:
 i. at least two primary antibodies, wherein the first primary antibody binds to a first site on a molecule and the second primary antibody binds to a second site on a molecule, wherein the second site is different from the first site and wherein the first and second primary antibodies are immunologically distinct;

j. at least two secondary antibodies, wherein the first secondary antibody is labeled with a fluorescence resonance energy transfer (FRET) donor and binds to the first primary antibody; and the second secondary antibody is conjugated to an enzyme and binds the second primary antibody, wherein the first secondary antibody does not bind the second primary antibody and the second secondary antibody does not bind the first primary antibody;

k. a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme.

The methods of the invention have the advantage of providing a low cost, generic and robust high throughput methodology with an improved signal/noise ratio.

The novel methods of the invention can, in particular, be used to address the challenges of fundamental and translational proteomic research in human pathologies including cancer.

Definitions

"Enzyme activation system" refers to an enzyme system where at least one enzyme is coupled, in any manner known to a person of skill in the art, to a member of a specific binding pair. For example, the enzyme can be conjugated or fused to the specific binding pair. In the present invention, the specific binding pair can be located on an antibody. In certain embodiments, the specific binding pair is located on an antibody selected from the first primary antibody, the second primary antibody, the first secondary antibody and the second secondary antibody and combinations thereof.

The enzyme, either by itself of or in connection with a second enzyme reacts with a conjugate comprising a detectably-labeled substrate, to form an activated conjugate. The activated conjugate binds to a receptor (e.g. electron rich moieties) on a molecular surface adjacent to the enzyme. The binding can be via covalent binding. The activated conjugate can be deposited wherever receptors (e.g. electron rich moieties) for the activated conjugate are found. The receptors (e.g. electron rich moieties) on the molecular surface are not reactive with the enzyme activation system. Therefore, the detectably-labeled substrate binds the receptors (e.g. electron rich moieties) only when the detectably-labeled substrate has been activated by the enzyme to form an activated conjugate. In the absence of the enzyme, the detectably-labeled substrate does not form an activated conjugate.

The detectably-labeled substrate of the conjugate can comprise one or more components. In one embodiment, the detectably-labeled substrate comprises one component containing the binding site for the receptor (e.g. electron rich moieties) and a detectable-label. In another embodiment, the substrate comprises two components; one component can contain the binding site for the receptor (e.g. electron rich moieties) and be detectably labeled. The other component can contain a constituent which prevents or interferes with binding to the receptors (e.g. electron rich moieties) until such a time as the enzyme activates the conjugate.

The term "detectably-labeled" means that the substrate is coupled either directly to a detectable label or indirectly to a detectable label.

The substrate can be detectably labeled using methods well known to a person of ordinary skill in the art.

In the case of indirect labelling, the substrate can be coupled to an unlabeled first member of a specific binding pair. Following activation and binding to the receptor (e.g. electron rich moieties) by the activated conjugate, the first member of the specific binding pair can be reacted with the second member of the specific binding pair, which is coupled to a detectable label. Alternatively, the first member of the specific binding pair can be pre-reacted with the second member of the specific binding pair, which is coupled to a reporter, prior to activation and binding of the receptor (e.g. electron rich moieties) by the activated conjugate.

In the present invention, the detectable label comprises a FRET acceptor or a FRET donor. In preferred embodiments, the detectable label comprises a FRET acceptor. In some aspects of the present invention, the substrate comprises tyramide. In some embodiments, the detectably labeled substrate comprises tyramide labeled with a FRET donor. In preferred embodiments, the detectably labeled substrate comprises tyramide labeled with a FRET acceptor.

The enzyme can be selected from oxidoreductases, hydrolases, lyases, transferases, isomerases, ligases and combinations thereof. In certain embodiments, the enzyme is selected from peroxidases, oxidases, phosphatases, esterases, glycosidases and combinations thereof. In preferred embodiments, the enzyme is selected from horseradish peroxidase, glucose oxidase, alkaline phosphatase, beta-galactosidase and combinations thereof.

The term "activated conjugate" refers to a conjugate comprising a detectably labeled substrate that is specific for the enzyme activation system and has been activated by the enzyme of the system. Following activation, the activated conjugate can bind the receptors (e.g. electron rich moieties) on a molecular surface adjacent to the enzyme. A sample is subjected to reaction conditions sufficient to cause the enzyme to catalyse the activation of the substrate in order to form the activated conjugate.

The reaction conditions sufficient to cause the enzyme to catalyse the activation of the substrate are well known to a person of skill in the art. In the case of tyramide signal amplification (TSA), the enzyme employed is hydrogen peroxidase and the detectably-labeled substrate is detectably-labeled tyramide. The reactions conditions require the presence of hydrogen peroxide for hydrogen peroxidase to catalyse the activation of detectably-labeled tryramide to form an activated conjugate containing detectably-labeled tyramide radicals. In preferred embodiments, the detectable label is a FRET acceptor or a FRET donor. In particularly preferred embodiments, the detectable label is ALX594 or ORG488. In other preferred embodiments, the detectable label is ALX594 or ATTO488.

In preferred embodiments, the detectably-labeled substrate comprises tyramide labeled with a FRET acceptor and the enzyme (e.g. horseradish peroxidase) activates tyramide to form an activated conjugate comprising highly reactive, short-lived tyramide radicals coupled to the FRET acceptor, which radicals can covalently couple to electron rich moieties on a molecular surface adjacent to the enzyme. In preferred embodiments, the electron rich residues are tyrosine residues. The molecular surface can be a protein or nucleic acid sequence.

The term "amplification" refers to amplification of a reporter signal provided by the detectable label of the detectably-labeled substrate due to binding of conjugates comprising the detectably-labeled substrate that have been activated by the enzyme activation system to electron rich moieties on a molecular surface adjacent to the enzyme. In the present invention, the reporter signal can comprise fluorescence. In some embodiments, the reported signal comprises fluorescence emitted by a FRET acceptor or a FRET donor. In preferred embodiments, the reporter signal comprises fluorescence emitted by a FRET acceptor.

The enzyme activation system of the present invention can be applied to the first primary antibody, the second primary antibody, the first secondary antibody, the second secondary antibody or a combination thereof, provided that the system is applied to at least one of the first secondary antibody and the second secondary antibody.

"Adjacent to" in the context of the enzyme activation system refers to receptors located within close proximity to the enzyme. For example, the distance between the enzyme and receptors can be about 2 to 9 nm or less than 100 kDa (preferably, 2 to 9 nm, 2 to 7 nm, 2 to 6 nm, 2 to 5 nm, 2 to 4 nm or 2 to 3 nm or less than 90 kDa, less than 80 kDa, less than 70 kDa, less than 60 kDa, less than 50 kDa, less than 40 kDa, less than 30 kDa, less than 20 kDa or less than 10 kDa).

One specific embodiment of a single enzyme activation system of the present invention is a tyramide signal amplification (TSA) system. The system utilises the catalytic activity of horseradish peroxididase, which activates reporter-coupled tyramide to form an activated conjugate comprising highly reactive, short-lived tyramide radicals, which radicals can covalently couple to tyrosine residues on a molecular surface adjacent to the horseradish peroxidase. The molecular surface can be a protein or nucleic acid residue.

"Fluorescence (or Förster) Resonance Energy Transfer (FRET)" is a photophysical process in which energy is transferred from an excited FRET (donor) fluorophore to an adjacent FRET (acceptor) fluorophore via a non-radiative dipole-dipole interaction. The efficiency of energy transfer varies inversely with the sixth power of the distance, separating donor and acceptor fluorophores hence the distance over which FRET can occur is limited to 9 nm. Therefore, FRET is a "chemical ruler" used to measure molecular proximity.

FIG. 16 shows the principles of FRET.

FRET makes it possible to measure the interactions (association or dissociation) between two proteins in close proximity (<10 nm) that are labeled with a pair of fluorescence dyes.

"FRET donor" refers to a chromogenic or fluorogenic substrate that has shorter excitation/emission wavelengths than a FRET acceptor. In the above Figure, the FRET donor is cyan fluorescent protein (CFP).

"FRET acceptor" refers to a chromogenic or fluorogenic substrate that has longer excitation/emission wavelengths than a FRET donor. In the above Figure, the FRET acceptor is yellow fluorescent protein (YFP).

The donor chromophore (FRET donor) excites the acceptor molecule (FRET acceptor) when the emission spectrum of the donor and the excitation spectrum of the acceptor overlap. The FRET donor and FRET acceptor molecules need to be in close proximity (less than 10 nm). When the distance between the donor and acceptor is less than 10 nm, excitation of the acceptor occurs, providing a measurable fluorescent reporter signal. As well as detecting the reporter signal, it is possible to quantify the reporter signal. This approach can be used to determine the distance between the donor and acceptor chromophores. This approach can also be used to measure protein-protein interactions, protein-lipid interactions, protein-DNA interactions, and protein confor-mational changes, such as conformational and post-translational modification states of individual proteins.

The FRET efficiency (E)(E) is the quantum yield of the energy transfer transition, i.e. the fraction of energy transfer event occurring per FRET donor excitation event:

$$E = \frac{k_{ET}}{k_f + k_{ET} + \sum k_i}$$

$$E = \frac{k_{ET}}{k_f + k_{ET} + \sum k_i}$$

where $k_{ET}k_{ET}$ is the rate of energy transfer, $k_f k_f$ the radiative decay rate and the $k_i k_i$ are the rate constants of any other de-excitation pathway.

The FRET efficiency depends on many physical parameters, including the distance between the donor and the acceptor, the spectral overlap of the FRET donor emission spectrum and the FRET acceptor absorption spectrum and the relative orientation of the FRET donor emission dipole moment and the FRET acceptor absorption dipole moment.

EE depends on the FRET donor-to-FRET acceptor separation distance rr with an inverse 6th power law due to the dipole-dipole coupling mechanism:

$$E = \frac{1}{1 + (r/R_0)^6}$$

$$E = \frac{1}{1 + (r/R_0)^6}$$

with $R_0 R_0$ being the Förster distance of this pair of FRET donor and FRET acceptor. This is the distance at which the energy transfer efficiency is about 50%.

The Förster distance depends on the overlap integral of the FRET donor emission spectrum with the FRET acceptor absorption spectrum and their mutual molecular orientation as expressed by the following equation:

$$R_0^6 = \frac{9Q_0(\ln 10)\kappa^2 J}{128\pi^5 n^4 N_A}$$

$$R_0^6 = \frac{9Q_0(\ln 10)\kappa^2 J}{128\pi^5 n^4 N_A}$$

where $Q_0 Q_0$ is the fluorescence quantum yield of the donor in the absence of the FRET acceptor, $\kappa^2$ is the dipole orientation factor, nn, is the refractive index of the medium, $N_A N_A$ is Avogadro's number, and JJ is the spectral overlap integral calculated as $$J = f_D(\lambda)\epsilon_A(\lambda)\lambda_4 d\lambda$$

$$J = f_D(\lambda)\epsilon_A(\lambda)\lambda_4 d\lambda$$

where $f_D f_D$ is the normalized FRET donor emission spectrum, and $\epsilon_A \epsilon_A$ is the FRET acceptor molar extinction coefficient. $\kappa^2 = 2/3$ is often assumed. This value is obtained when both the donor and acceptor are freely rotating and can be considered to be isotropically oriented during the excited state lifetime. If either the donor or acceptor is fixed or not free to rotate, then $\kappa^2 = 2/3$ will not be a valid assumption. In most cases, however, even modest reorientation of the donors and acceptors results in enough orientational averaging that $\kappa^2 = 2/3$ does not result in a large error in the estimated energy transfer distance due to the sixth power dependence of $R_0$ on $\kappa^2$. Even when $\kappa^2$ is quite different from ⅔ the error can be associated with a shift in $R_0$ and thus determinations of changes in relative distance for a particular system are still valid.

The FRET efficiency relates to the quantum yield and the fluorescence lifetime of the donor molecule as follows:

$$E = 1 - \tau'_D/\tau_D$$

$$E = 1 - \tau'_D/\tau_D$$

where and $\tau_D\tau_D$ are the donor fluorescence lifetimes in the presence and absence of a acceptor, respectively, or as $$E = 1 - F'_D/F_D$$

$$E = 1 - F'_D/F_D$$

where $F'_D F'_D$ and $F_D F_D$ are the donor fluorescence intensities with and without an acceptor, respectively.

Donors of the present invention include ORG 488, GFp, fluorescein, IAEDANS, EDANS, BODIPY FL and ATTO488.

Acceptors of the present invention include ALX 594, mRFP, fluorescein, tetramethylrhodamine, dabcyl, BODIPY FL and QSY 7 and QSY 9 dyes.

Combinations of the above donor and acceptor pairs are encompassed by the present invention.

Other exemplary donor—acceptor pairs include cyan fluorescent protein (CFP)—yellow fluorescent protein (YFP), YFP-CFP, ORG488-ALX594 and ATTO488-ALX594.

The donor and acceptor can be of two different types (hetero-FRET) or of the same type (homo-FRET). In the case of homo-FRET, spectral differences are not used to detect and measure FRET. Instead, differences in the anisotropy between the light which excites the donor and acceptor and the light which is emitted can be detected and measured. Exemplary methods for detecting homoFRET include FRET anisotropy imaging. The level of quantified anisotropy (the difference in polarisation between the excitation and emission beams) provides an indication of how many FRET events have occurred.

TABLE 1A

| FRET Donor | FRET Acceptor | $R_0$ (A) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

There are several ways of measuring the FRET efficiency by monitoring changes in the fluorescence emitted by the donor or the acceptor. These methods are well known to a person of skill in the art, such as sensitised emission, photobleaching FRET and lifetime measurements, and are encompassed with the present invention.

Exemplary uses for FRET include, determining the structure and conformation of proteins, determining the distribution and assembly of protein complexes, determining receptor/ligand interactions, immunoassays, enzymatic assays, probing interactions of single molecules, determining the structure and conformation of nucleic acids, real-time PCR assays and SNP detection, detecting nucleic acid hybridization, primer-extension assays for detecting mutations, automated DNA sequencing, determining the distribution and transport of lipids, membrane fusion assays, membrane potential sensing, indicators for cyclic AMP and calcium, and detecting and quantifying Akt activation in tumours, such as breast tumours.

"Coincidence FRET" or "two-site" FRET, describes the method of simultaneously labeling a single protein on two distinct sites with a donor and a acceptor pair, and detecting the FRET between them.

"Immunologically distinct" in the context of antibodies, refers to antibodies raised in different host species or different isotypes from the same species. In the present invention, the first primary antibody is raised in a different host species to the second primary antibody or the first primary antibody is a first isotype from a species and the second primary antibody is a second isotype from the same species, where the first and second isotypes are different. Exemplary host species include, mouse, rat, rabbit, goat, camel, sheep or horse. For example, the first primary antibody can be raised in mouse and the second primary antibody can be raised in rabbit. This enables the first secondary antibody to be a generic anti-mouse antibody (labeled with a donor) and the second secondary antibody to be a generic anti-rabbit antibody (conjugated to an enzyme). This provides a generic, high throughput methodology. In a preferred embodiment, the first primary antibody is an anti-Akt mouse antibody and the second primary antibody is an anti-pAkt rabbit antibody.

"Antibody" is used in the broadest sense and specifically encompasses whole immunoglobulins as well as antibody or antigen-binding fragments thereof, such as variable domains. Exemplary whole immunoglobulins include full-length and native antibodies, monoclonal antibodies (including full-length monoclonal antibodies), polyclonal antibodies, multispecific antibodies (e.g. bispecific antibodies), chimeric antibodies.

"Monoclonal antibody" refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. Monoclonal antibodies can be made by any technique or methodology known in the art including, hybridoma methods, recombinant DNA methods and isolation from phage antibody libraries.

In contrast, "polyclonal antibodies" are typically a heterogeneous population of immunoglobulin isotypes and/or classes and also exhibit a variety of epitope specificity.

"Chimeric antibody" refers to a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence. Chimeric antibodies include fragments of such antibodies, provided that the antibody exhibits the desired biological activity of its parent antibody, for example binding to the same epitope.

"Antibody or antigen-binding fragment", refers to a portion of a full-length antibody in which a variable region or a functional capability of the parent antibody is retained, for example, specific epitope binding. The antibody or antigen-binding fragments of the invention have a conserved epitope in the constant region for secondary recognition. Examples of antibody fragments include, but are not limited to, a Fab, Fab', F(ab')$_2$, Fd, Fv, scFv and scFv-Fc fragments, diabody, triabody, tetrabody, linear antibody, single-chain antibody, and other multispecific antibodies formed from antibody fragments.

"Fab fragment" refers to fragment-antigen binding fragment, which is a region on an antibody that binds to antigens. It is composed of one constant and one variable domain of each of the heavy and the light chain. These domains shape the antigen-binding site at the amino terminal end of the fragment. The two variable domains bind the epitope on their specific antigens. The Fab fragments of the invention have a conserved epitope in the constant region for secondary antibody recognition.

Methods of preparing Fab fragments are well known to the skilled person, for example, the enzyme papain can be used to cleave a whole immunoglobulin into two Fab fragments and an Fc fragment.

Fab fragments can be further cleaved to form F(ab')$_2$ and Fab' fragments, using methods known to the skilled person. For example, the enzyme pepsin can be used to cleave a Fab fragment below the hinge region to produce a F(ab')$_2$ fragment and a pFc' fragment. Alternatively, the enzyme IdeS (Immunoglobulin degrading enzyme from *Streptococcus pyogenes*, trade name FabRICATOR) can be used to cleave IgG in a sequence specific manner at neutral pH to produce F(ab')$_2$ fragments. F(ab')$_2$ fragments can be split into two Fab' fragments, for example, by mild reduction.

A "single-chain Fv" or "scFv" antibody fragment is a single chain Fv variant comprising the heavy chain variable domain ($V_H$) and the light chain variable domain ($V_L$) of an antibody, in which the domains are present in a single polypeptide chain and which is capable of recognising and binding antigen. The scFv fragments of the invention have a conserved epitope in the constant region for secondary antibody recognition. The scFv polypeptide optionally contains a polypeptide linker positioned between the $V_H$ and $V_L$ domains that enables the scFv to form a desired three-dimensional structure for antigen binding.

Methods for producing scFvs are well known to the skilled person. For example, separate $V_H$ and $V_L$ chains can be fused together. scFvs are approximately half the size of Fab fragments, yet retain the original specificity of the parent antibody.

"Diabody" refers to a small antibody fragment having two antigen-binding sites. Each fragment contains a $V_H$ domain concantenated to a $V_L$ to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites.

"Linear antibody" refers to antibodies that comprise a pair of tandem Fd segments ($V_H$-$C_H$1-$V_H$-$C_H$1) that form a pair of antigen binding regions. Linear antibodies can be bi-specific or mono-specific.

The antibodies and antibody or antigen-binding fragments thereof of the invention can be tagged. In preferred embodiments, the tag is FLAG.

"Primary antibody" refers to an antibody or an antibody or antigen-binding fragment thereof that binds to a first site on a molecule, such as a protein, DNA or a lipid. The primary antibody has binding specificity for a site on a molecule. The first primary antibody binds to a first site on a molecule, such as a protein. In preferred embodiments, the first site is Akt(pan). The second primary antibody binds to a second site on a molecule, such as a protein. In preferred embodiments, the second site is pAkt(T308). In preferred embodiments, the primary antibodies are unlabeled. In other embodiments, the primary antibodies can be labeled. For example, the label can be a tag, such as a FLAG tag.

In embodiments of the invention, the primary antibodies can be whole immunoglobulins or antibody or antigen-binding fragments thereof. Combinations of the above are also envisaged. Preferred antibody fragments are Fab fragments or scFv fragments. For example, in methods of the invention, both the first primary antibody and the second primary antibody can be whole immunoglobulins. Alternatively, both the first primary antibody and the second primary antibody can be an antibody or antigen-binding fragment. In some embodiments, the first primary antibody and the second primary antibody are Fab fragments, scFv fragments or combinations thereof. Alternatively, the first primary can be a whole immunoglobulin and the second primary antibody can be an antibody or antigen-binding fragment or the second primary antibody can be an antibody or antigen-binding fragment and the second primary antibody can be a whole immunoglobulin. In some embodiments, the primary antibodies can be tagged (for example, with a FLAG tag) and the secondary antibodies can have a binding specificity for the tag (e.g. anti-FLAG).

"Secondary antibody" refers to an antibody or an antibody or antigen-binding fragment thereof that binds to a primary antibody, such as the first or second primary antibody, or a label on a primary antibody, such as a FLAG tag.

In embodiments of the invention, the secondary antibodies can be whole immunoglobulins or antibody or antigen-binding fragments thereof. Combinations of the above are also envisaged. Preferred antibody fragments are Fab fragments or scFv fragments. In particularly preferred embodiments, at least one secondary antibody is an antibody or antigen-binding fragments. In preferred embodiments, both the first primary antibody and the second primary antibody are antibody or antigen-binding fragments. In some embodiments, the first secondary antibody and the second secondary antibody are Fab fragments, scFv fragments or combinations thereof. Alternatively, the first secondary antibody can be an antibody or antigen-binding fragment and the second secondary antibody can be a whole immunoglobulin or the first secondary antibody can be a whole immunoglobulin and the second secondary antibody can be an antibody or antigen-binding fragment. In some embodiments, the first secondary antibody and the second secondary antibody are not both whole immunoglobulins. The present invention was found not to work for some secondary antibodies where both were whole immunoglobulins, presumably because of conformational issues causing the FRET donor and FRET acceptors distances to be greater than required for FRET to occur (>10 nm). This was found to be the case regardless of the order of application of the primary and secondary antibodies.

In some embodiments, an enzyme is conjugated to or fused to a secondary antibody. In preferred embodiments, the enzyme is conjugated to or fused to the second secondary antibody. In embodiments where the second secondary antibody is a scFv fragment, the scFv fragment can be recombinantly fused with the enzyme.

In the present invention, the first site is different from the second site to enable FRET to be detected between the different sites. In preferred embodiments, the first and second sites are on the same molecule. In particularly preferred embodiments, the first and second sites are on the same protein. In other embodiments, the first and second sites are on a different molecule, for example different proteins in a complex.

An "isolated" sample is a biological sample that has been isolated from a subject, for example, an isolated tumour sample. The biological sample can include organs, tissues, cells and/or fluids.

The term "subject" refers to any animal, particularly an animal classified as a mammal, including humans, domesticated and farm animals, and zoo, sports, or pet animals, such as dogs, horses, cats, cows, and the like. Preferably, the subject is human.

"Wash step" in the context of the present invention is used in its usual sense in immunohistochemistry to mean that the sample is washed with an acceptable solution, such as saline solution. For example, the wash step can be used to remove any unbound antibody from a preceding step or to remove any detectably labelled substrate that has not been activated to form an activated conjugate.

Methods of the Invention

The methods of the invention are sensitive, quantitative and allow determination of the localization of (altered) molecular pathways using conventional antibodies. Such methods aid in the detection of pharmacodynamic markers and facilitate the discovery/development of new small molecule inhibitors.

The methods of the invention can also be used to detect molecular heterogeneity in tumours, which may be used as a critical parameter in prognosis of cancer.

The methods of the invention can be used to determine the localisation and to quantify the interaction of proteins, such as different proteins in a complex. The methods of the invention can also be used to determine the phosphorylation status of intracellular molecules. The methods of the invention can be used in combination with detection by fluorescence lifetime imaging microscopy (FLIM). Time resolved FRET can provide such information in single cells and in formalin-fixed paraffin-embedded (FFPE) tumour tissue.

The present invention provides a novel methodology employing at least two primary antibodies, at least two secondary antibodies and a conjugate.

The first primary antibody binds to a first site on a molecule and the second primary antibody binds to a second site on a molecule, wherein the second site is different from the first site and wherein the first and second primary antibodies are immunologically distinct.

The first secondary antibody is labelled with a fluorescence resonance energy transfer (FRET) donor and binds to the first primary antibody; and the second secondary antibody is conjugated to an enzyme and binds the second primary antibody, wherein the first secondary antibody does not bind the second primary antibody and the second secondary antibody does not bind the first primary antibody.

The conjugate comprises a FRET acceptor and a substrate specific for the enzyme, wherein when the substrate reacts with the enzyme, an activated conjugate, which activated conjugate binds to electron rich moieties on a molecular surface adjacent to the enzyme.

The methods of the present invention comprise the steps of contacting a sample with the at least two primary antibodies, contacting the sample with the at least two secondary antibodies, performing a wash step, contacting the sample with the conjugate, and detecting any FRET signal generated by the FRET acceptor.

Using the methods of the invention, it is possible to detect a FRET signal if the first site and second site are in close spatial proximity (less than 10 nm), even if the first site and second site are expressed at low levels.

Advantageously, the methods of the invention can be used on tissue sections as well as cell sections. Advantageously, the methods of the invention can be used to detect two sites in close proximity that are on the same molecular surface (e.g. a protein), as well as two sites in close proximity that are on different molecular surfaces (e.g. a protein).

In the methods of the invention, the at least two primary antibodies are contacted with the sample. The at least two primary antibodies can be contacted with the sample at the same time as one another or sequentially to one another. Therefore, the first primary antibody can be contacted with the sample first and then the second primary antibody can be contacted with the sample. Alternatively, the second primary antibody can be contacted with the sample first and then the second primary antibody. When the first and second primary antibodies are contacted with the sample sequentially to one another, an optional wash step can be performed between the steps in the sequence.

The first primary antibody binds to any first site present in the sample and the second primary antibody binds to any second site present in the sample. The optional wash step removes any unbound primary antibody.

The at least two secondary antibodies can be contacted with the sample at the same time as the at least two primary antibodies or the at least two primary antibodies can be contacted with the sample before the at least two secondary antibodies. The at least two secondary antibodies can be contacted with the sample at the same time as one another or sequentially to one another. Therefore, the first secondary antibody can be contacted with the sample first and then the second secondary antibody can be contacted with the sample. Alternatively, the second secondary antibody can be contacted with the sample first and then the first secondary antibody. When the first and second secondary antibodies are contacted with the sample sequentially to one another, an optional wash step can be performed between the steps in the sequence. In embodiments where the at least two primary antibodies are contacted with the sample before the at least two secondary antibodies, an optional wash step can be performed between administration of the at least two primary antibodies and the administration of the at least two secondary antibodies.

The first secondary antibody binds to the first primary antibody and the second primary antibody binds to the second primary antibody. The optional wash step removes any unbound secondary antibody or any secondary antibody that has bound to primary antibody that has not bound the first or second site (i.e. unbound primary antibody).

Following contact of the at least two primary antibodies and the at least two secondary antibodies with the sample, a wash step is performed before the conjugate is contacted with the sample. The wash step removes any antibody (primary or secondary) that has not bound its target (e.g. the first site, second site, first primary antibody or second primary antibody). Saline solution or another suitable solution can be used to perform the wash steps in the methods of the invention. The conditions used in the wash step are well known to a person of ordinary skill in the art.

Following the wash step, the conjugate is contacted with the sample. Where the second primary antibody has bound the second site and the second secondary antibody has bound the second primary antibody, the substrate of the conjugate reacts with the enzyme conjugated to the second secondary antibody to form an activated conjugate. The activated conjugate will binds to electron rich moieties on a molecular surface (e.g. a protein surface) adjacent to the enzyme. The enzyme can activate multiple conjugates, providing for the binding of multiple activated conjugates to electron rich moieties on a molecular surface adjacent to the enzyme. This amplifies the number of activated conjugates containing FRET acceptors that are bound in the vicinity of the second site.

Any FRET signal generated by the FRET acceptor is detected.

In embodiments where the FRET donor on the bound first secondary antibody is in close enough proximity (less than 10 nm) to the FRET acceptors on the bound activated conjugate, a positive FRET signal can be detected.

Where the FRET donor on the bound first secondary antibody is not in close enough proximity (greater than 10 nm) to the FRET acceptors on the bound activated conjugate, the FRET signal will be reduced or absent.

Where either or both of the first and second sites are not present in the sample, no FRET signal will be detected.

In another aspect of the invention, the enzyme activation system can be applied to the first secondary antibody in addition to the second secondary antibody. This advantageously amplifies both the FRET donor signal and the FRET acceptor signal. In this aspect, the first secondary antibody is conjugated to an enzyme in place of a FRET donor. The method further employs a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second secondary antibody.

The methods of the invention are adapted accordingly. For example, the method can comprise the steps of contacting a sample with the at least two primary antibodies, contacting the sample with the at least two secondary antibodies, performing a wash step, contacting the sample with a first conjugate specific for the enzyme conjugated to the first secondary antibody and a second conjugate specific for the enzyme conjugated to the second secondary antibody, and detecting any FRET signal generated by the FRET acceptor. The first conjugate can be applied simultaneously or sequentially to the second conjugate. For example, the first conjugate can be contacted with the sample first and then the second conjugate can be contacted with the sample. Alternatively, the second conjugate can be contacted with the sample first and then the first conjugate. When the first and second conjugates are contacted with the sample sequentially to one another, an optional wash step can be performed between the steps in the sequence.

In embodiments where the FRET donors on the bound first activated conjugate are in close enough proximity (less than 10 nm) to the FRET acceptors on the bound second activated conjugate, a positive FRET signal can be detected.

Where the FRET donors on the bound first activated conjugate are not in close enough proximity (greater than 10 nm) to the FRET acceptors on the bound second activated conjugate, the FRET signal will be reduced or absent.

Where either or both of the first and second sites are not present in the sample, no FRET signal will be detected.

In one aspect of the invention, the primary antibodies are unlabelled. For example, the primary antibodies are not labelled with a FRET donor or FRET acceptor. This has the advantage that the methods of the invention can provide a high throughput, generic methodology that is not reliant on producing primary antibodies with individual binding specificities that are labelled with a FRET donor or FRET acceptor, which is time-consuming and costly.

The primary antibodies can be labelled. For example, the primary antibodies can be labelled with a FRET donor or FRET acceptor. Although less preferred, this aspect is covered by the present invention. In this aspect, the secondary antibodies can be dispensed with. Alternatively, a labelled primary antibody can be used in combination with a primary antibody-second antibody pairing and a conjugate. For example, a first primary antibody labelled with a FRET acceptor can be used in combination with a second primary antibody that is bound by a second secondary antibody conjugated to an enzyme and a conjugate. In this instance, the first secondary antibody can be dispensed with. Alternatively, a first primary antibody that is bound by a first secondary antibody labeled with a FRET acceptor can be used in combination with a second primary antibody that is conjugated to an enzyme and a conjugate. In this instance, the second secondary antibody can be dispensed with. In these embodiments, the enzyme activation system can be applied to the first primary antibody in addition to the second primary/secondary antibody. This advantageously amplifies both the FRET donor signal and the FRET acceptor signal. In this aspect, the first primary antibody is conjugated to an enzyme in place of a FRET donor. The method further employs a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second primary/secondary antibody.

The methods of the invention are adapted accordingly. For example, the method can comprise the steps of contacting a sample with the at least two primary antibodies, optionally contacting the sample with at least one secondary antibody, performing a wash step, contacting the sample with a first conjugate specific for the enzyme conjugated to the first primary/secondary antibody and a second conjugate specific for the enzyme conjugated to the second primary/secondary antibody, and detecting any FRET signal generated by the FRET acceptor. The first conjugate can be applied simultaneously or sequentially to the second conjugate. For example, the first conjugate can be contacted with the sample first and then the second conjugate can be contacted with the sample. Alternatively, the second conjugate can be contacted with the sample first and then the first conjugate. When the first and second conjugates are contacted with the sample sequentially to one another, an optional wash step can be performed between the steps in the sequence.

In embodiments where the FRET donors on the bound first activated conjugate, first primary antibody or first secondary antibody are in close enough proximity (less than 10 nm) to the FRET acceptors on the bound second activated conjugate, a positive FRET signal can be detected.

Where the FRET donors on the bound first activated conjugate, first primary antibody or first secondary antibody are not in close enough proximity (greater than 10 nm) to the FRET acceptors on the bound second activated conjugate, the FRET signal will be reduced or absent.

Where either or both of the first and second sites are not present in the sample, no FRET signal will be detected.

In some embodiments, the methods of the invention employ more than two primary antibodies.

In some embodiments, the methods of the invention employ more than two secondary antibodies.

The samples of the invention include isolated biological samples, isolated cells and tissue sections. In preferred embodiments, the samples are breast tumour samples, including breast tumour tissue sections.

Advantageously, the secondary antibodies employed in the invention can be antibody or antigen-binding fragments, such as Fab fragments or scFv fragments, rather than whole immunoglobulins. The secondary antibodies can be a combination of Fab fragments and whole immunoglobulins (Fab fragment mixtures). Embodiments of the invention employing antibody or antigen-binding fragments (for example, ranging in size from 50 kDa to 100 kDa) or Fab fragment mixtures for the secondary antibodies have been found to be particularly effective. Particular advantages are a reduced the FRET donor and FRET acceptor chromophore distance and increased the FRET efficiency, easy penetration of tissues and binding to their targets. Additionally, their inherent specificity is further enhanced by the fact that they lack the Fc region, therefore any background that results from non-specific binding to endogenous Fc receptors is significantly reduced. This is particularly advantageous where the two target sites are on the same molecule.

The use of an enzyme activation system in combination with the FRET methods of the invention improves the FRET efficiency, particularly in two-site FRET. Previously, it was anticipated that the size of the system would increase the distance between the FRET donor and FRET acceptor, leading to loss of FRET. However, the inventors found that the methods of the invention provide an improved signal/noise ratio, as well as a low cost, generic and robust high throughput methodology.

Advantageously, the enzyme activation system increases the detection of low-expressed proteins and also allows dilution of primary antibodies, itself reducing non-specific interactions and therefore improving specificity.

The methods of the invention have the advantage of a significant increase in sensitivity, without an increase in the background.

Figure 1:
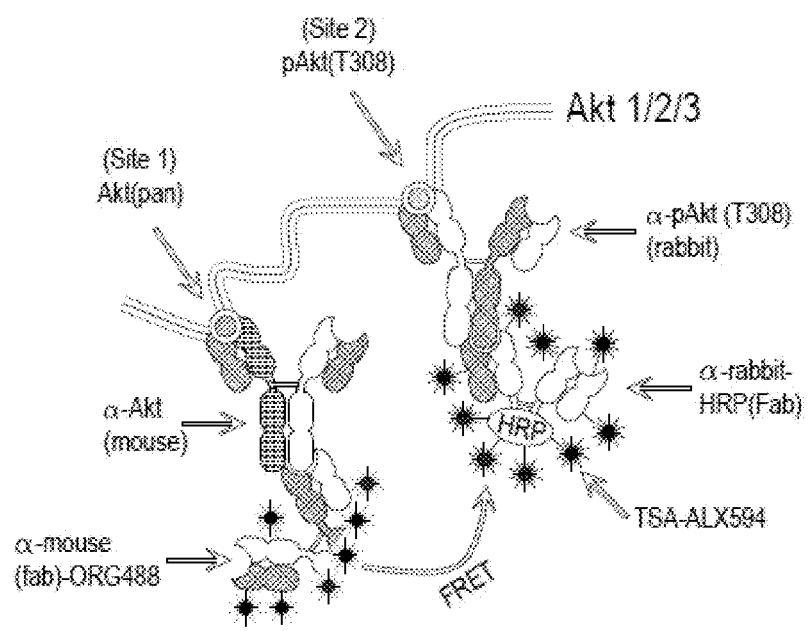
FIG. 1 shows one specific embodiment of the present invention where a two-site FRET TSA method is used to detect the targets Akt(pan) and pAkt(T308) when they are in close spatial association (less than 10 nm). The method uses a TSA-labeled amplification system with Fab fragments as secondary antibodies. Anti-mouse Fab fragment-ORG488 conjugates were used as donor and anti-rabbit Fab fragment-HRP conjugates associated with TSA-ALX594 were used as acceptor chromophores.

FIG. 1 of the drawings shows one specific, non-limiting embodiment of the present invention, where the method is used in quantifying the activation of pAkt (pT308) proteins.

Primary, whole immunoglobulins anti-Akt (mouse) and anti-pAkt (T308) (rabbit) are contacted with a sample the sites Akt(pan) and pAkt(T308) on the same Akt 1/2/3 protein. Secondary, Fab fragments anti-mouse-ORG488 and anti-rabbit-HRP are contacted with the sample and binds the anti-Akt (mouse) and anti-pAkt (T308) (rabbit) antibodies, respectively. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the pAkt(T308) target site. The short half-life of the tyramide radicals results in minimal diffusion-related loss of ALX594 signal localisation. A positive FRET signal Is generated between ORG488 and ALX594 where the two are in close proximity (less than 10 nm), indicating that Akt(pan) and pAkt(T308) are in close proximity on the Akt 1/2/3 protein in the sample. The FRET signal can be detected in a time resolved manner by multiple frequency domain FLIM (mFD-FLIM).

In one aspect, the invention relates a highly sensitive quantitative coincidence assay. In certain embodiments, two-site TSA-FRET combines the immunofluorescence tyramide signal amplification (TSA) with Fab fragment secondary antibody conjugates, in order to maximize sensitivity and specificity.

In another aspect of the present invention, the methods can be used to detect protein-protein interaction, for example the interaction of different proteins in a complex. In such a method, two primary antibodies are contacted with a sample of interest. This can be a tissue section or a cell sample. The primary antibodies have different binding specificities, where one primary antibody binds a site on a protein and the second primary antibody binds a site on a different protein.

Secondary antibodies that are specific for the primary antibodies are contacted with the sample. One of the secondary antibodies is labelled with a FRET donor, such as ORG-488. The other secondary antibody is conjugated or fused to HRP. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the target site. The short half-life of the tyramide radicals results in minimal diffusion-related loss of ALX594 signal localisation. A positive FRET signal Is generated between the FRET donor (e.g. ORG488) and ALX594 where the two are in close proximity (less than 10 nm), indicating that protein sites are in close proximity in the sample.

The FRET signal can be detected in a time resolved manner by multiple frequency domain FLIM (mFD-FLIM).

In one specific, non-limiting embodiment of the present invention, the protein-protein interaction detected can be HER2/HER3 interaction, for example in breast cancer tissue.

Primary, monoclonal anti-HER2 (rabbit) (binds to Tyr aa1248) and anti-HER3 (mouse) (binds around aa1175-1275) are contacted with a sample. Secondary, Fab fragments anti-rabbit-ATTO488 (donor) and anti-mouse-HRP (acceptor) are contacted with the sample and binds the anti-HER2 (rabbit) and anti-HER3 (mouse) antibodies, respectively. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the HER3 target site. The short half-life of the tyramide radicals results in minimal diffusion-related loss of ALX594 signal localisation. A positive FRET signal Is generated between ATTO488 and ALX594 where the two are in close proximity (less than 10 nm), indicating that HER2 and HER3 are in close proximity in the sample. The FRET signal can be detected in a time resolved manner by multiple frequency domain FLIM (mFD-FLIM).

A "plug-in" algorithm can be used to automate an mFD-FLIM. Such a miniaturized instrument automatically distinguishes between regions of interest (ROI) in cells and tumours, which allows for unbiased selection of specific ROIs.

In embodiments of the invention, miniaturized automated mFD-FLIM can be used in combination with two-site TSA-FRET to readily detect the activation of an onco-protein (PKB/Akt or HER2/HER3), in breast and/or colon tumours with a resolution that evidences molecular heterogeneity within tumours. The methods can be used to routinely to inform on prognostic, predictive and diagnostic biomarkers.

Advantageously, the methods of the invention combine the spatio-temporal and quantitative attributes of time resolved FRET detected by multiple frequency domain FLIM (mFD-FLIM) with the sensitivity of the tyramide signal amplification (TSA) system.

Kits of the Invention

The present invention also provides kits that can be used in the aforementioned methods of the invention.

The present invention provides a kit for detecting molecules, the kit comprising, at least two primary antibodies, at least two secondary antibodies and a conjugate.

The first primary antibody binds to a first site on a molecule and the second primary antibody binds to a second site on a molecule, wherein the second site is different from the first site and wherein the first and second primary antibodies are immunologically distinct.

The first secondary antibody is labelled with a fluorescence resonance energy transfer (FRET) donor and binds to the first primary antibody; and the second secondary antibody is conjugated to an enzyme and binds the second primary antibody, wherein the first secondary antibody does not bind the second primary antibody and the second secondary antibody does not bind the first primary antibody.

The conjugate comprises a FRET acceptor and a substrate specific for the enzyme. When the substrate reacts with the enzyme, an activated conjugate forms, which activated conjugate binds to electron rich moieties on a molecular surface adjacent to the enzyme.

In another aspect of the invention, the enzyme activation system can be applied to the first secondary antibody in addition to the second secondary antibody. This advantageously amplifies both the FRET donor signal and the FRET acceptor signal. In this aspect, the first secondary antibody is conjugated to an enzyme in place of a FRET donor molecule. The kit further includes a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second secondary antibody.

In one aspect of the invention, the primary antibodies are unlabelled. For example, the primary antibodies are not labelled with a FRET donor or FRET acceptor. This has the advantage that the kits of the invention can be used in a high throughput, generic methodology that is not reliant on producing primary antibodies with individual binding specificities that are labelled with a FRET donor or FRET acceptor molecules, which is time-consuming and costly.

The primary antibodies can be labelled. For example, the primary antibodies can be labelled with a FRET donor or FRET acceptor. Although less preferred, this aspect is covered by the present invention. In this aspect, the secondary antibodies can be dispensed with. Alternatively, a labelled primary antibody can be used in combination with a primary antibody-second antibody pairing and a conjugate. For example, a first primary antibody labelled with a FRET acceptor can be used in combination with a second primary antibody that is bound by a second secondary antibody conjugated to an enzyme and a conjugate. In this instance, the first secondary antibody can be dispensed with. Alternatively, a first primary antibody that is bound by a first secondary antibody labelled with a FRET acceptor can be used in combination with a second primary antibody that is conjugated to an enzyme and a conjugate. In this instance, the second secondary antibody can be dispensed with. In these embodiments, the enzyme activation system can be applied to the first primary antibody in addition to the second primary/secondary antibody. This advantageously amplifies both the FRET donor signal and the FRET acceptor signal. In this aspect, the first primary antibody is conjugated to an enzyme in place of a FRET donor. The kit further includes a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second primary/secondary antibody.

EXAMPLES

The present invention is described in more detail with reference to the following non-limiting examples, which are offered to more fully illustrate the invention, but are not to be construed as limiting the scope thereof.

The methods of the invention can be used to quantify Akt activation status in fixed SKBR3 breast tumour cells as well as FFPE human breast and colon tumours in a TMA format.

The methods of the invention can also be used to detect and/or measure protein-protein interactions, such as HER2/HER3 interactions in fixed SKBR3 breast tumour cells as well as in breast cancer tissue.

Previous studies of endogenous proteins using FLIM have been limited due to the lack of sensitivity.

The methods of the present invention allow the identification of the molecular heterogeneity of the Akt activation between different regions of interest within the same core and between various cores within the same patient.

The methods of the present invention also allow the identification of HER2/HER3 interactions in different parts of cells and between different regions of interest within the same core and between various cores within the same patient.

The findings show that the two-site TSA-FRET assay of the invention is a highly sensitive and specific assay for the detection of molecular heterogeneity that benefits from a high and quantifiable dynamic range.

The inventors have also designed a novel coincidence FRET assay using secondary antibody-dye conjugates, with the aims of increasing sensitivity.

For the Akt activation studies, monoclonal primary antibodies, mouse anti-panAkt, rabbit anti-PAkt (pT308) were obtained form Cell Signaling technology, USA. IRDye conjugated secondary antibodies, goat anti-mouse IgG-IRDye and goat anti-rabbit IgG-IRDye 680LT were purchased from LI-COR Biosciences, USA. Affinity-purified Fab fragments antibody conjugate and dimer goat Fab anti-rabbit IgG-HRP were purchased from Bethyl laboratories, TX, USA. Affinity-purified dimer Fab fragments antibody, AffiniPure donkey Fab fragment anti-mouse IgG were purchased from Jackson ImmunoResearch, Suffolk, UK. Tyramide Signal Amplification (TSA) kit with Alexa Fluor® 594 tyramide was purchased from Invitrogen Life Technologies, USA. Human breast cancer SKBR3 and MCF7 cell lines were obtained from CRUK cell culture bank. Ten human breast tumour samples from three different patients were obtained from the Experimental Histopathology Laboratory at LRI-CRUK.

ORG488 conjugation to the anti-mouse-specific dimer Fab secondary antibody was performed using a standard NHS-ester conjugation protocol.

Example 1—Co-Localization of Endogenous panAkt and pT308 Using Fab Fragment-Dye Conjugates in Fixed SKBR3

SKBR3 cells were seeded at 30,000 cells/well; with 0.4 ml/well DMEM culture medium in two Millicell 8-well glass chamber slides (Millipore's Millicell® EZ Slide).

Cells were incubated for 24 h at 37° C., 10% CO2, and 95% relative humidity. The next day, cells were starved for 6 h and cultured in DMEM medium without serum or in the presence of EGF (100 ng/ml) for 6 min or LY294002 (50

μM) for 30 min. Prior to immunofluorescence labeling, SKBR3 cells were prepared on chamber slides, fixed in 4% PFA for 15 min, permeabilized with 0.3% Saponin for 10 min and blocked (1% BSA in PBS) for 1 h at room temperature.

Cells on the first chamber slide were immuno-labeled with primary mouse anti-panAkt (1:100). The second chamber slide was immuno-labeled with mouse anti-panAkt (1:100) and rabbit anti-pT308 antibodies (1:200) for 16 hours at 4° C. Both slides were washed in PBS, and species specific secondary antibodies, Fab anti-mouse ORG488 (20 μg/ml) and Fab anti-rabbit Alexa-594 (25 μg/ml), respectively, were applied for 2 hr at room temperature. Cells were mounted with ProLong® Gold anti-fade reagent (Invitrogen, Cat#: P36930) prior to observation under a confocal microscope.

Example 2—Co-Localization of Endogenous panAkt and pT308 Using Fab Fragment Based Tyramide Signal Amplification (TSA) Assay in Fixed SKBR3

For the Fab fragment-based TSA assay, SKBR3 cells with different conditions were prepared in two 8-well glass chamber slides as described above. The cells on the first and second chamber slides were further incubated with species-specific Fab fragment secondary antibodies, Fab anti-mouse ORG488 (20 μg/ml) Fab fragment and Fab antirabbit-HRP (10 μg/ml) conjugate, respectively for 2 h at room temperature. The cells on second chamber slide were then labeled using Alexa-594 TSA system for 15 min.

At this time point the amplification reached a plateau and the signal was not amplified further. The Alexa-594 TSA dye binds covalently to proteins immediately proximal to the target, which is ideal for sub-cellular localization of proteins.

The stained SKBR3 cells were mounted with ProLong® Gold anti-fade reagent prior to inspection under a confocal microscope. Confocal images were acquired by using a Zeiss LSM 710 inverted laser scanning confocal microscope.

Example 3—Co-Localization of Endogenous panAkt and pT308 Using Fab Fragment Based TSA Assay in FFPE Fixed Human Breast Tumour Two identical FFPE breast tumour tissue sections were dewaxed, rehydrated and subjected to heat-induced antigen retrieval in TRIS-EDTA (pH 9.0) buffer for 10 min.

To quench the background fluorescence signal, these slides were incubated with fresh sodium borohydrate (1 mg/ml in PBS) for 10 min at RT and blocked with 1% BSA/PBS. The first slide was incubated with primary mouse anti-panAkt (1:100); the second slide was incubated with both primary mouse anti-panAkt (1:100) and primary rabbit anti-pT308 antibodies (1:200). For both slides incubation was for 16 hours at 4° C.

The next day slides were washed 3× with PBS. The first slide was labeled with antimouse Fab ORG488 (20 μg/ml) secondary antibody. The second slide was labelled with anti-mouse Fab ORG488 and anti-rabbit Fab-HRP (10 μg/ml) secondary antibodies, which was then detected by using Alexa-594-TSA assay according to manufacture's protocol.

For each immunofluorescent labeling experiment a negative control was included, by replacing the primary antibody with BSA at the same volume as the primary antibody. All tissues samples were mounted with ProLong® Gold anti-fade reagent prior to observation under a confocal microscope.

Example 4—Two-Site TSA-FRET Assay

In this example, Fab fragments (50 kDa) were used as secondary antibodies.

The two-site TSA-FRET assay was found to provide a significant increase in sensitivity, without an increase in the background. Furthermore, unlike other amplification methods, TSA amplifies the signal after the antibodies bind to the antigen (FIGS. 3 to 7).

Example 5—Unamplified Two-Site FRET Assay for pT308 Quantification in Fixed SKBR3

SKBR3 cells were cultured in two 8-well chamber slides+/−stimulation with EGFR and LY294002 as described previously.

Following treatment, cells were fixed in PFA, permeabilized and blocked (1% BSA in PBS) for 1 h at room temperature. For two-site FRET, donor and acceptor chromophore-conjugated Fab fragment secondary antibodies were used against panAkt and pT308 sites.

Cells on the first chamber slide were incubated with mouse anti-panAkt primary antibody (1:100). Cells on the second chamber slide were incubated with both mouse anti-panAkt (1:100) primary antibody, and rabbit anti-pT308 antibody (1:200) overnight at 4° C. The following morning, the first chamber slide was further incubated with species-specific Fab fragment secondary antibody dye-conjugate, anti-mouse Fab-ORG488 (20 μg/ml) (as donor), for 2 h at room temperature. The second chamber slide was further incubated with species-specific anti-mouse Fab-ORG488 (20 μg/ml) and anti-rabbit-Fab ALX594 (25 μg/ml) (as acceptor), for 2 h at room temperature. The labeled SKBR3 cells were mounted with ProLong Gold anti-fade reagent.

A reference solution of Rhodamine B (in H2O) was prepared and imaged prior to multiple mFD-FLIM acquisitions of the SKBR3 cells. The donor-labeled (anti-mouse-Fab-ORG488) cells were excited with 473 nm modulated laser beam, and the emission fluorescence was detected at 510 to 530 nm by a CCD image intensifier.

The donor lifetime of Fab-ORG488 was measured in a minimum of 20 cells. Intensity and lifetime images of donor labeled cells from the same field of view were acquired. Lifetime data was analyzed using the purpose-built algorithm as described above, to calculate FRET efficiency values, using the following equation: $E=1-(tDA/tD)*100\%$; where tD is donor lifetime and tDA is donor plus acceptor lifetime. Three replicates were performed for each data point (FIG. 3(b)).

Example 6—Two-Site TSA-FRET for pT308 Quantification in Fixed SKBR3

For the acquisition of lifetime maps the mFD-FRET microscope was used as described above. SKBR3 cells were cultured in two 8-well chamber slides+/−stimulation or inhibition with EGFR and LY294002 respectively as described previously.

Following treatment, cells were fixed in PFA, permeabilized and blocked (1% BSA in PBS) for 1 h at room temperature. Cells were further incubated with peroxidase suppressor (Thermo Scientific Pierce) for 15 min to inhibit any endogenous peroxidase activity from cells.

The two-site FRET assay was performed as above. The main difference here was that cells on the second chamber slide were labeled using Alexa-594 (acceptor) TSA system for 15 min. For each experiment control cells labeled with only secondary Fab fragment conjugates were included. The labeled SKBR3 cells were mounted with ProLong Gold anti-fade reagent. A reference solution of Rhodamine B (in H2O) was prepared and imaged prior to mFD-FLIM acquisition of the SKBR3 cells. The lifetime imaging experiments were performed as above. Three replicates were performed for each data point (FIG. 3(a)).

Example 7—Two-Site TSA-FRET Assay for Quantification of pT308 in Fixed FFPE in Human Breast Tissue TSA-FRET assay for quantification of pT308 was performed on 4-μm sections of two identical FFPE-fixed breast cancer tissue samples. Following de-waxing and rehydration, sections were subjected to heat antigen retrieval by microwaving in TRIS-EDTA (pH 9.0) buffer, for 10 minutes at 800 W. Sections were then incubated in freshly prepared sodium bohydrate (1 mg/ml in PBS) buffer for 10 min at RT, followed by blocking with 1% BSA/PBS. Tissues sections were incubated with peroxidase suppressor (Thermo Scientific Pierce) for 15 min.

For the two-site TSAFRET assay, the first slide was incubated with mouse anti-panAkt (1:100), and the second slide with mouse anti-panAkt (1:100) and rabbit anti-pT308 (1:200) primary antibodies, for 16 hours at 4° C. The first slide was further immunolabeled with ORG488-conjugated anti-mouse Fab fragment secondary antibody (20 μg/ml). The second slide was immunolabeled with ORG488-conjugated anti-mouse Fab fragment (20 μg/ml) and HRP-conjugated anti-rabbit Fab fragment secondary antibody (10 μg/ml), which was detected by using Alexa-594-TSA assay.

As a control to address the specificity of the phosphorylation signal, calf intestinal alkaline phosphatase (CIP) was incubated with the tissue sections. CIP (10 units/slide) was diluted in 1×NEB buffer 3 and incubated for 30 min at room temperature. Also, the substitution of the specific primary antibodies by 1% BSA in tissue sections was used as a negative control. These control slides were also prepared as described above before mounting all tissues sections with ProLong® Gold anti-fade.

The donor lifetimes of ORG488 were determined from at least 10 ROIs of the tumours, each performed in triplicate unless otherwise indicated. The FRET efficiency was calculated as described above (FIG. 4).

Example 8—High-Throughput Two-Site TSA-FRET Assay for Quantification of pT308 Molecular Heterogeneity in Human Breast and Colon TMAs Tumour microarrays were made from biopsies obtained from 10 breast and 7 colon cancer patients. For each patient biopsy, four cores from different regions were arranged in an array. H&E staining of the TMA section confirmed that cytomorphological traits were representative of malignant tissue, as opposed to stromal tissue. Each breast TMA contained 40 (4×10) tumour cores, representing 4 distinct areas of the same tumour biopsy for each patient. Each colon TMA contained 28 (4×7) tumour cores, representing 4 distinct areas of the same tumour biopsy for each patient.

Two identical TMAs were de-waxed and rehydrated, subjected to heat antigen retrieval by microwaving in TRIS-EDTA (pH 9.0) buffer, for 10 min at 800 W power.

TMAs were further incubated with fresh sodium borohydrate buffer for 10 min, followed by blocking with 1% BSA/PBS. TMAs were the incubated with peroxidase suppressor (Thermo Scientific Pierce) for 15 min. For the two-site TSA-FRET assay was performed as indicated above. Lifetime measurements were performed using both donor-labeled and donor plus acceptor-labeled TMAs, for each core. FRET efficiency calculations with a low signal-to-noise (signal lower than 4 times the background intensity) were excluded. The maximum FRET efficiency of four-regions of interest within the core was calculated as described above (FIGS. 5 and 6).

Example 9—Automated High-Throughput Two-Site TSA-FRET Assay for Quantification of pT308 in Human Breast TMAs TMAs containing 120 cores of breast tissue, originating from biopsies taken from a large case mix of ER positive and ER negative breast cancer patients from the tumour bank at Guys Hospital, London UK. All biopsies had been taken prior to treatment, and linked to histological and clinical data comprehensively stored in a database. These were a consecutive series of breast cancers from patients diagnosed between 1993-94.

Prior to immunofluorescence labeling, two identical TMA sections were processed as described above. The TSA-FRET assay was also performed as above.

Lifetime measurements were performed using both donor-labeled and donor plus acceptor-labeled TMAs, for each core. Only samples with donor intensity of at least four times higher than the background intensity were included for FRET efficiency calculations. The highest FRET efficiency of four regions of interest within each core was calculated, as described above.

Statistical analysis was performed using the Graphpad Prism software (GraphPad Prism software, CA, USA). Results are shown as mean values±SEM. Statistical significance between the groups was calculated with the Mann-Whitney test (values are indicated in the Box and Whiskers plots) 22,31. Differences were considered statistically significant when p≤0.05 (FIG. 7).

Example 10—Optimization of the Coincidence TSA-FRET Assay for Quantification of Endogenous Akt Activation Status in SKBR3 Cells Prior to the optimization of the TSA-FRET assay, the binding specificity of human anti-Akt antibodies (panAkt, pT308) was evaluated by two-color Li-COR Western blot against endogenous Akt in SKBR3 cells (data not shown). SKBR3 cells were treated with the PI3K inhibitor, 50 μM LY294009 for 30 minutes, +/−EGF (100 ng/ml) for 6 minutes. Cells were lysed and total protein lysates evaluated by Li-COR Western blot. Single bands demonstrated specificity of the anti-Akt (panAkt, pT308) antibodies (data not shown). Incubating both panAkt and pT308 antibodies followed by the addition of species-specific NIR-dyeconjugated secondary antibodies, on a single blot, did not affect the specificity of either primary antibody (data not shown). Using both qualitative and relative quantitative assessments, the Li-COR Western showed that Akt phosphorylation was enhanced by EGF and inhibited by LY294002 in SKBR3 cells (data not shown).

These results confirmed the specificity of anti-Akt antibodies. The immunofluorescence assay uses Fab fragments as secondary antibody-dye conjugates. This approach has several advantages. Due to their small size, secondary Fab fragments easily penetrate tissues and bind to their targets. Their inherent specificity is further enhanced by the fact that they lack the Fc region, therefore any background that results from non-specific binding to endogenous Fc receptors is abolished. The use of secondary Fab fragments also reduces the batch-to-batch variation inherent in dye-labeling primary antibodies.

In addition to using Fab fragments, the TSA labeling methodology was exploited, which has been used to amplify fluorescent signals in standard immunofluorescence protocols and increases the detection threshold for very weakly-expressed proteins by 100-fold. To improve the sensitivity and specificity of the pan-Akt and pT308 antibodies, Fab fragment secondary antibody conjugates were combined with the TSA system. This assay was optimised in SKBR3 cells, with and without TSA.

Figure 10:
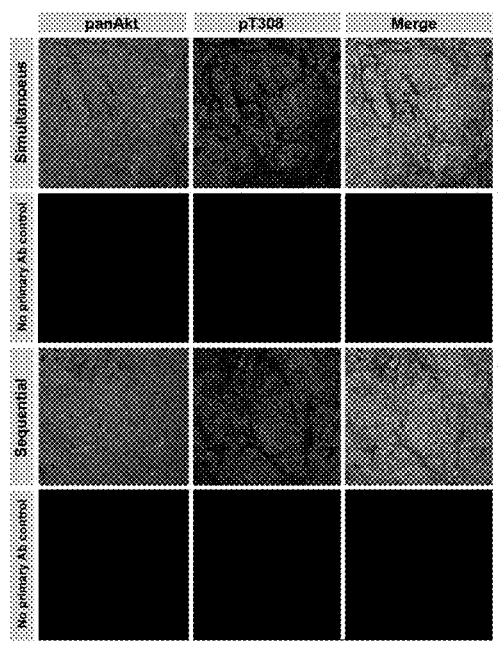
FIG. 10 shows confocal images for Fab-IgG with TSA-FRET. Confocal image analysis for panAkt and pT308.

Confocal images using Fab fragment-dye conjugates without TSA in starved or in EGF stimulated SKBR3 cells, showed enhanced plasma membrane translocation of pT308 (FIG. 10) which was significantly reduced in EGF+LY294002 treated cells (FIG. 10). The assay was further performed in the presence of TSA. EGF-stimulated SKBR3 cells displayed well-defined plasma membrane translocation of pT308 compared to unstimulated cells (FIG. 10). However, the pT308 signal was suppressed in LY2940002 treated cells indicative of a specific TSA signal for pT308 (FIG. 10). When the Fab fragment translocation signal, without TSA was compared to the TSA signal, a prominent increase was observed for the latter (FIG. 10).

These results clearly demonstrate high antibody specificity in both methods (with and without TSA system), without an increase in background. However, by using the TSA labelling system with the same dilution of primary antibodies, fluorescent signals were amplified and the signal-to-noise ratio increased. Since the Fab fragment-based TSA assay resulted in a higher signal-to-noise, this assay was used to investigate endogenous expression and co-localization of panAkt and pT308 in FFPE human breast tumour sections.

Confocal images show a clear co-localization of panAkt and pT308 at the plasma membrane (FIG. 10). The pT308 was predominantly at the plasma membrane, indicating specificity of TSA labeling in tissue. Control experiments (FIG. 10) using a Fab fragment-based TSA assay without primary antibodies produced a very weak signal, thus confirming the specificity of the Fab fragment-based TSA system in tissues. In order to establish the optimum time required for the TSA reaction to occur, a time course was performed in stimulated MCF7 cells. At 5 minutes, the pT308 signal was very weak. From 10 to 15 minutes the pT308 signal increased before signal saturation was reached at 20 minutes. 15 minutes was therefore chosen as the optimum time for TSA amplification (FIG. 10).

These results clearly highlight how the TSA system combined with secondary Fab fragment antibody-dye conjugates enhances the detection of pan and phospho-Akt in cells and tumours, whilst maintaining high specificity. Such a system can be exploited routinely in samples where the target proteins and their phospho-sites are poorly expressed.

Figure 2:
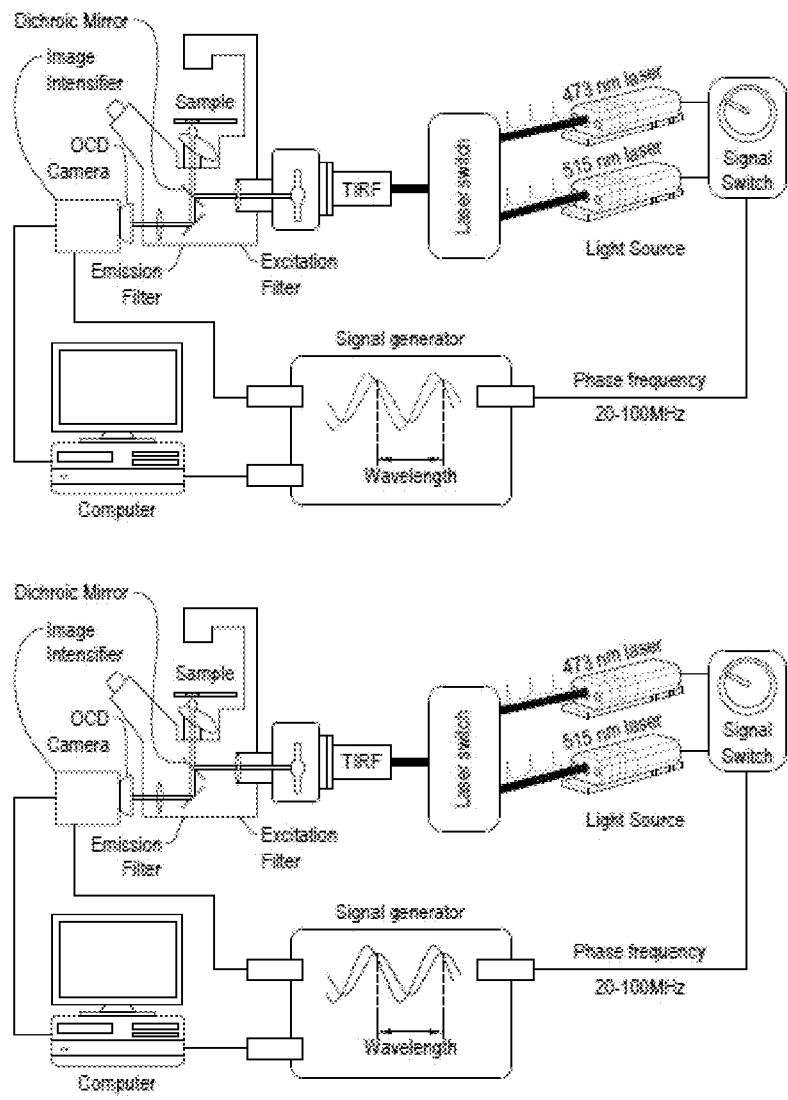
FIG. 2 shows a scheme of the FD-FLIM experimental setup.

The Fab fragment-based TSA assay was both sensitive and specific for detecting Akt activation in cells and tumour sections. Therefore, this was assay exploited to develop a more sensitive and generic two-site FRET assay. To detect time resolved FRET multiple frequency domain-FLIM (mFD FLIM) was used (FIG. 2). Schematic diagrams show the principle of the coincidence TSA-FRET with Fab fragments conjugates as secondary antibodies (FIG. 1).

Two-site TSA-FRET was performed in SKBR3 cells. Cells were starved or EGF-stimulated with or without PI3K inhibitor, and fixed according to the two-site TSA-FRET protocol. FIG. 2c shows that the average FRET efficiency of cells labeled with donor alone did not change upon EGF stimulation. However, average FRET efficiency of cells labeled with both donor (Fab fragment-ORG488) and acceptor (TSA-ALX594) significantly increased upon EGF stimulation (FIG. 3(a)). The increase in average FRET efficiency (greater than 16%) with EGF was clearly noticeable at the plasma membrane as seen from the lifetime map images, indicative of a significant increase in pT308 at the plasma membrane (FIG. 3(a)). The same coincidence FRET experiment but without the TSA amplified acceptor signal (using Fab-ALX495 conjugates as acceptor) showed that the FRET efficiency was reduced ($E_f$=7%) (FIG. 3(b)), showing that the amplification significantly improves the dynamic range of the FRET efficiency.

These results demonstrate that the two-site TSA-FRET assay can quantify the activation status of endogenous Akt in fixed cells, with high a sensitivity and specificity.

These results also show that small secondary antibody Fab fragments (50 kDa) result in a viable proximity between FRET pairs, and that the TSA system amplified the overall signal, thereby resulting in a higher FRET efficiency.

Example 11—Quantification of Akt Activation Status by Coincidence TSA-FRET Assay in Fixed FFPE Human Breast Tumours Having successfully optimized two-site TSA-FRET in SKBR3 cells, the same assay was exploited to quantify activated Akt in FFPE cancer patient samples.

For these experiments the high-throughput mFD-FLIM was used to acquire, detect and analyze automatically the average FRET efficiencies. Two-site TSA-FRET was initially performed in FFPE breast cancer samples from three different sources. Two-site TSA-FRET analysis of Akt activation in FFPE human breast tumours showed that the average FRET efficiency of donor (panAkt) alone was zero (FIG. 4(a)). However, the average FRET efficiency significantly increased in the presence of the acceptor (pT308) (FIG. 4(b) and FIGS. 12(a) and (b)). Moreover, the average FRET efficiency varied (from 2.5 to 6.0%) across breast tumour patients suggesting that TSA-FRET can be used to quantify the variation in the activation status of Akt between patients.

Figure 4A:
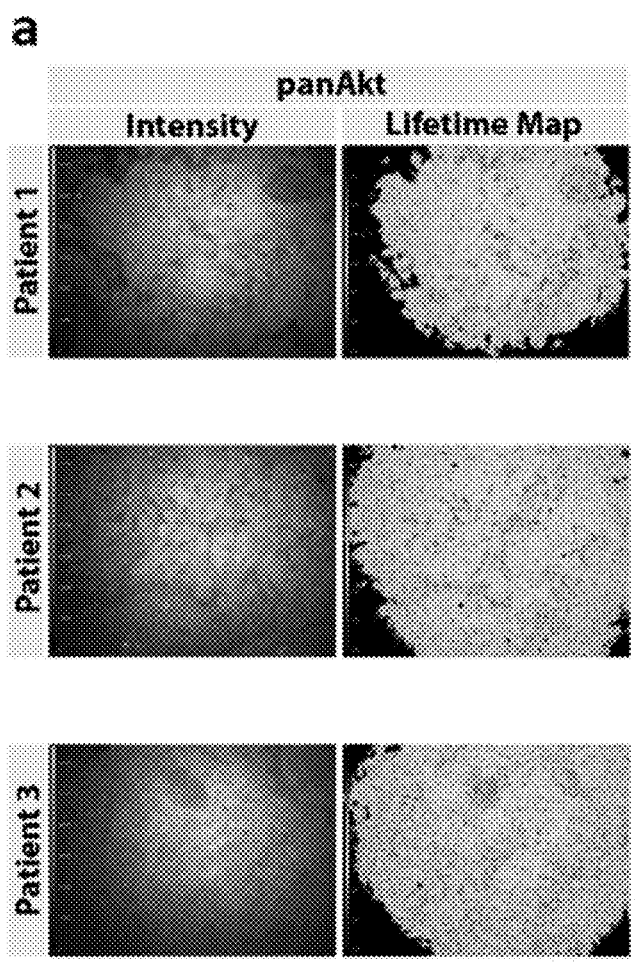
FIG. 4 shows the quantification of endogenous expression of activated Akt (pT308) in fixed FFPE human breast tumour using TSA-FRET assay.
Figure 4B:
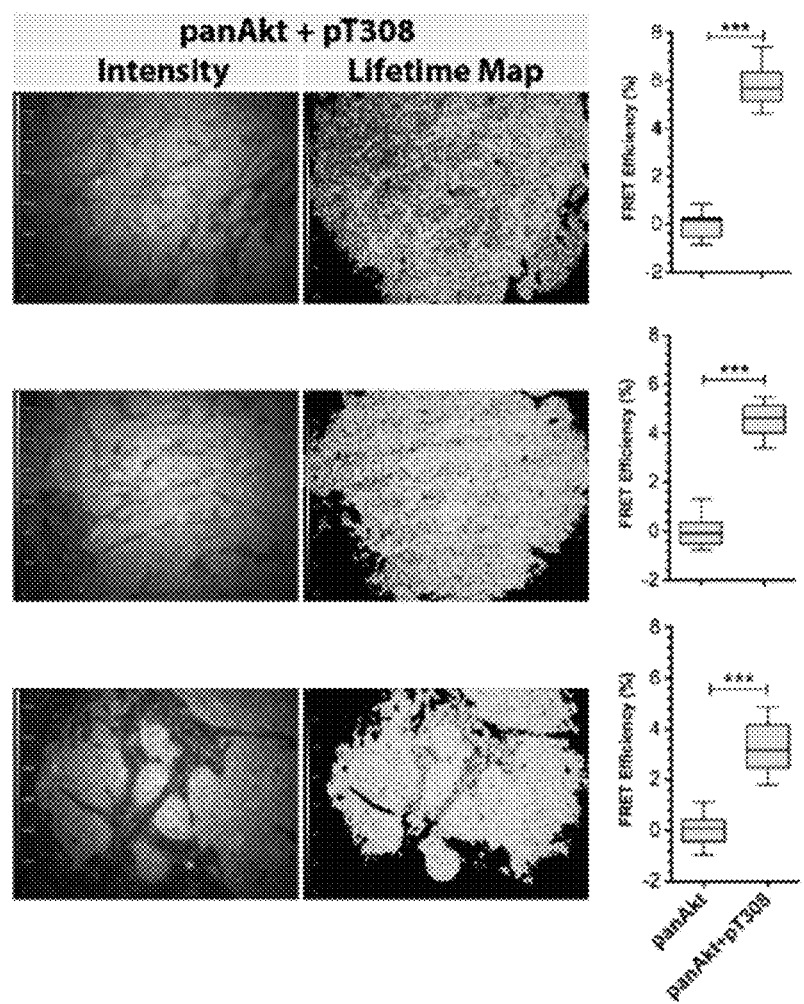
Figure 4C:
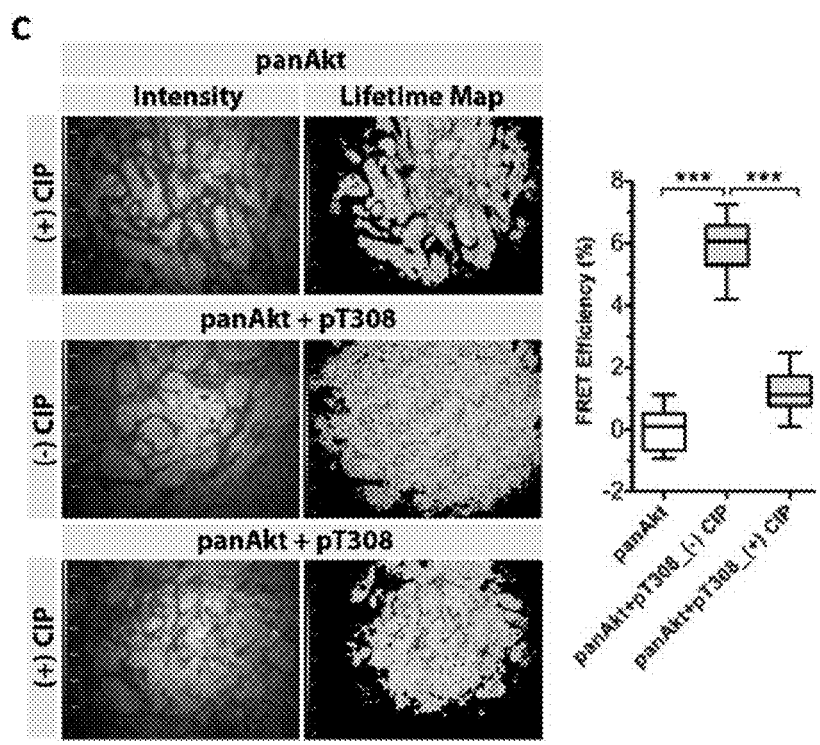

Control experiments (FIG. 4(c)) with calf intestinal alkaline phosphatase (CIP) showed that pT308 was significantly reduced (from Ef=6.0 to 1.5%) in CIP-treated tumour samples, thus confirming the specificity of the two-site TSA-FRET system in tissues.

These results have validated the two-site TSA-FRET system using secondary Fab reagents to accurately quantify the activation status of Akt in FFPE human breast tumour sections. The average FRET efficiency increased in the presence of acceptor in all three samples (FIG. 4(b) and FIGS. 12(a) and (b)) indicating significant amounts of pT308. However, the average FRET efficiency varied largely between samples. This suggested that two-site TSA- FRET assay could discriminate between different levels of Akt activation in tissues from a small sample of patients.

Example 12—High-Throughput Quantification of Akt Activation and its Molecular Heterogeneity in Human Breast Cancer by Two-Site TSA-FRET To map and quantify the molecular heterogeneity of the Akt activation status within patient breast tumours. Tumour microarrays from breast tumour biopsies obtained from 10 mixed patients were prepared. These patients had a variable ER and HER2 status as shown in Table 1B below:

TABLE 1B

| Samples | ER Status | HER2 Status |
| --- | --- | --- |
| Patient 1 | 3 | 0 |
| Patient 2 | 2 | 0 |
| Patient 3 | 3 | 0 |
| Patient 4 | 0 | 0 |
| Patient 5 | 3 | 0 |
| Patient 6 | 3 | 1 |
| Patient 7 | 3 | 2 |
| Patient 8 | 3 | 0 |
| Patient 9 | 3 | 0 |
| Patient 10 | 2 | 1 |

For each patient, four cores were selected from different regions within each biopsy. H&E staining confirmed that each core contained tumour tissue (FIG. 5(a)). In total there were 40 tumour cores per TMA. TMAs were labelled with anti-Akt (panAkt, pT308) primary antibodies, followed by the TSA labeling (as described in Materials and Methods). Each tumour core position on the donor and the corresponding donor plus acceptor TMAs were mapped. The intensity and the corresponding FLIM images for donor and donor plus acceptor labeled samples are shown for all cores in FIGS. 4b and 4c, respectively.

Figure 5A:
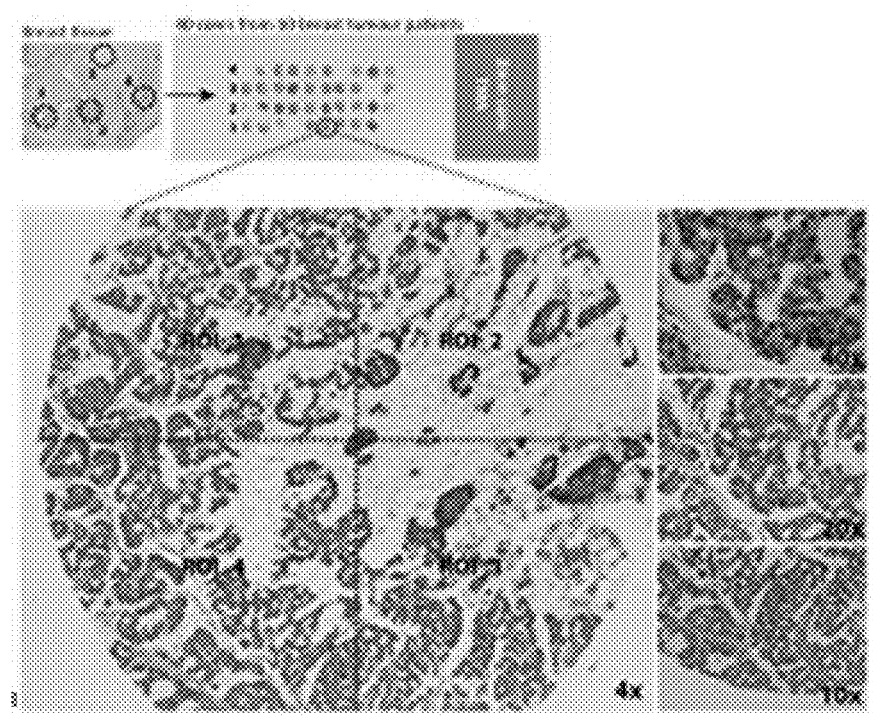
FIG. 5 shows Human breast TMA analysis for high-throughput quantification of activated Akt (pT308) and molecular heterogeneity using TSA-FRET.
FIG. 5(e)—the data presents the mean±SEM of the average FRET efficiency of the 4 cores from the same patient.

FLIM was used to map and acquire lifetime images from each tumour core position and the 4 segmented ROI (FIG. 5(a)). The maximum FRET efficiency between sectors within the same core was calculated with an Excel-macro.

Figure 3A:
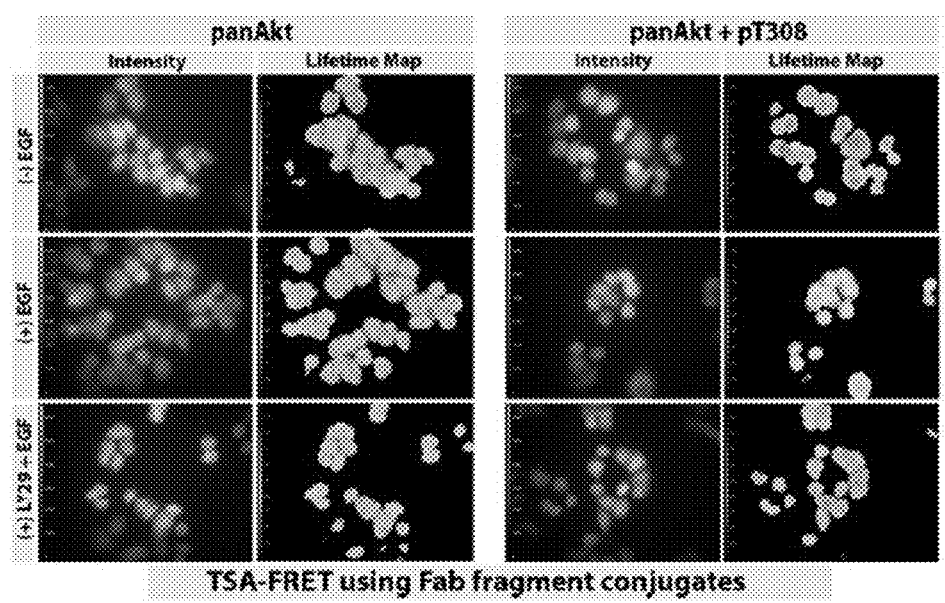
FIG. 3 shows the quantification of endogenous expression of activated Akt (pT308) in fixed SKBR3 cells using a TSA-FRET assay.
Figure 3A:
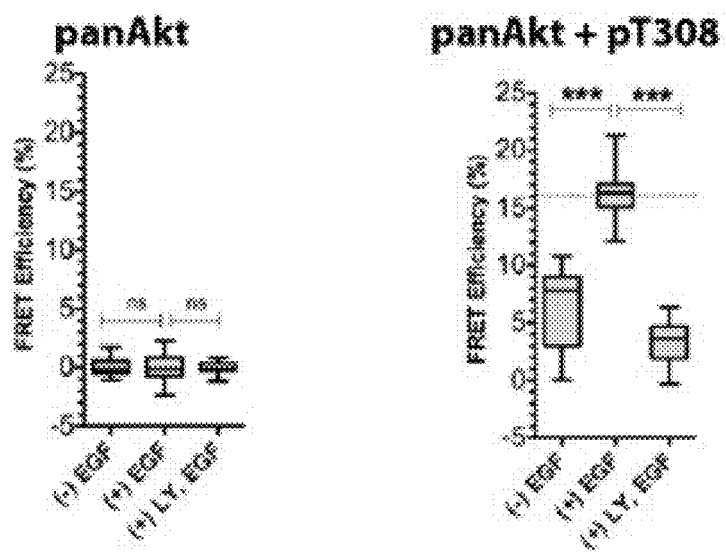
Figure 3B:
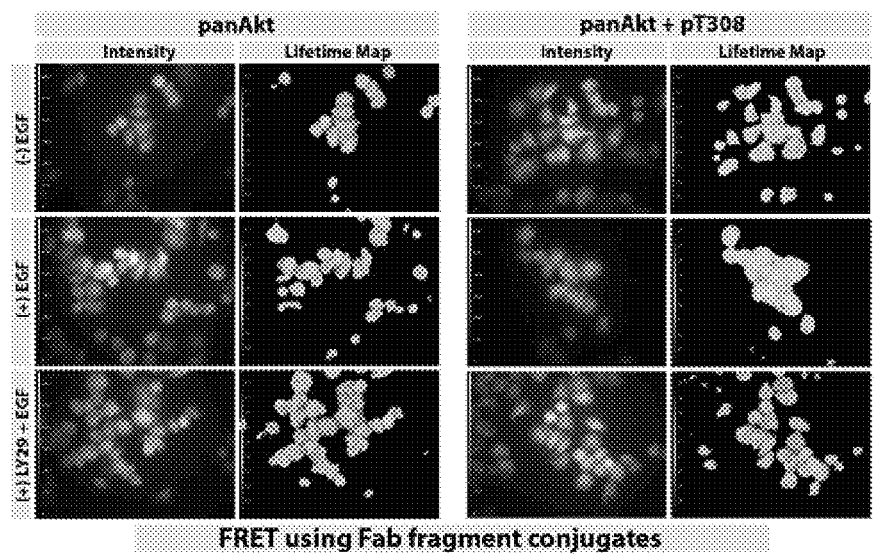
Figure 3B:
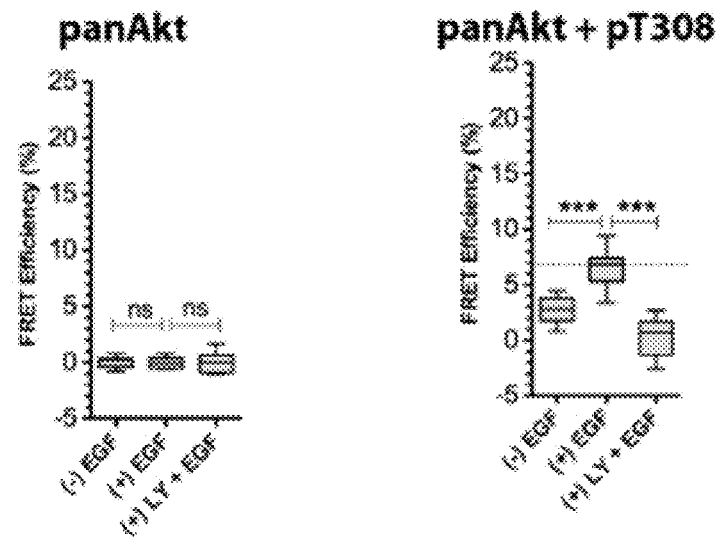
Figure 5B:
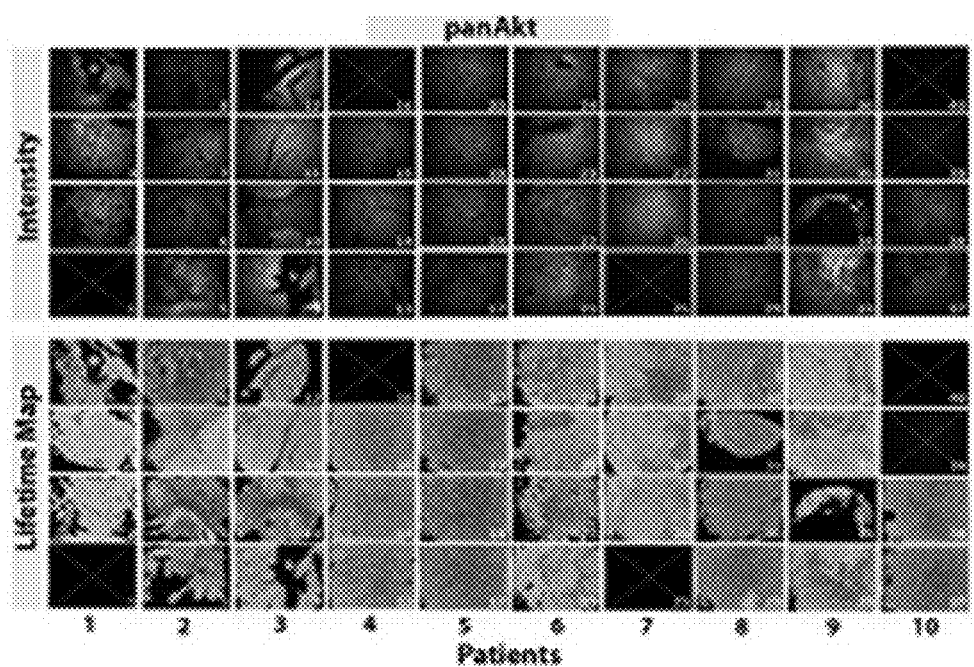
Figure 5C:
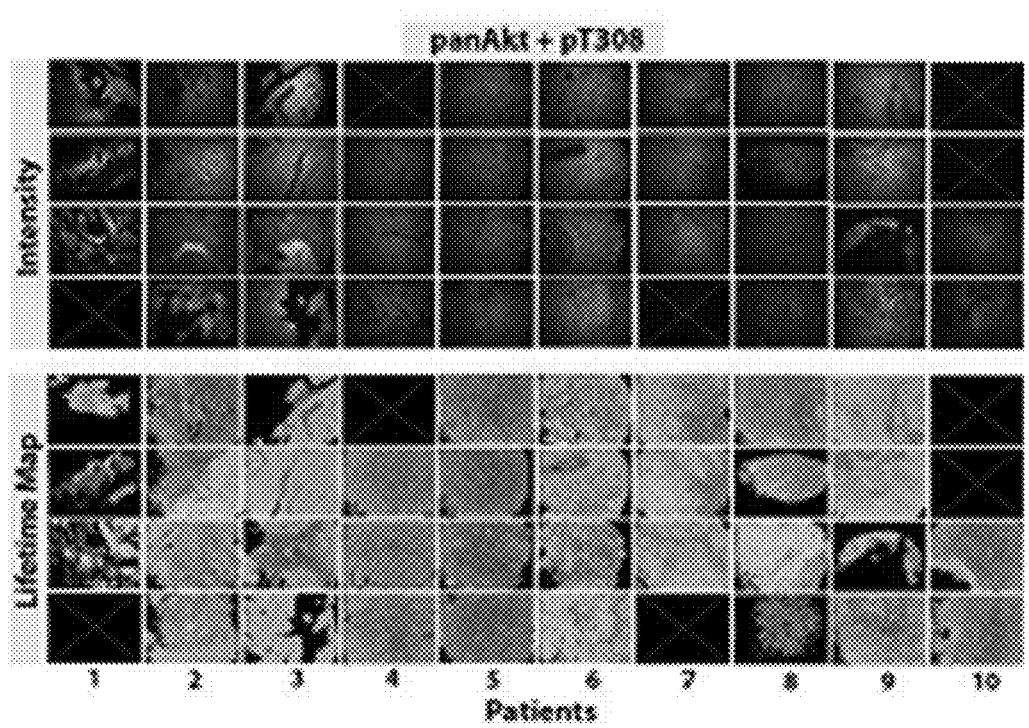

FLIM analysis of the donor only-labeled TMA showed averaged FRET efficiencies of zero for all cores (FIG. 5(b)). Lifetime analysis (using 4 matched ROI) of the donor plus acceptor sample showed increased average FRET efficiencies in some tumour cores (e.g. core 2, 3, 30) (FIGS. 5(c) and (d)). FIG. 3a illustrates the FRET efficiency calculated for 4 different ROIs per core. The maximum FRET efficiency value (Ef=23%) value from 4 ROIs is shown in FIG. 5(d).

These results demonstrate the variability of the FRET efficiency between 4 cores of the same patient sample (FIG. 5(d)). Averaging the FRET efficiency of the 4 cores resulted in a loss of localized information reported on the activation status of Akt (FIG. 5(e)).

These results demonstrated the coexistence of high and low FRET efficiencies in cores from the same patient biopsy, demonstrating molecular heterogeneity of the activation status of Akt within breast tumours. Hence analysis of localized FRET efficiencies is critical in breast tumours in order to avoid loss of valuable information.

Example 13—High-Throughput Two-Site TSA-FRET Quantification of Akt Activation and its Molecular Heterogeneity in Human Colon Cancer In order to test the TSA-FRET assay further and quantify the activation status of Akt and its molecular heterogeneity in other tumour types, a colon TMA was prepared from 7 patients. From each patient 4 cores were spotted (see FIG. 6(a)) from different regions within each tumour biopsy and in total there were 28 cores on each TMA. H&E staining was performed to confirm that each core contained tumour tissue (FIG. 6(a)). The same procedure was followed for the breast TMAs described above.

Figures 6A, 6B, 6C:
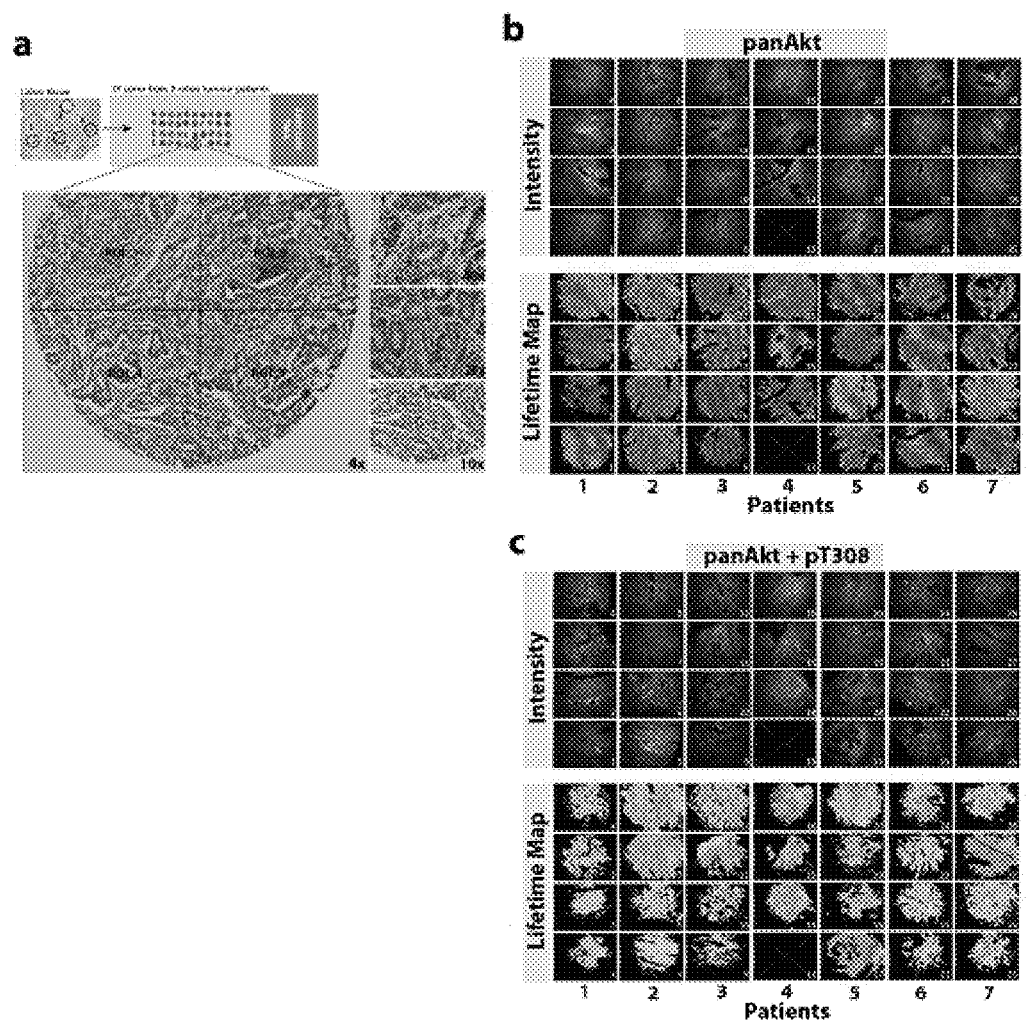
FIG. 6(a) shows H&E staining for breast tumour microarrays. The TMAs were prepared from colon tumour biopsies obtained from 7 patients. For each patient, 4 cores (circles 1 to 4) were selected from different regions within each biopsy. In total 28 tumour cores (4×7 patients) were spotted on each colon TMA. The lower image shows an expanded view of one core that can be divided in 4 regions of interest (ROI) for further analysis. The panels on the right show 3 different magnifications of the same region of the core.
FIG. 6(b) shows intensity images and lifetime maps of the TMAs stained with panAkt primary antibody only, followed by the TSA signal amplification labeling (donor alone).
FIG. 6(c) shows intensity images and lifetime maps of the corresponding TMAs (duplicate of the cores used for the labelling of the donor alone labeled with panAkt+pT308 primary antibodies, followed by the TSA signal amplification labeling (donor+acceptor). Using a purpose-built automated FLIM algorithm, the TMA were mapped for each tumour core position on the donor (panAkt) TMA slide and on the corresponding donor plus acceptor (panAkt+pT308) TMA slide.

FIGS. 6(b) and 6(c) show the intensity and the corresponding lifetime images for donor and donor plus acceptor labeled samples, respectively. The maximum FRET efficiency of each tumour core was calculated using the Excel-macro. Lifetime analysis of the donor only TMA showed averaged FRET efficiencies of zero (FIG. 6(c)).

Lifetime analysis of the donor plus acceptor TMA showed increased FRET efficiencies in tumour cores 3, 5 and 7 (FIGS. 6(c) and (d)). FIG. 6(a) illustrates the FRET efficiency calculated for 4 different ROIs per core. The maximum FRET efficiency (Ef=11%) value from 4 ROIs is shown in FIG. 6(d). In colon tumours the heterogeneity seems to be less than that of breast samples, nevertheless these results demonstrated the coexistence of high and low FRET efficiencies in cores from the same patient biopsy (FIG. 6(d)), demonstrating molecular heterogeneity of the activation status of Akt within colon tumours. In this case as well we suggest that the analysis of localized FRET efficiencies is critical in colon tumours in order to avoid loss of potentially valuable information.

Example 14—High-Throughput Quantification of Akt Activation in a Broad Case Mix from Breast Cancer Patients This case study analysed the activation status of Akt in a blind broad case-mix obtained from the tumour bank at King's Health Partners Tumour Bank. A total of 120 cores were prepared for the analysis. The distribution of these tumours were ductal no special type (NST), lobular, grade-1, grade-2, and grade-3 tumours. There were ER-positive cores, ER-negative cores and cores from node negative patients as shown in Table 2 below:

TABLE 2

| Cores (Patients) | ER Status |
| --- | --- |
| 20 | + |
| 24 | + |
| 47 | + |
| 74 | + |
| 61 | + |
| 118 | + |
| 121 | + |
| 59 | + |
| 19 | + |
| 50 | T |
| 45 | + |
| 95 | + |
| 69 | + |
| 83 | + |
| 35 | + |
| 37 | + |
| 84 | + |
| 86 | + |
| 68 | + |
| 53 | + |
| 82 | + |
| 51 | + |
| 42 | + |
| 36 | + |
| 31 | + |
| 72 | + |

TABLE 2-continued

| Cores (Patients) | ER Status |
|---|---|
| 22 | + |
| 28 | + |
| 57 | + |
| 43 | + |
| 27 | + |
| 29 | + |
| 32 | + |
| 89 | − |
| 75 | − |
| 81 | − |
| 14 | − |
| 41 | − |
| 21 | − |
| 23 | − |
| 111 | − |
| 76 | − |
| 30 | − |
| 62 | − |
| 56 | − |
| 11 | − |
| 96 | Na |
| 107 | Na |
| 105 | Na |

Figure 7A:
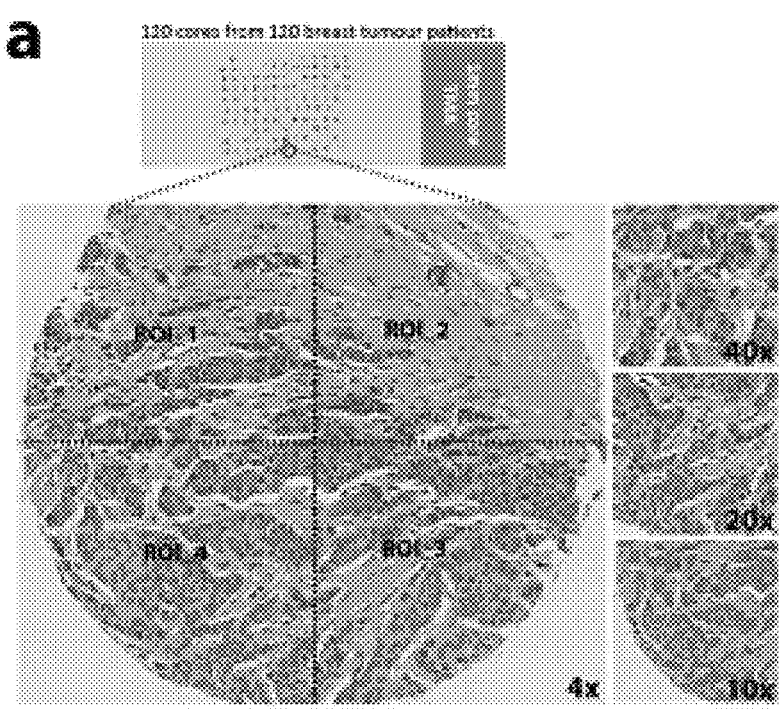
FIG. 7(a) shows H&E staining for breast tumour microarrays. This breast TMA contains many small representative tissue samples from 120 different patients assembled on a single histologic slide. The lower image shows an expanded view of one core that can be divided in 4 regions of interest (ROI) for further analysis. The panels on the right show three different magnifications of the same region of the core.

Presence of tumourous tissue (>50%) was confirmed by H&E staining for each breast TMA (FIG. 7(a)). The TMAs were fixed and stained according to the TSA-FRET protocol described above. FLIM was used to map and acquire lifetime images from each tumour core position (FIG. 7(a)).

Figure 7B:
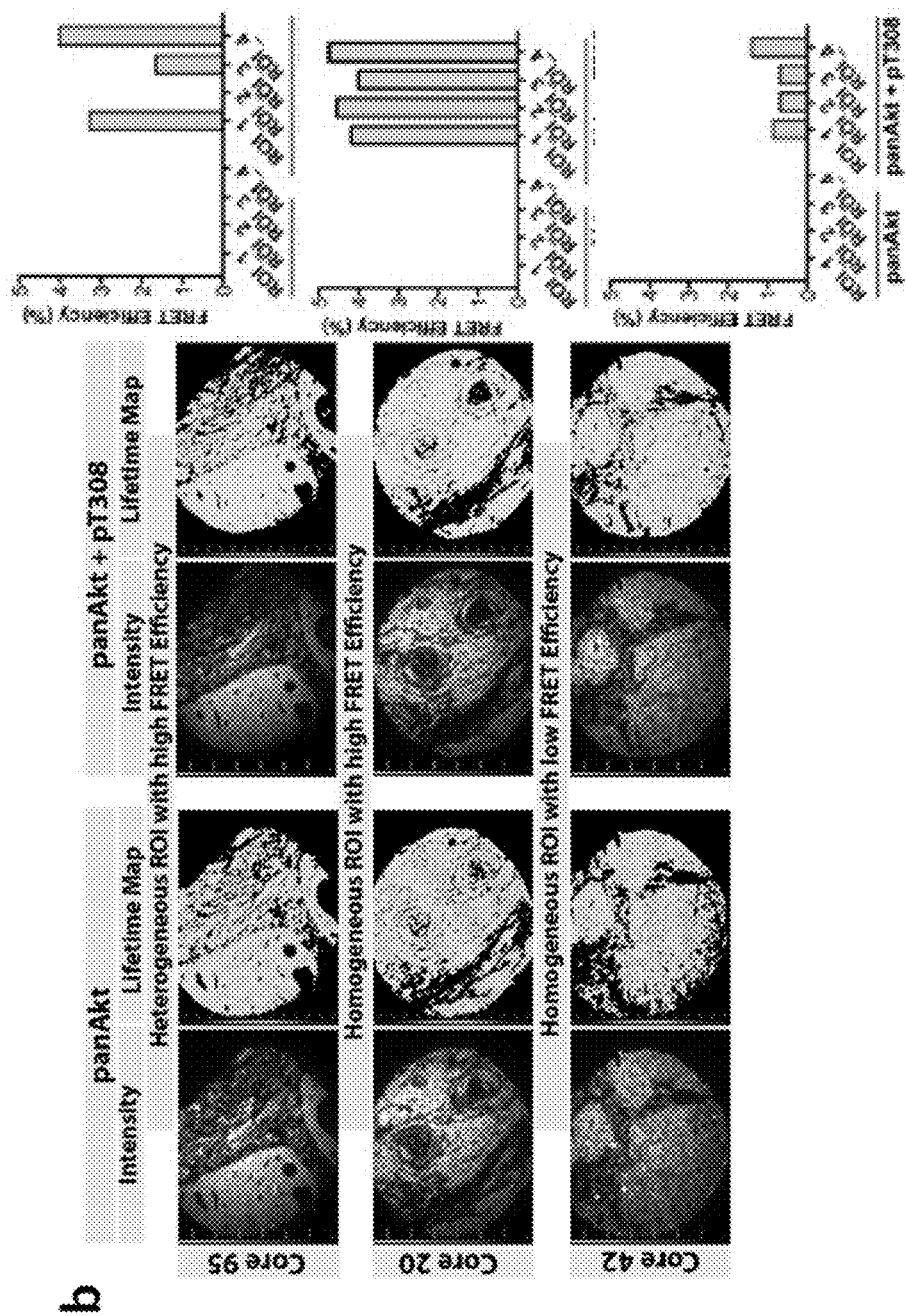
FIG. 7(b) shows intensity images and lifetime maps of the TMAs stained with panAkt only or with panAkt+pT308 primary antibodies (on a duplicate TMA), followed by the TSA signal amplification labeling (donor alone or donor+acceptor). Using a purpose-built automated FLIM algorithm the TMA were mapped for each tumour core position on the donor (panAkt) TMA slide and on the corresponding donor plus acceptor (panAkt+pT308) TMA slide. The three graphs present the variability of FRET efficiency within the 4 ROI of the same patient core and within different patient cores.
Figure 7C:
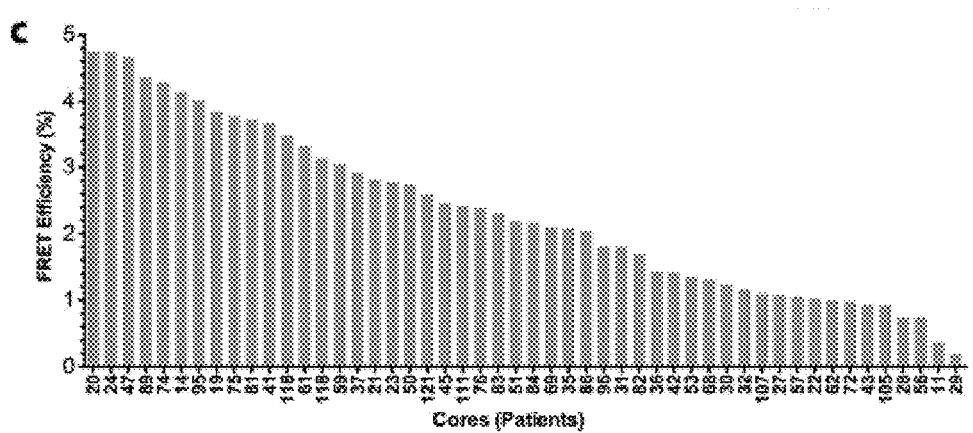
FIG. 7(c)—the graph shows the maximum value of FRET efficiency of the 4 ROIs/patient.
Figure 8:
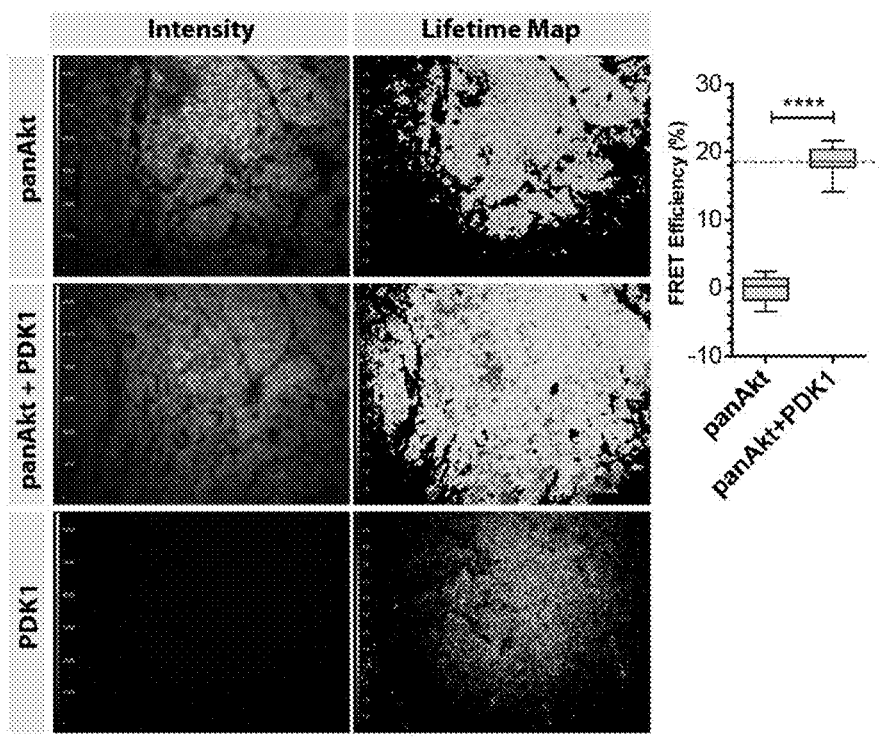
FIG. 8 shows the evaluation of PKB and PDK1 interaction in Triple Negative human breast xenografts, using PDK1 antibody (aa350-436) from LS-Bio rabbit polyclonal (specificity verified in FFPE) and panAkt monoclonal (SKB1) mouse from Millipore, specificity verified in FFPE). Both above primary antibodies were incubated on tissues for 16 h at 4° C. For TSA-FRET the PDK1 was labeled with rabbit Fab-T-ALX594 as acceptor and panAkt was labeled with mouse Fab-ORG488 as donor.

The donor labelled TMA showed averaged FRET efficiencies of zero for all samples. FIG. 7(b) shows the donor plus acceptor TMA and the variability of FRET efficiency between the 4 sectors of the same patient core and between different patient cores including samples with low (Ef=0.9%) and high (Ef=4.5%) FRET efficiency. The differences in the Akt activation status of histologically homogenous and heterogeneous samples are shown in FIG. 6b. Once again the heterogeneity in the activation status of Akt was observed in these tumours. FIG. 7(c) illustrates the FRET efficiency of each tumour core (patient), which range from a high FRET efficiency of 4.8% to a low FRET efficiency of 0.09% indicating the high dynamic range of the two-site TSA-FRET assay.

Importantly, the automated algorithms enabled the rapid acquisition and analysis of over 120 TSA-FRET images with minimal human intervention, removing a large amount of human error and subjectivity from the sample analysis.

Using two-site TSA-FRET, Akt activation and its heterogeneity in tumour sections and cells can be quantified with a high dynamic range, in a high-throughput objective manner.

Example 15—Quantification of Endogenous Protein-Protein (PKB+PDK1) Interaction

The interaction of PKB and PDK1 was evaluated in triple negative human breast xenografts using PDK1 antibody (aa350-436) from LS-Bio #ls-b1733 rabbit polyclonal (specificity verified in FFPE) and panAkt mouse monoclonal (SKB1) from Millipore (specificity verified in FFPE).

Both primary antibodies were incubated on tissues for 16 hours at 4° C. For secondary antibody staining, the PDK1 was labelled with rabbit Fab-TSA-ALX594 as FRET acceptor and panAkt was labelled with mouse Fab-ORG488 as FRET donor.

Figure 11:
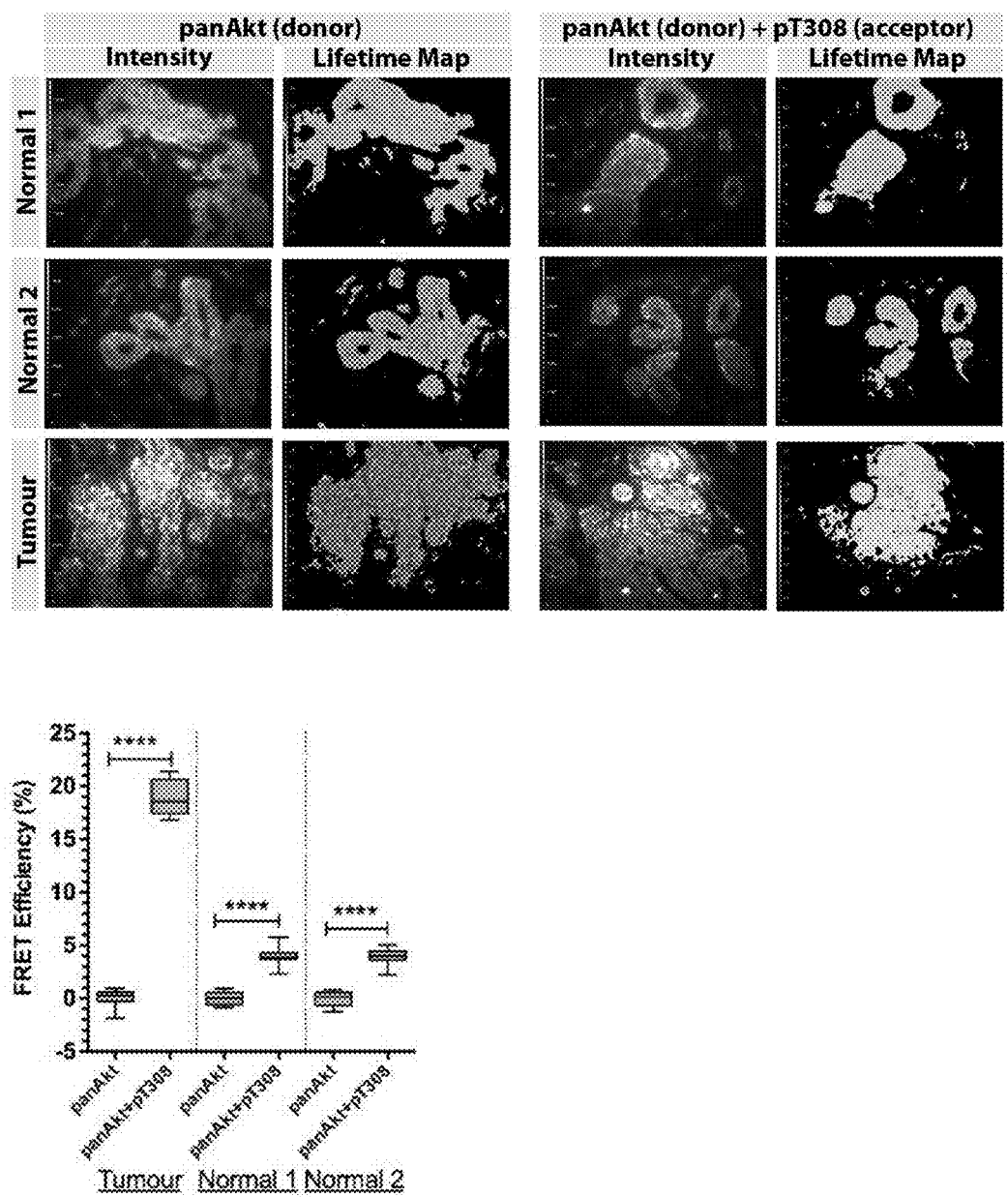
FIG. 11 shows quantification of endogenous pAkt (pT308) in fixed FFPE human normal and tumour breast tissue using amplified FRET. This Figure provides intensity images and lifetime maps of FFPE human breast tissues from two different normal (normal 1, normal 2) tissues and one tumour tissue labelled with donor alone (panAkt) or donor/acceptor (panAkt+pT308).

The results illustrate that the average lifetimes of Akt(pan) alone was 3.08 ns. The lifetimes significantly decrease (2.51 ns) in the presence of acceptor (PDK1-T-ALX594) indicating strong binding of PKB with PDK1. The decrease in donor lifetime by FRET was significant (****, P<0000.1) (FIG. 11).

The results demonstrate that the TSA-FRET assay of the present invention can be used to quantify the endogenous protein-protein (PKB+PDK1) interaction in PPFE fixed human breast tumour sections.

Figure 9A:
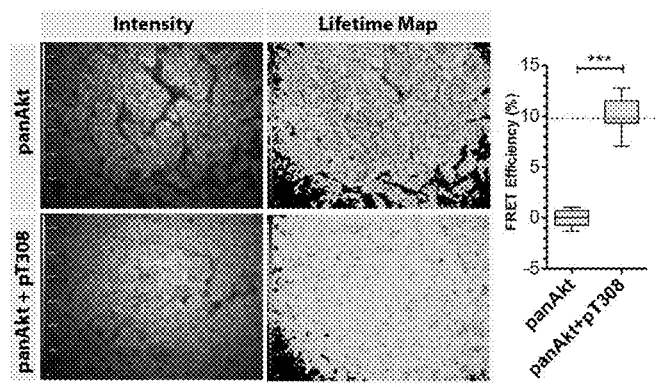
FIG. 9(a) shows TSA-FRET using Fab IgG (mouse and rabbit) stained simultaneously for quantification of pAkt (pT308) in human breast FFPE tissues. Primary antibodies against panAkt and pT308 were added simultaneously to the human breast tumour FFPE tissue. The next day the Fab-IgG secondary antibodies (mouse and rabbit) were added sequentially followed by TSA amplification.

Example 16—Sequential Versus Simultaneous Application of the Primary and Secondary Antibodies Primary antibodies against panAkt and pT308 were added simultaneously to the human breast tumour FFPE tissue. The next day the Fab-IgG secondary antibodies (mouse and rabbit) were added simultaneously followed by TSA amplification. Using this method 10% FRET efficiency with significant (***, P<0000.1) pT308 activation was obtained (FIG. 9(a)).

Figure 9B:
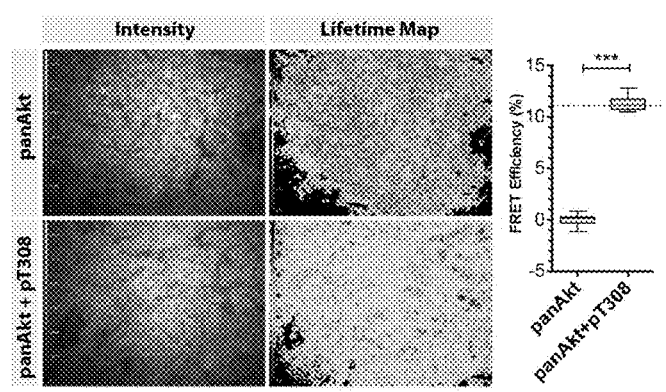
FIG. 9(b) shows TSA-FRET using Fab IgG (mouse and rabbit) stained sequentially for quantification of pAkt (pT308) in human breast FFPE tissues. Primary antibodies against panAkt and pT308 were added sequentially to the human breast tumour FFPE tissue. The next day the Fab-IgG secondary antibodies (mouse and rabbit) were added sequentially followed by TSA amplification.

Primary antibodies against panAkt and pT308 were added sequentially to the human breast tumour FFPE tissue. The next day the Fab-IgG secondary antibodies (mouse and rabbit) were added sequentially followed by TSA amplification. Using this method 11% FRET efficiency with significant (***, P<0000.1) pT308 activation was obtained. By adding the Fab-IgG sequentially the results showed there was no significant difference in FRET efficiency (FIG. 9(b)).

FIG. 10 shows confocal images for Fab-IgG with TSA-FRET. Confocal image analysis for panAkt and pT308. showed clear co-localization of panAkt and pT308. However, there was no difference in the intensity between Fab-IgG simultaneous experiment and sequential experiment. Control experiments with no primary antibody showed no staining pattern.

Other non-FRET coincidence assays that quantify protein complex formation or posttranslational protein modifications, such as the in situ proximity ligation assay (PLA), detect molecules within 30-40 nm of one another. The in situ PLA method was tested in fixed SKBR3 cells and FFPE breast tumour to quantify the activation status of pT308. Akt activation was detected in SKBR3 cells (data not shown) but not in FFPE breast tissue It is anticipated that Akt activation was not quantified in FFPE breast tissue due to the low dynamic range of in situ PLA and the non-specific background created by this methodology in tissue samples.

In contrast, the aforementioned results show that the methods of the invention can map and quantify the molecular heterogeneity of the Akt pathway in SKBR3 cells and FFPE breast tissue. The methods of the invention can also detect the molecular heterogeneity of Akt activation within breast tumours and colon tumours. The methods of the invention can detect molecular heterogeneity of onco-protein activation between different cores taken from the same biopsy as well as between patients, demonstrating the quantitative dynamic range of FRET efficiencies measurable by the methods of the present invention.

The methods of the invention can be applied to the quantification of the activation status of other protein biomarkers, as well as evaluating protein-protein interaction in tumours.

Example 17—Quantification of Endogenous pAkt (pT308) in Fixed FFPE Human Normal and Tumour Breast Tissue Using Amplified FRET The methods described above were used to compare endogenous Akt activation in human normal and tumour breast tissue.

FIG. 11 provides intensity images and lifetime maps of FFPE human breast tissues from two different normal (normal 1, normal 2) tissues and one tumour tissue labelled with donor alone (panAkt) or donor/acceptor (panAkt+pT308).

FRET efficiencies are shown as box and whiskers plots representing mean±SEM for at least 10 different regions from the same tissue section (****, p<0.0001).

The increased FRET efficiency observed represents the phosphorylation status of endogenous Akt and shows the differential activation of pT308 in normal and tumour tissue patients.

The results confirm that the two-site TSA-FRET assay of the invention is a highly sensitive and specific assay for the detection of molecular heterogeneity that benefits from a high and quantifiable dynamic range, which allows accurate quantification and comparison of different tissue samples.

This confirms that the two-site TSA-FRET assay of the invention can accurately assist in determining whether a disease state exists in a tissue sample, allowing an effective diagnosis to be made in a patient, and a treatment course initiated, if necessary.

Example 18—Use of Amplified FRET Method for Stratifying p-Akt/ER+/ER− Samples

The methods of the invention can be used for the stratification of patients. In particular, the prognostic value of pAkt expression in human breast cancers was assessed by high-throughput amplified FRET versus intensity based IHC.

Previous studies have attempted to determine the prognostic value of Akt activation in breast cancer using IHC, with varying results (7, 33). The inventors obtained TMAs representing 164 primary human breast tumors representative of breast cancer subtypes treated in tertiary referral centers. The amplified FRET/FLIM methods of the present invention and also the IHC intensity ratio were used to investigate whether pAkt might be associated with poor prognosis in order to demonstrate the validity of both methods. A previous study (33) demonstrated that high levels of pAkt assessed by IHC failed to demonstrate prognostic value in breast cancer patients before hormone therapy (33). Consistent with these findings, the inventors results using the IHC intensity ratio in breast TMAs did not show an association between Akt activation and DFS or OS (FIG. 13b and FIG. 13d).

However, contrary to these limited methodologies, coincidence amplified FRET methods of the present invention show that in primary breast TMAs there was a significant difference between high and low pAkt groups in terms of DFS and OS. This applies to the total group of 230 patients (comprising ER(+) and ER(−)) (FIG. 13 a), as well as for the 125 ER(+) patients (FIG. 13c). The coincidence amplified FRET assay therefore, allows biomarker activation to be assessed compared to traditional IHC. Tamoxifen is one of the most commonly used drugs to treat ER+ breast cancer. Dysregulation of the PI3K/Akt pathway plays a vital role in tamoxifen drug resistance by promoting cell proliferation and survival.

In the present methodology, the prognostic value of pAkt was assessed in primary breast carcinoma and the results compared with intensity based IHC (calculated as the intensity ratio of pT308 divided by panAkt). A broad case mix of tumour samples representing 230 patients was obtained from King's Health Partners Tumour Bank in TMA format, with linked 15-year follow-up clinical data. The case mix consisted of 76% of tumours ER+ and 24% ER(−) with a mix of grade-1, grade-2, and grade-3 tumours, as shown in Table 3 below.

The presence of tumour tissue (>50%) was confirmed by H&E staining for each breast tumour core (FIG. 12a). The TMAs were fixed and stained according to the methods described above.

Using the automated FLIM platform images were mapped and acquired from each tumour core position. The software enabled the rapid acquisition and analysis of 230 tumour cores with minimal intervention, thereby removing a large amount of human error and subjectivity from the sample analysis.

The differences in Akt activation status of histologically homogeneous and heterogeneous samples can be appreciated in FIG. 12b (right panel). Normal breast tissue was used to assess the basal FRET efficiency as a negative control. The basal FRET efficiency values ranged from 2.3% to 5.7% with median average FRET efficiency of 4% (FIG. 11). FIG. 12b (bar graphs) shows the variability of FRET efficiency between the 4 sectors from the same patient, as well as between different patient cores, ranging from low (3.9%) to a high (25.1%) FRET efficiency.

FIG. 12c illustrates the maximum FRET efficiency of each tumor core, arranged from high (27.8%) to low (0.5%), indicating the high dynamic range of the amplified FRET assay. The inventors investigated whether there was a relationship between pAkt status assessed by amplified FRET (black dots) and by intensity ratio (gray dots). The linear regression showed there was no correlation between the two methods.

TABLE 3

Patient characteristics for breast TMA samples and mean FRET efficiency.

| | |
|---|---|
| Median Age | 57.0 |
| Median FRET efficiency | 11.8 |
| Median Intensity ratio (Pt308/panAkt) | 1.7 |
| Grade | % |
| Grade1 | 17.1 |
| Grade2 | 31.7 |
| Grade3 | 42.7 |
| Unknown | 7.9 |
| ER | % |
| ER+ | 76.2 |
| ER− | 22.0 |
| Unknown | 1.8 |
| PR | % |
| PR+ | 55.5 |
| PR− | 42.7 |
| Unknown | 1.8 |
| HER2 | % |
| HER2+ | 9.1 |
| HER2− | 37.2 |
| Unknown | 53.7 |
| Adjuvant Therapy | % |
| Adjuvant therapy (total) | 86.0 |
| Tamoxifen | 62.8 |
| CMF + Tamoxifen | 12.8 |
| CMF | 8.5 |
| None | 5.5 |
| EFC | 3.7 |
| Ov Abl + Tamoxifen | 2.4 |
| FEC + Tamoxifen | 2.4 |
| Ov abl | 1.2 |
| APD | 0.6 |
| Surgery | % |
| Mastectomy | 44.5 |
| Conservation | 55.5 |

TABLE 3-continued

Patient characteristics for breast TMA samples and mean FRET efficiency.

| Radiation Therapy | % |
|---|---|
| YES | 55.5 |
| NO | 44.5 |

Abbreviation:
epirubicin, cisplatin and continuous infusion 5-fluorouracil (ECF)
cyclophosphamide, methotrexate and 5-fluorouracil (CMF)
fluorouracil, epirubicin and cyclophosphamide (FEC)
aprepitant, palonosetron and dexamethasone (APD)

The inventors then evaluated the prognostic value of Akt activation assessed by amplified FRET compared to intensity ratio in 164 cases, consisting of 125 ER+ and 39 ER (−) tumors. Patients were ranked according to their FRET efficiency or intensity ratio, and split into two groups for comparison, upper tertile (high pAkt) and lower two tertiles (low pAkt). 15 years of clinical follow-up data was used to generate Kaplan-Meier plots for DFS and OS, in order to compare the two groups (FIG. 13). When assessed by amplified FRET, high pAkt significantly correlated with reduced DFS ($p=0.036$, HR=0.634, 95% CI [0.385-0.694]) and OS ($p=0.013$, HR=0.570, 95% CI [0.331-0.876]) compared to low pAkt (FIG. 13a). Importantly, when assessed by intensity ratio, high pAkt was not associated with reduced DFS ($p=0.890$, HR=0.699, 95% CI [0.616-1.521]) or OS ($p=0.746$, HR=1.082, 95%[0.670-1.750]) compared to low pAkt (FIG. 13b).

The inventors studied the ER+ subgroup separately (n=125), splitting this cohort into high and low pAkt groups as before. As shown in FIG. 13c, when assessed by amplified FRET, there was a significant association between high pAkt and reduced DFS ($p=0.029$, HR=0.566, 95% CI [0.299-0.936]) and OS ($p=0.033$, HR=0.284, 95% CI [0.284-0.946]). In contrast, using the intensity ratio, high pAkt was not associated with DFS ($p=0.800$, HR=0.932, 95% CI [0.535-1.618]) or OS ($p=0.759$, HR=1.098, 95% CI[0.607-1.983]) (FIG. 13d). Moreover, patient age (mean 60 years) did not appear to correlate with the poor DFS or OS (data not shown). Furthermore, 11 factors of potential prognostic significance were evaluated by univariate analysis, as shown in Table 4 below:

TABLE 4

Univariate analysis of factors associated with prognostic significance.

| Variable | p values (OS) | p values (DFS) |
|---|---|---|
| Histology Grade | 0.000 | 0.000 |
| DIAG No Path Nodes | 0.701 | 0.702 |
| ER Status | 0.066 | 0.116 |
| PR Status | 0.006 | 0.011 |
| HER2 Status | 0.327 | 0.634 |
| Tumour Size | 0.010 | 0.005 |
| Adjuvant Therapy | 0.009 | 0.003 |
| Surgery | 0.104 | 0.131 |
| Radiotherapy | 0.028 | 0.040 |
| Int. Ratio (A/D) | 0.218 | 0.248 |
| FRET tertiles | 0.041 | 0.149 |

The data analysis revealed that increased $E_f$ of pAkt associated with diminished OS ($p=0.041$) but not with intensity ratio ($p=0.218$, Table 4). In the univariate analyses, the histology grade was the most significant independent prognostic factor for DFS and OS. These findings show that FRET efficiency, as an indicator of Akt activation status, but not intensity ratio, predicts poorer disease-free and overall survival in patients with ER+ primary breast carcinoma.

These results highlight that, using the amplified FRET methods of the present invention (but not the IHC intensity ratio), high Akt activation in primary breast carcinoma predicts poorer outcome in these patients.

In particular, FIG. 13 shows that simply using the ratio of the intensities does not correlate with the outcomes. As can be seen from the Examples, a synergism results from utilisation of the methods of the invention, which provides an improved detection method. The results also enable improved stratification of patients.

The data in FIG. 13 confirms that enhanced Akt activation in primary breast carcinoma patients is associated with worse prognosis, indicating that increased cancer cell survival is contributing to tamoxifen resistance in this patient group.

Since the inventors have shown that high pAkt is associated with reduced survival, it is believed that patients with high pAkt are suitable candidates for targeted PI3K/Akt pathway inhibitors. This is now being tested in Phase II clinical trials in advanced breast cancers (For e.g. ClinicalTrials.gov Identifier: NCT01277757).

Akt activation was significantly higher in ER (−) than in ER (+) patients when assessed by coincidence amplified FRET methods of the present invention but not by IHC intensity ratio (FIGS. 13e and f). A higher proportion of ER (−) patients had high pAkt compared to the ER (+) patients (FIG. 13g). This result indicates that ER-independent signaling pathways are involved in the activation of Akt.

Additionally, amongst ER (−) patients, more than half exhibited high Akt activation, compared to one third of ER (+) patients (FIG. 13h). This indicates that the ER+ population may benefit from stratification based on a measured value of Akt activation. Currently ER (+) breast tumors are treated with hormone-based therapy—this could be supplemented with targeted Akt inhibition for those patients with high Akt activity. In contrast, stratification of ER (−) patients would allow the introduction of Akt inhibition to a subset of patients who, until now, have not had many targeted therapeutic options.

The novel coincidence FRET methods of the invention, which combine signal amplification with the flexibility of labelled secondary antibodies, provides a highly sensitive, specific and portable methodology for the quantification of low levels of endogenous protein activation in a wide range of signalling pathways.

In parallel, the high-throughput FRET/FLIM imaging platform described herein is capable of mapping TMAs, automatically acquiring images and processing FRET data, requiring minimal intervention from a non-specialist user.

Moreover, the methods of the present invention significantly shorten the time required to complete the analysis of multiple samples (e.g. 230 samples), compared with standard IHC techniques, which also require a pathologist to manually score a similar number of samples labelled with standard IHC techniques.

The studies show that in primary breast carcinoma, high Akt activation measured by amplified FRET methods of the present invention (but importantly, not by IHC intensity ratio) was correlated with poorer disease-free and overall survival. The methods of the present invention were able to quantify heterogeneity of Akt activation at two levels: i) between multiple cores taken from different regions of the same tumor (>2 mm range), and ii) between sectors of a single tumor core (<1 mm range). The methodology worked equally well when used to analyse other tissue types such as colon carcinoma.

This methods of the present invention are able to directly monitor Akt pT308 as a read-out of protein activation in both cells and FFPE breast tissue, and can be used more generally to monitor post-translational modifications or protein-protein interactions in any signaling pathway.

The ability to accurately quantify oncoprotein activation has several major implications for translational medicine, in particular: drug screening in tissue culture; the discovery and validation of prognostic and predictive biomarkers; patient stratification based on oncoprotein activation; and validating the mode of action of drug inhibition, for example during neo-adjuvant therapy or window trials.

Example 19—Use of Amplified FRET Method for Detection of Protein-Protein (HER2/HER3) Interaction The methods of the invention can be used for detecting protein-protein interaction. In this Example, HER2/HER3 interaction was measured using a Fab fragment based Tyramide Signal Amplification (TSA) assay.

HER2 and HER3 antibody specificity in HER2-overexpressing SKBR3 cells was measured by Western blot.

HER2-overexpressing SKBR3 cells were stimulated for 5 min with 25 ng/ml Heregulin (HRG). Whole-cell lysates from the SKBR3 cells were subjected to Western blotting for HER2 and HER3, with specific bands shown for both proteins.

FIG. 14a shows the results of the Western blot analysis using Cellsig, Dako and LSBio.

HER2 was labelled with anti-rabbit-ATTO488 Fab fragments (binds to Tyr aa1248) as the FRET donor (D). HER3 was labelled with anti-mouse TSA-ALX594 Fab fragments (binds around aa1175-1275) as the FRET acceptor (A).

Co-localisation of endogenous HER2 and HER3 was also measured in non-stimulated SKBR3 cells using confocal microscopy. Non-stimulated (non-starved) SKBR3 cells were fixed and labelled with antibodies for HER2 and HER3. HER2 was detected by anti-rabbit-ATTO488 Fab fragments. HER3 was detected by anti-mouse TSA-ALX594 using the amplification method of the present invention.

FIG. 14b shows the confocal microscopy results. The results show that HER2 localised at the plasma membrane, but HER3 was localised at both the plasma membrane and the cytoplasm but not in the nucleus.

The amplified FRET methods of the present invention were further used to detect endogenous HER2-HER3 dimerization in SKBR3 cells.

Non-stimulated SKBR3 cells were fixed and stained with HER2 and HER3 antibodies as described above. Again, HER2 was detected by anti-rabbit-ATTO488 Fab fragments. HER3 was detected by anti-mouse TSA-ALX594 using the amplification method of the present invention.

FIGS. 14c and d show the FRET efficiency ($E_f$) for donor (D) alone was 0 and donor-acceptor (DA) was 24% using FRET-FLIM analysis. This indicates that HER2 and HER3 are in a predimerized state. The $E_f$ was higher at the plasma membrane compared to the cytoplasm indicating that dimerization takes place mostly at the plasma membrane. The control slides with an unlabelled secondary antibody showed no non-specific labelling.

Further studies were performed to determine the co-localisation of endogenous HER2 and HER3 in SKBR3 cells stimulated with NRG1.

Starved (1 hr with 0% serum) SKBR3 cells were stimulated with NRG1 (10 ng/ml) for 5 minutes, fixed and stained with antibodies for HER2 and HER3 as described above. These were compared with Starved (1 hr with 0% serum) SKBR3 cells that were not stimulated with NRG1. Again, HER2 was detected by anti-rabbit-ATTO488 Fab fragments. HER3 was detected by anti-mouse TSA-ALX594 using the amplification method of the present invention.

FIG. 14e shows confocal image results from such analysis. The results again showed that HER2 localised at the plasma membrane and HER3 localised at both the plasma membrane and the cytoplasm with no nuclear localisation. The HER2 signal appeared to be homogenous at the plasma membrane in the non-NRG1 stimulated cells, whereas in the NRG1-stimulated cells, the HER2 signal appeared to be punctuated/ruffled. The HER3 signal appeared to be similar in both non-NRG1 stimulated cells and NRG1-stimulated cells.

FIGS. 14f and g show the FRET efficiency ($E_f$) for D alone was 0 and DA was approximately 15% using FRET-FLIM analysis. This indicates that HER2-HER3 are still in a dimerized state in the starved cells, but that following starvation, there is some depletion of HER2 and HER3 at the plasma membrane. There did not appear to be any NRG1-dependent change in $E_f$. $E_f$ was higher at the plasma membrane compared to the cytoplasm, indicating that dimerization occurs mostly at the plasma membrane.

HER2-HER3 dimerization in HER2 control slides was measured using the amplified FRET methods of the present invention.

Again, HER2 was detected by anti-rabbit-ATTO488 Fab fragments. HER3 was detected by anti-mouse TSA-ALX594 using the amplification method of the present invention.

FIGS. 14h and i show the FRET efficiency ($E_f$) using FRET-FLIM analysis. An optimal exposure time was used to obtain enough photons, with higher exposure time used in lower HER2-expressing cells. The lifetime (approximately 2.7 ns) of D (ATTO488) labelled slides did not change significantly across the different HER-2 expressing samples.

Figure 14I:
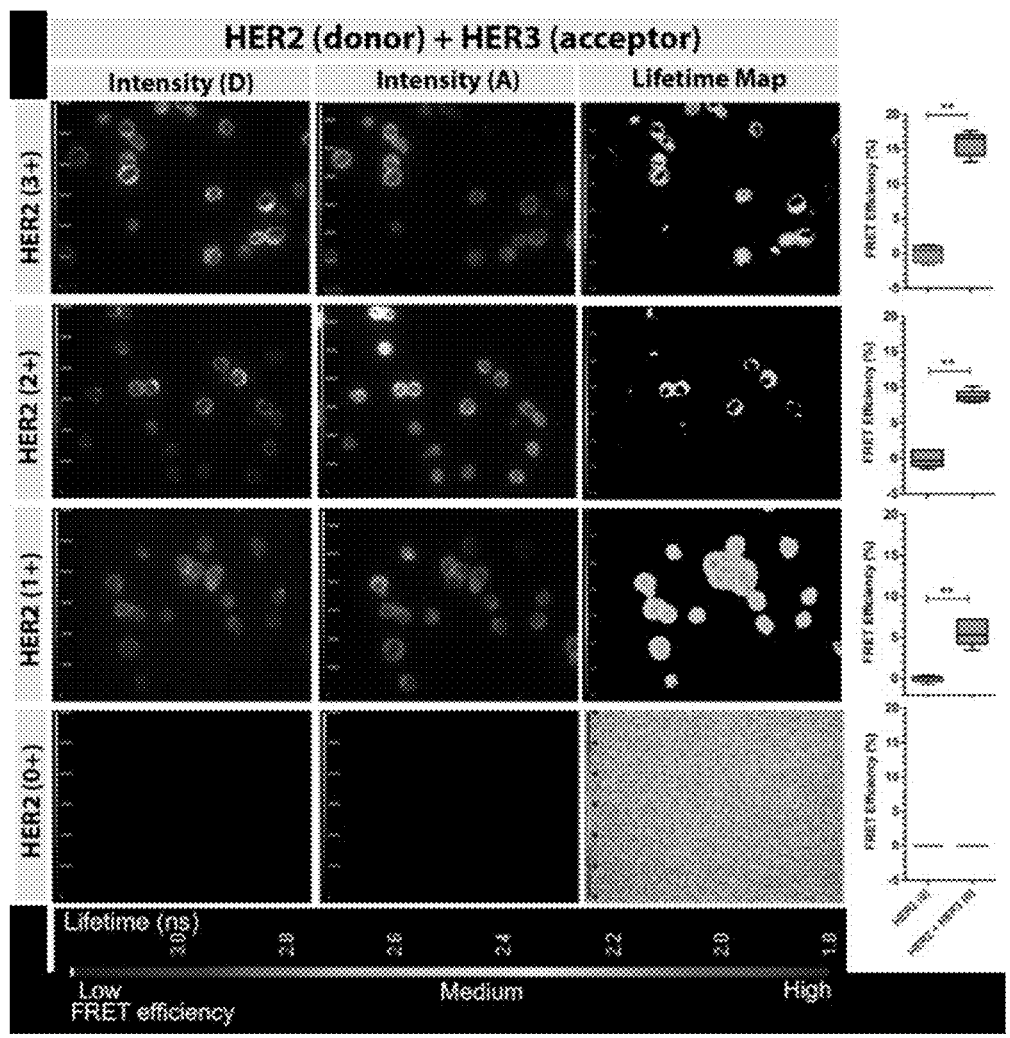

FLIM on DA stained slides showed a differential $E_f$ and was highly correlated with HER2 expression as shown in FIG. 14i, indicating that greater HER2-HER3 dimerization occurs with increasing HER2 expression. The HER2(0) slide showed no labelling of HER2, therefore $E_f$-calculations were not possible. This further confirmed the specificity of the anti-HER2 antibody.

Thus, the above Example shows that the methods of the present invention can be used to detect protein-protein interactions.

Example 20—Use of Amplified FRET Method for Detection of Protein-Protein (HER2/HER3) Interaction in Breast Cancer Tissue The methods of the invention can be used in detecting HER2-HER3 interaction in normal breast tissue and breast cancer tissue.

To evaluate HER2-HER3 dimerization in normal breast tissue and breast cancer tissue in a high throughput manner, TMA BRC961 was obtained from US Biomax.

BRC961 consists of 96 cores (total of 48 cases), with duplicates of 36 cases of common types of breast carcinoma and 12 cases of normal and other malignant breast tissue. All the cores had AR/ER/PR/Her-2 IHC results.

The amplified FRET methods of the present invention were used to detect co-localization of endogenous HER2-HER3 in human breast tissue (TMA BRC961 was obtained from US Biomax).

FIG. 15a shows confocal images of this study. The images showed frequent region-specific co-localization of HER2 and HER3 expression (see, for example, Core 1) and the absence of HER2 as expected in some cores (see, for example, Core 3). Only a few cores contained very few epithelial cells (see, for example, Core 2), which may be due to the presence of significant fat tissue.

HER2 labelling matched the majority of the HER2 immunohistochemistry (IHC) results mentioned above. In some of the normal tissue cores there was a medium HER2 intensity detected by the method of the present invention, which was also supported by HER2++ IHC scoring, as shown in Table 5 below:

TABLE 5

| TMA_FLM | DA_Intensity | A_Intensity | FRETef (%) | Her2 | Type | Grade |
|---|---|---|---|---|---|---|
| C10 | 4824 | 35058 | 12.42 | ++~+++ | Malignant | II |
| G2 | 5526 | 48834 | 12.15 | +++ | Malignant | II~III |
| H2 | 4502 | 42291 | 11.99 | +++ | Malignant | II~III |
| G8 | 5495 | 40086 | 10.92 | +++ | Malignant | III |
| D10 | 3426 | 32718 | 9.90 | ++~+++ | Malignant | II |
| D5 | 7768 | 17380 | 8.16 | +++ | In Situ | I |
| F2 | 6606 | 25065 | 8.16 | +++ | Malignant | II |
| G6 | 8453 | 22050 | 8.04 | +++ | Malignant | II~III |
| G7 | 1833 | 34239 | 7.09 | +~++ | Malignant | II~III |
| H8 | 5251 | 18466 | 6.99 | +++ | Malignant | III |
| F6 | 9813 | 23232 | 6.94 | +++ | Malignant | III |
| F1 | 5548 | 15609 | 6.83 | +++ | Malignant | II~III |
| H6 | 7217 | 14453 | 6.67 | +++ | Malignant | II~III |
| D11 | 10684 | 17832 | 6.32 | +++ | Malignant | II |
| E6 | 8575 | 22822 | 6.29 | +++ | Malignant | III |
| F12 | 8725 | 28659 | 6.16 | ++~+++ | Malignant | II |
| C5 | 9123 | 17380 | 6.03 | +++ | In Situ | I |
| E1 | 6243 | 25643 | 5.99 | +++ | Malignant | II~III |
| C11 | 9831 | 15295 | 5.94 | +++ | Malignant | II |
| H7 | 2114 | 28007 | 5.84 | +~++ | Malignant | II~III |
| E12 | 7190 | 20647 | 5.82 | ++~+++ | Malignant | II |
| C1 | 5019 | 4494 | 5.48 | +~++ | Sarcoma | |
| E2 | 6150 | 21171 | 4.93 | +++ | Malignant | II |
| D8 | 1399 | 991 | 4.56 | + | Malignant | III |
| A2 | 3159 | 10926 | 3.83 | ++ | Normal | |
| G4 | 2584 | 17380 | 3.70 | +— | Malignant | II~III |
| B10 | 5782 | 5781 | 3.34 | + | Benign | |
| F7 | 2616 | 5225 | 3.14 | + | Malignant | II~III |
| H11 | 1765 | 1655 | 2.67 | +~++ | Malignant | |
| E3 | 2899 | 6608 | 2.61 | − | Malignant | III |
| D12 | 3286 | 5522 | 2.60 | + | Malignant | II~III |
| F11 | 2644 | 23337 | 2.53 | − | Malignant | II |
| E11 | 2408 | 18652 | 2.52 | − | Malignant | II |
| C3 | 4969 | 20546 | 2.41 | ++~+++ | In Situ | I |
| B9 | 6647 | 6404 | 2.27 | + | Hyperplasia | |
| C8 | 2873 | 24547 | 1.96 | + | Malignant | III |
| G12 | 2330 | 16259 | 1.94 | − | Malignant | III |
| A10 | 5281 | 10240 | 1.70 | + | Benign | |
| B1 | 3077 | 8111 | 1.69 | − | Normal | |
| G11 | 4159 | 2332 | 1.69 | +~++ | Malignant | |
| C6 | 4813 | 20842 | 1.68 | + | Malignant | I~II |
| B12 | 1773 | 6689 | 1.67 | + | Benign | |
| B2 | 5772 | 8090 | 1.63 | ++ | Normal | |
| A8 | 3431 | 8132 | 1.63 | + | Hyperplasia | |
| E5 | 3194 | 17380 | 1.60 | − | Malignant | III |
| A5 | 2746 | 17380 | 1.57 | − | Hyperplasia | |
| C2 | 6559 | 7590 | 1.36 | ++~+++ | In Situ | I |
| G10 | 5362 | 19347 | 1.32 | + | Malignant | II~III |
| D9 | 2070 | 13147 | 1.32 | − | Malignant | II~III |
| A12 | 2785 | 11698 | 1.29 | + | Benign | |
| C9 | 2434 | 9777 | 1.29 | − | Malignant | II~III |
| F3 | 1629 | 3258 | 1.29 | − | Malignant | III |
| B5 | 2113 | 17380 | 1.27 | − | Hyperplasia | |
| H5 | 1213 | 6334 | 1.07 | − | Malignant | II |
| D3 | 4569 | 11619 | 1.03 | ++~+++ | In Situ | I |
| E9 | 2501 | 8283 | 1.02 | +— | Malignant | I~II |
| F4 | 1748 | 17380 | 1.02 | − | Malignant | I~II |
| D2 | 5817 | 5272 | 1.01 | ++~+++ | In Situ | I |
| B8 | 3965 | 20790 | 0.99 | + | Hyperplasia | |
| C12 | 4069 | 4998 | 0.99 | + | Malignant | II~III |
| B4 | 2498 | 18397 | 0.99 | − | Hyperplasia | |
| A9 | 3648 | 10143 | 0.97 | + | Hyperplasia | |
| E7 | 2639 | 8885 | 0.96 | + | Malignant | II~III |
| H1 | 6854 | 3440 | 0.73 | +++ | Malignant | III |
| G1 | 7284 | 2914 | 0.68 | +++ | Malignant | III |

TABLE 5-continued

| TMA_FLM | DA_Intensity | A_Intensity | FRETef (%) | Her2 | Type | Grade |
|---|---|---|---|---|---|---|
| A7 | 1774 | 2422 | 0.67 | − | Hyperplasia | |
| F10 | 3400 | 12156 | 0.66 | + | Malignant | III |
| B7 | 2017 | 8041 | 0.66 | − | Hyperplasia | |
| H12 | 2829 | 21767 | 0.66 | − | Malignant | III |
| C4 | 6103 | 18397 | 0.66 | + | In Situ | I~II |
| G9 | 6113 | 2074 | 0.66 | ++~+++ | Malignant | IIII |
| H3 | 2579 | 21262 | 0.66 | + | Malignant | II~III |
| A4 | 3224 | 11109 | 0.65 | − | Hyperplasia | |
| A11 | 3321 | 10803 | 0.65 | +− | Benign | |
| A6 | 3651 | 11536 | 0.64 | − | Hyperplasia | |
| B6 | 3285 | 11807 | 0.64 | − | Hyperplasia | |
| A1 | 2428 | 11944 | 0.37 | − | Normal | |
| A3 | 2326 | 11527 | 0.36 | − | Normal | |
| D4 | 4486 | 18397 | 0.34 | + | In Situ | I~II |
| C7 | 3954 | 9741 | 0.34 | + | Malignant | II |
| E4 | 2876 | 17380 | 0.34 | − | Malignant | I~II |
| B3 | 1332 | 18397 | 0.33 | − | Normal | |
| D6 | 4594 | 17374 | 0.33 | + | Malignant | I~II |
| F8 | 2169 | 35843 | 0.33 | − | Malignant | II |
| F9 | 1688 | 12431 | 0.33 | +− | Malignant | I~II |
| G3 | 3029 | 38730 | 0.33 | + | Malignant | II~III |
| H4 | 2777 | 17380 | 0.33 | +− | Malignant | II~III |
| E10 | 2517 | 13475 | 0.32 | + | Malignant | III |
| B11 | 2140 | 12893 | 0.00 | +− | Benign | |
| D1 | 4315 | 8572 | 0.00 | +~++ | Sarcoma | |
| D7 | 4075 | 9256 | 0.00 | + | Malignant | II |
| E8 | 2794 | 47059 | 0.00 | − | Malignant | II |
| F5 | 3713 | 17380 | 0.00 | − | Malignant | III |
| G5 | 3528 | 9491 | 0.00 | − | Malignant | II |
| H9 | 3035 | 1344 | 0.00 | ++~+++ | Malignant | III |
| H10 | 3109 | 19001 | 0.00 | + | Malignant | II~III |

HER3 was expressed at high levels in most of the cores.

Table 5 above provides $E_f$ values for all TMA cores with HER2 (DA) and HER3 (A) intensity data. The TMA cores were sorted based on high to low $E_f$.

FIG. 15b shows that high $E_f$ correlated with HER2+++ IHC scoring. FIGS. 15c and d however, shows that the $E_f$ was poorly correlated with both HER2 and HER3 insensitivity.

Thus, the above Examples show that the methods of the present invention can be used to detect protein-protein interactions in both cells and tissue samples. These methods can be useful, for example, in detecting protein-protein interactions in breast cancer tissue, such as by detecting and/or measuring HER2-HER3 interaction.

These results clearly highlight how the TSA system combined with secondary Fab fragment antibody-dye conjugates enhances the detection of HER2 and HER3 in cells and tumours, whilst maintaining high specificity.

The Fab fragment-based TSA assay was both sensitive and specific for detecting HER2 and HER3 interactions in cells and tumour sections.

Therefore, this was assay exploited to develop a more sensitive and generic two-site FRET assay. To detect time resolved FRET multiple frequency domain-FLIM (mFD FLIM) was used (FIG. 2). Schematic diagrams show the principle of the coincidence TSA-FRET with Fab fragments conjugates as secondary antibodies (FIG. 1).

These results also show that small secondary antibody Fab fragments (50 kDa) result in a viable proximity between FRET pairs, and that the TSA system amplified the overall signal, thereby resulting in a higher FRET efficiency.

In the present specification "comprises" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

REFERENCES

1. Gerlinger, M. et al. Intratumour heterogeneity and branched evolution revealed by multiregion sequencing. *The New England journal of medicine* 366, 883-92 (2012).
2. Magdeldin, S. & Yamamoto, T. Toward deciphering proteomes of formalinfixed paraffin-embedded (FFPE) tissues. *Proteomics* 12, 1045-58 (2012).
3. Thomas, C. C., Deak, M., Alessi, D. R. & van Aalten, D. M. F. High-resolution structure of the pleckstrin homology domain of protein kinase b/akt bound to phosphatidylinositol (3,4,5)-trisphosphate. *Current biology: CB* 12, 1256-62 (2002).
4. Chin, Y. R. & Toker, A. Function of Akt/PKB signaling to cell motility, invasion and the tumour stroma in cancer. *Cellular Signalling* 21, 470-476 (2009).
5. Scheid, M. P. & Woodgett, J. R. PKB/AKT: functional insights from genetic models. Nature reviews. *Molecular cell biology* 2, 760-8 (2001).
6. Grille, S. J. et al. The protein kinase Akt induces epithelial mesenchymal transition and promotes enhanced motility and invasiveness of squamous cell carcinoma lines. *Cancer Res* 63, 2172-2178 (2003).
7. Kirkegaard, T. et al. AKT activation predicts outcome in breast cancer patients treated with tamoxifen. *The Journal of pathology* 207, 139-46 (2005).
8. Li, H.-F., Kim, J.-S. & Waldman, T. Radiation-induced Akt activation modulates radioresistance in human glioblastoma cells. *Radiation oncology* (London, England) 4, 43 (2009).

9. D Sarbassov, D., A Guertin, D., M Ali, S. & M Sabatini, D. Phosphorylation and regulation of Akt/PKB by the rictor-mTOR complex. *Science* 307, 1098-1101 (2005).
10. Heeg, S. et al. EGFR overexpression induces activation of telomerase via PI3K/AKT-mediated phosphorylation and transcriptional regulation through Hif1-alpha in a cellular model of oral-esophageal carcinogenesis. *Cancer science* 102, 351-60 (2011).
11. Bellacosa, A., Kumar, C. C., Di Cristofano, A. & Testa, J. R. Activation of AKT kinases in cancer: implications for therapeutic targeting. *Advances in cancer research* 94, 29-86 (2005). 27
12. R Sellers, W. Targeting the PI3K pathway in cancer. *Molecular Cancer Therapeutics* (2009). at <http://www-.mendeley.com/research/targeting-thepi3k-pathway-in-cancer/>
13. Simon, R., Mirlacher, M. & Sauter, G. Immunohistochemical analysis of tissue microarrays. *Methods in molecular biology* (Clifton, N.J.) 664, 113-26 (2010).
14. Bertucci, F. & Birnbaum, D. Reasons for breast cancer heterogeneity. *Journal of biology* 7, 6 (2008).
15. Polyak, K. Heterogeneity in breast cancer. *The Journal of clinical investigation* 121, 3786-8 (2011).
16. J Majewski, I. & Bernards, R. Taming the dragon: genomic biomarkers to individualize the treatment of cancer. *Nature Medicine* 17, 304-312 (2011).
17. Ng, T. Imaging Protein Kinase C Activation in Cells. *Science* 283, 2085-2089 (1999).
18. Kong, A. et al. Prognostic value of an activation state marker for epidermal growth factor receptor in tissue microarrays of head and neck cancer. *Cancer research* 66, 2834-43 (2006).
19. Calleja, V., Leboucher, P. & Larijani, B. Protein activation dynamics in cells and tumour micro arrays assessed by time resolved Förster resonance energy transfer. *Methods in enzymology* 506, 225-46 (2012).
20. Pietraszewska-Bogiel, A. & Gadella, T. W. J. FRET microscopy: from principle to routine technology in cell biology. *Journal of microscopy* 241, 111-8 (2011).
21. Voss, T. C., Demarco, I. A. & Day, R. N. Quantitative imaging of protein interactions in the cell nucleus. *BioTechniques* 38, 413-24 (2005).
22. Calleja, V. et al. Intramolecular and intermolecular interactions of protein kinase B define its activation in vivo. *PLoS biology* 5, e95 (2007).
23. Förster, T. Zwischenmolekulare Energiewanderung and Fluoreszenz. *Annalen der Physik* 437, 55-75 (1948).
24. Nelson, A. L. Antibody fragments: hope and hype. *mAbs* 2, 77-83
25. Chames, P., Van Regenmortel, M., Weiss, E. & Baty, D. Therapeutic antibodies: successes, limitations and hopes for the future. *British journal of pharmacology* 157, 220-33 (2009).
26. Toda, Y. et al. Application of tyramide signal amplification system to immunohistochemistry: a potent method to localize antigens that are not detectable by ordinary method. *Pathology international* 49, 479-83 (1999). 28
27. Calleja, V., Laguerre, M., Parker, P. J. & Larijani, B. Role of a Novel PH Kinase Domain Interface in PKB/Akt Regulation: Structural Mechanism for Allosteric Inhibition. *PLoS Biology* 7, 1 (2009).
28. Vira, S., Mekhedov, E., Humphrey, G. & Blank, P. S. Fluorescent-labeled antibodies: Balancing functionality and degree of labeling. *Analytical biochemistry* 402, 146-50 (2010).
29. Stryer, L. Fluorescence Energy Transfer as a Spectroscopic Ruler. *Annual Review of Biochemistry* 47, 819-846 (1978).
30. Kass, M., Witkin, A. & Terzopoulos, D. Snakes: Active contour models. *International Journal of Computer Vision* 1, 321-331 (1988).
31. Vartiainen, M. K., Guettler, S., Larijani, B. & Treisman, R. Nuclear actin regulates dynamic subcellular localization and activity of the SRF cofactor MAL. *Science* (New York, N.Y.) 316, 1749-52 (2007).
32. König, P., Krasteva, G., Tag, C., Koönig, I. R., Arens, C., & Kummer, W. FRET-CLSM and double-labeling indirect immunofluorescence to detect close association of proteins in tissue sections. *Laboratory Investigation* (2006) 86, 853-864.
33. Tokunaga E, Kimura Y, Oki E, Ueda N, Futatsugi M, Mashino K, et al. Akt is frequently activated in HER2/neu-positive breast cancers and associated with poor prognosis among hormone-treated patients. International journal of cancer Journal international du cancer. 2006; 118:284-9.

The invention claimed is:

1. A method for detecting molecular interactions, employing:
    a. at least two primary antibodies, wherein the first primary antibody binds to a first site on a molecule and the second primary antibody binds to a second site on a molecule, wherein the second site is different from the first site, wherein the first primary antibody binds to Akt(pan) and the second primary antibody binds to pAkt(T308) on the Akt 1, Akt 2 or Akt 3 protein, and wherein the first and second primary antibodies are immunologically distinct;
    b. at least two secondary antibodies, wherein the first secondary antibody is labelled with a fluorescence resonance energy transfer (FRET) donor and binds to the first primary antibody; and the second secondary antibody is conjugated or fused to an enzyme and binds the second primary antibody, wherein the first secondary antibody does not bind the second primary antibody and the second secondary antibody does not bind the first primary antibody, wherein one of the at least two secondary antibodies is not whole immunoglobulin; and
    c. a conjugate comprising a FRET acceptor and a substrate specific for the enzyme, wherein when the substrate reacts with the enzyme, an activated conjugate forms, which activated conjugate binds to electron rich moieties on a molecular surface adjacent to the enzyme;
    wherein the method comprises carrying out the following steps in order:
    d. contacting a sample with the at least two primary antibodies;
    e. contacting the sample with the at least two secondary antibodies;
    f. performing a wash step;
    g. contacting the sample with the conjugate; and
    h. detecting any FRET signal generated by the FRET acceptor,
    wherein a positive FRET signal will be detected when the FRET donor is on the bound first secondary antibody and the FRET acceptor is on the bound activated conjugate and the FRET donor is located within less than 10 nm from the FRET acceptor, and
    wherein no FRET signal will be detected when the FRET donor is on the bound first secondary antibody and the FRET acceptor is on the bound activated conjugate and the FRET donor is located greater than 10 nm from the FRET acceptor, or either or both of the first and second sites are not present in the sample.

2. The method of claim 1, wherein the at least two primary antibodies are selected from the group consisting of whole immunoglobulins, antibody or antigen-binding fragments thereof or combinations thereof.

3. The method of claim 1, wherein the at least two secondary antibodies are antibody or antigen-binding fragments.

4. The method of claim 2, wherein the antibody or antigen-binding fragments are Fab fragments, scFv fragments or combinations thereof.

5. The method of claim 1, wherein the FRET donor is selected from the group consisting of ORG 488, GFp, fluorescein, IAEDANS, EDANS, BODIPY FL and combinations thereof.

6. The method of claim 1, wherein the FRET acceptor is selected from the group consisting of ALX 594, mRFP, tetramethylrhodamine, fluorescein, dabcyl, BODIPY FL, QSY 7, QSY 9 and combinations thereof.

7. The method of claim 1, wherein the enzyme is selected from the group consisting of oxidoreductases, hydrolases, lyases, transferases, isomerases, and ligases.

8. The method of claim 1, wherein the enzyme is selected from the group consisting of peroxidases, oxidases, phosphatases, esterases and glycosidases.

9. The method of claim 8, wherein the enzyme is selected from the group consisting of horseradish peroxidase, glucose oxidase, alkaline phosphatase and beta-galactosidase.

10. The method of claim 1, wherein the substrate is tyramine.

11. The method of claim 1, wherein the primary antibodies are unlabelled.

12. The method of claim 1, wherein the first primary antibody is a murine antibody and the second primary antibody is a rabbit antibody.

13. The method of claim 12, wherein the first secondary antibody is an anti-murine antibody and the second secondary antibody is an anti-rabbit antibody.

14. The method of claim 1, wherein the method detects Akt activation in the sample.

15. The method of claim 1, wherein the sample is a tumour sample.

16. The method of claim 1, wherein the first primary antibody binders to HER2 and the second primary antibody binds to HER3.

17. The method of claim 1, wherein the first primary antibody binds to HER3 and the second primary antibody binds to HER2.

18. The method of claim 16, wherein the method detects HER2/HER3 dimerization in the sample.

19. The method of claim 18, wherein the sample is a tumour sample.

20. The method of claim 19, wherein the sample is a breast tumour sample.

21. The method of claim 1, wherein the at least two primary antibodies or the at least two secondary antibodies are contacted with the sample simultaneously one another.

22. The method of claim 1, wherein the at least two primary antibodies or the at least two secondary antibodies are contacted with the sample sequentially to one another.

23. The method of claim 21, wherein the at least two primary antibodies are contacted with the sample simultaneously to the at least two secondary antibodies.

24. The method of claim 1, wherein the at least two primary antibodies are contacted with the sample before the at least two secondary antibodies.

25. The method of claim 22 wherein a wash step is performed after the at least two primary antibodies are contacted with the sample and before the at least two secondary antibodies are contacted with the sample.

26. The method of claim 1, wherein the first secondary antibody is directly labelled with a FRET donor.

27. The method of claim 1, wherein the sample is a tissue sample.

28. The method of claim 1, wherein the molecule is a protein.

29. The method of claim 1, wherein the first site and the second site are on the same molecule.

30. The method of claim 1, wherein the first site and second site are on different molecules.

31. The method of claim 1, further comprising the step of quantifying interaction between the first site and the second site.

32. The method of claim 3, wherein the antibody or antigen-binding fragments are Fab fragments, scFv fragments or combinations thereof.

33. The method of claim 17, wherein the method detects HER2/HER3 dimerization in the sample.

* * * * *